(12) United States Patent
Yoo et al.

(10) Patent No.: US 11,253,590 B2
(45) Date of Patent: Feb. 22, 2022

(54) ANTIBODIES SPECIFIC TO GLYCOSYLATED BTLA (B- AND T-LYMPHOCYTE ATTENUATOR)

(71) Applicant: STSCIENCES, INC., Seoul (KR)

(72) Inventors: Stephen Sunghan Yoo, Centreville, VA (US); Ezra Myung Chul Chung, North Potomac, MD (US); Yong-Soo Kim, Rockville, MD (US); Andrew H. Park, Gaithersburg, MD (US)

(73) Assignee: STSCIENCES, INC., Seoul (KR)

( * ) Notice: Subject to any disclaimer, the term of this patent is extended or adjusted under 35 U.S.C. 154(b) by 840 days.

(21) Appl. No.: 15/781,064

(22) PCT Filed: Dec. 1, 2016

(86) PCT No.: PCT/US2016/064385
§ 371 (c)(1),
(2) Date: Jun. 1, 2018

(87) PCT Pub. No.: WO2017/096017
PCT Pub. Date: Jun. 8, 2017

(65) Prior Publication Data
US 2018/0264110 A1    Sep. 20, 2018

Related U.S. Application Data

(60) Provisional application No. 62/262,293, filed on Dec. 2, 2015.

(51) Int. Cl.
| | | |
|---|---|---|
| C07K 16/00 | (2006.01) | |
| A61K 39/395 | (2006.01) | |
| C07K 16/28 | (2006.01) | |
| G01N 33/574 | (2006.01) | |
| A61K 39/00 | (2006.01) | |
| A61P 35/00 | (2006.01) | |

(52) U.S. Cl.
CPC .... *A61K 39/39558* (2013.01); *C07K 16/2818* (2013.01); *G01N 33/57492* (2013.01); *A61K 2039/505* (2013.01); *A61P 35/00* (2018.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,842,067 A | 10/1974 | Sarantakis |
| 3,850,752 A | 11/1974 | Schuurs et al. |
| 3,862,925 A | 1/1975 | Sarantakis et al. |
| 3,939,350 A | 2/1976 | Kronick et al. |
| 3,972,859 A | 8/1976 | Fujino et al. |
| 3,996,345 A | 12/1976 | Ullman et al. |
| 4,105,603 A | 8/1978 | Vale et al. |
| 4,179,337 A | 12/1979 | Davis et al. |
| 4,196,265 A | 4/1980 | Koprowski et al. |
| 4,275,149 A | 6/1981 | Litman et al. |
| 4,277,437 A | 7/1981 | Maggio |
| 4,366,241 A | 12/1982 | Tom et al. |
| 4,444,887 A | 4/1984 | Hoffmann |
| 4,469,797 A | 9/1984 | Albarella |
| 4,472,509 A | 9/1984 | Gansow et al. |
| 4,485,045 A | 11/1984 | Regen |
| 4,526,938 A | 7/1985 | Churchill et al. |
| 4,544,545 A | 10/1985 | Ryan et al. |
| 4,606,855 A | 8/1986 | Deutsch et al. |
| 4,676,980 A | 6/1987 | Segal et al. |
| 4,703,003 A | 10/1987 | Struck |
| 4,716,111 A | 12/1987 | Osband et al. |
| 4,741,900 A | 5/1988 | Alvarez et al. |
| 4,742,159 A | 5/1988 | Batz et al. |
| 4,767,720 A | 8/1988 | Lingwood |
| 4,816,397 A | 3/1989 | Boss et al. |

(Continued)

FOREIGN PATENT DOCUMENTS

| | | |
|---|---|---|
| EP | 0 592 106 B1 | 4/1994 |
| EP | 0 239 400 B1 | 8/1994 |

(Continued)

OTHER PUBLICATIONS

Almagro & Fransson, Frontiers in Bioscience 2008; 13:1619-33 (Year: 2008).*
Padlan (Advances in Protein Chemistry, 1996, 49:57-133) (Year: 1996).*
Berglund et al, Protein Science, 2008, 17:606-613 (Year: 2008).*
Corada (Blood, 2001; 97:1679-84) (Year: 2001).*
Kulkarni-Kale et al. Nucleic Acid Research, 2005, 33:W168-W171 (Year: 2005).*
Abra et al., "The next generation of liposome delivery systems: recent experience with tumor-targeted, sterically-stabilized immunoliposomes and active-loading gradients." *Journal of liposome research* 12.1-2 (2002): 1-3.

(Continued)

*Primary Examiner* — Meera Natarajan
(74) *Attorney, Agent, or Firm* — Jones Day

(57) ABSTRACT

Provided herein are molecules, such as antibodies, that selectively bind to glycosylated BTLA (B- and T-lymphocyte attenuator) relative to unglycosylated BTLA. Methods for making and using such molecules are also provided, including methods for treating or diagnosing cancer. In some embodiments, the anti-glycosylated BTLA antibodies provided herein can immunospecifically bind to glycosylated wild-type BTLA (WT). In some embodiments, the anti-glycosylated BTLA antibodies provided herein can immunospecifically bind to one or more BTLA double mutants that retain only a single glycosylation site at BTLA N75, N94 or N110. In some embodiments, the anti-glycosylated BTLA antibodies provided herein show only background binding, if any, to a BTLA triple mutant, that retains none of BTLA's N75, N94, or N110 0-glycosylation sites.

30 Claims, 13 Drawing Sheets

Figures 1A, 1B:
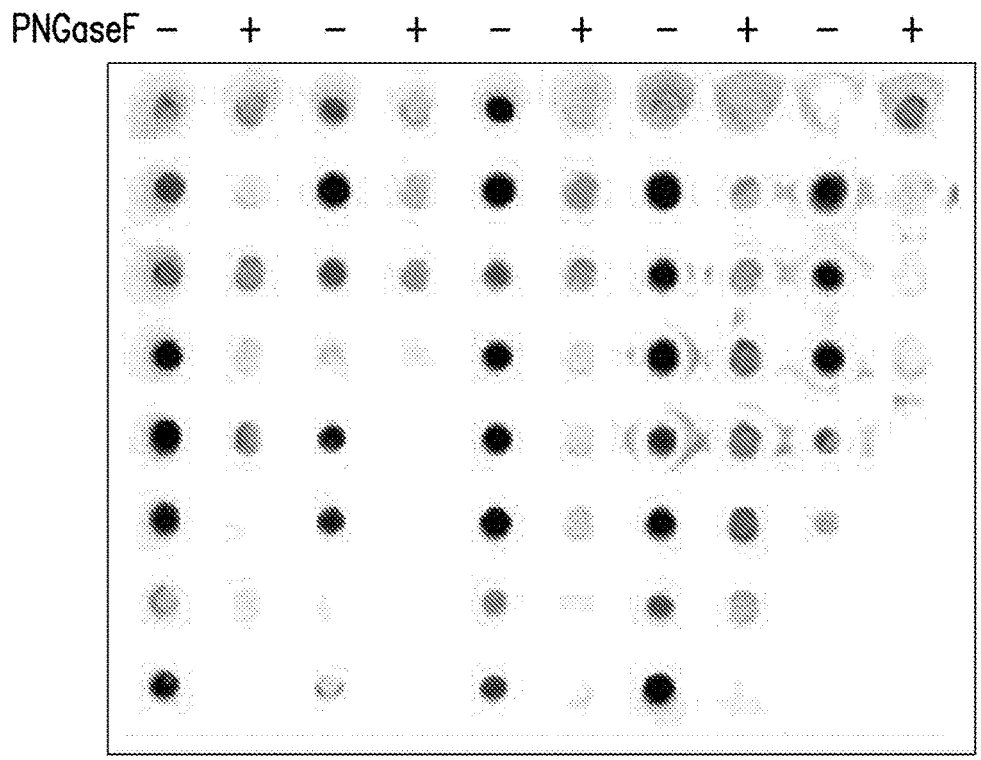

Specification includes a Sequence Listing.

(56) References Cited

U.S. PATENT DOCUMENTS

| | | |
|---|---|---|
| 4,816,567 A | 3/1989 | Cabilly et al. |
| 4,867,973 A | 9/1989 | Goers et al. |
| 4,870,287 A | 9/1989 | Cole et al. |
| 4,880,078 A | 11/1989 | Inoue et al. |
| 4,938,948 A | 7/1990 | Ring et al. |
| 4,946,778 A | 8/1990 | Ladner et al. |
| 4,980,286 A | 12/1990 | Morgan et al. |
| 5,013,556 A | 5/1991 | Woodle et al. |
| 5,021,236 A | 6/1991 | Gries et al. |
| 5,091,513 A | 2/1992 | Huston et al. |
| 5,128,326 A | 7/1992 | Balazs et al. |
| 5,164,296 A | 11/1992 | Blaustein et al. |
| 5,196,066 A | 3/1993 | Kusuda et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,403,484 A | 4/1995 | Ladner et al. |
| 5,413,923 A | 5/1995 | Kucherlapati et al. |
| 5,420,253 A | 5/1995 | Emery et al. |
| 5,427,908 A | 6/1995 | Dower et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,587,459 A | 12/1996 | Uckun |
| 5,618,709 A | 4/1997 | Gewirtz et al. |
| 5,625,126 A | 4/1997 | Lonberg et al. |
| 5,627,052 A | 5/1997 | Schrader |
| 5,633,425 A | 5/1997 | Lonberg et al. |
| 5,642,821 A | 7/1997 | Hafliger |
| 5,648,239 A | 7/1997 | Hawkins et al. |
| 5,656,434 A | 8/1997 | Terano et al. |
| 5,658,727 A | 8/1997 | Barbas et al. |
| 5,661,016 A | 8/1997 | Lonberg et al. |
| 5,679,377 A | 10/1997 | Bernstein et al. |
| 5,698,426 A | 12/1997 | Huse |
| 5,728,868 A | 3/1998 | Springer et al. |
| 5,733,743 A | 3/1998 | Johnson et al. |
| 5,734,033 A | 3/1998 | Reed |
| 5,739,169 A | 4/1998 | Ocain et al. |
| 5,750,753 A | 5/1998 | Kimae et al. |
| 5,760,395 A | 6/1998 | Johnstone |
| 5,770,376 A | 6/1998 | Bagrov |
| 5,780,225 A | 7/1998 | Wigler et al. |
| 5,789,208 A | 8/1998 | Sharon |
| 5,801,005 A | 9/1998 | Cheever et al. |
| 5,807,715 A | 9/1998 | Morrison et al. |
| 5,814,318 A | 9/1998 | Lonberg et al. |
| 5,821,047 A | 10/1998 | Garrard et al. |
| 5,821,337 A | 10/1998 | Carter et al. |
| 5,824,311 A | 10/1998 | Greene et al. |
| 5,830,880 A | 11/1998 | Sedlacek et al. |
| 5,840,745 A | 11/1998 | Buzzetti et al. |
| 5,843,597 A | 12/1998 | Getz |
| 5,844,091 A | 12/1998 | Blaustein et al. |
| 5,846,945 A | 12/1998 | McCormick |
| 5,855,913 A | 1/1999 | Hanes et al. |
| 5,858,657 A | 1/1999 | Winter et al. |
| 5,861,155 A | 1/1999 | Lin |
| 5,863,904 A | 1/1999 | Nabel et al. |
| 5,871,907 A | 2/1999 | Winter et al. |
| 5,872,223 A | 2/1999 | Uckun |
| 5,874,064 A | 2/1999 | Edwards et al. |
| 5,885,834 A | 3/1999 | Epstein |
| 5,888,533 A | 3/1999 | Dunn |
| 5,911,995 A | 6/1999 | Uckun |
| 5,912,015 A | 6/1999 | Bernstein et al. |
| 5,916,597 A | 6/1999 | Lee et al. |
| 5,916,771 A | 6/1999 | Hori et al. |
| 5,922,844 A | 7/1999 | Hawkins et al. |
| 5,925,376 A | 7/1999 | Heng |
| 5,934,272 A | 8/1999 | Lloyd et al. |
| 5,939,598 A | 8/1999 | Kucherlapati et al. |
| 5,945,155 A | 8/1999 | Grill et al. |
| 5,958,769 A | 9/1999 | Roberts et al. |
| 5,969,108 A | 10/1999 | McCafferty et al. |
| 5,985,309 A | 11/1999 | Edwards et al. |
| 5,985,877 A | 11/1999 | Dionne et al. |
| 5,989,463 A | 11/1999 | Tracy et al. |
| 5,998,596 A | 12/1999 | Bergan et al. |
| 6,019,968 A | 2/2000 | Platz et al. |
| 6,034,053 A | 3/2000 | Uckun et al. |
| 6,040,305 A | 3/2000 | Taveras et al. |
| 6,051,574 A | 4/2000 | Anthony |
| 6,051,582 A | 4/2000 | Taveras |
| 6,054,297 A | 4/2000 | Carter et al. |
| 6,054,466 A | 4/2000 | Ciccarone et al. |
| 6,057,300 A | 5/2000 | Nabel et al. |
| 6,063,930 A | 5/2000 | Dinsmore et al. |
| 6,066,738 A | 5/2000 | Dinsmore et al. |
| 6,071,935 A | 6/2000 | Lyssikatos |
| 6,077,853 A | 6/2000 | Graham et al. |
| 6,080,870 A | 6/2000 | Anthony et al. |
| 6,090,948 A | 7/2000 | Dinsmore et al. |
| 6,093,737 A | 7/2000 | Anthony et al. |
| 6,103,723 A | 8/2000 | Bergman et al. |
| 6,124,295 A | 9/2000 | Taveras et al. |
| 6,124,465 A | 9/2000 | Bourzat et al. |
| 6,127,366 A | 10/2000 | Kim et al. |
| 6,133,303 A | 10/2000 | Bikker et al. |
| 6,143,766 A | 11/2000 | Kaltenbronn et al. |
| 6,159,984 A | 12/2000 | Guzi et al. |
| 6,165,464 A | 12/2000 | Hudziak et al. |
| 6,169,096 B1 | 1/2001 | Venet et al. |
| 6,187,786 B1 | 2/2001 | Venet et al. |
| 6,194,551 B1 | 2/2001 | Idusogie et al. |
| 6,211,193 B1 | 4/2001 | Remiszewski et al. |
| 6,218,372 B1 | 4/2001 | Nabel et al. |
| 6,218,406 B1 | 4/2001 | Bourzat et al. |
| 6,218,410 B1 | 4/2001 | Uehata et al. |
| 6,225,322 B1 | 5/2001 | Cooper et al. |
| 6,228,856 B1 | 5/2001 | Njoroge et al. |
| 6,228,865 B1 | 5/2001 | Doll et al. |
| 6,232,338 B1 | 5/2001 | Davies et al. |
| 6,239,140 B1 | 5/2001 | Cooper et al. |
| 6,242,196 B1 | 6/2001 | Spiegelman et al. |
| 6,245,759 B1 | 6/2001 | Bilodeau et al. |
| 6,248,756 B1 | 6/2001 | Anthony et al. |
| 6,265,422 B1 | 7/2001 | Bikker et al. |
| 6,268,363 B1 | 7/2001 | Lee et al. |
| 6,271,242 B1 | 8/2001 | Barbacid |
| 6,277,375 B1 | 8/2001 | Ward |
| 6,277,832 B1 | 8/2001 | Sugiyama et al. |
| 6,300,501 B1 | 10/2001 | Dobrusin et al. |
| 6,331,415 B1 | 12/2001 | Cabilly et al. |
| 6,335,156 B1 | 1/2002 | Hermeking et al. |
| 6,342,487 B1 | 1/2002 | Riou et al. |
| 6,342,765 B1 | 1/2002 | Arnould |
| 6,362,188 B1 | 3/2002 | Guzi et al. |
| 6,365,157 B2 | 4/2002 | Rockwell et al. |
| 6,369,034 B1 | 4/2002 | Doherty et al. |
| 6,372,747 B1 | 4/2002 | Taveras et al. |
| 6,383,790 B1 | 5/2002 | Shokat |
| 6,387,905 B2 | 5/2002 | Njoroge et al. |
| 6,399,615 B1 | 6/2002 | Guzi et al. |
| 6,399,633 B1 | 6/2002 | Dumont et al. |
| 6,403,581 B1 | 6/2002 | Ayral-Kaloustian et al. |
| 6,406,867 B1 | 6/2002 | Yu et al. |
| 6,407,213 B1 | 6/2002 | Carter et al. |
| 6,410,539 B1 | 6/2002 | Arnould |
| 6,410,541 B2 | 6/2002 | Remiszewski et al. |
| 6,414,145 B1 | 7/2002 | Boyle et al. |
| 6,420,387 B1 | 7/2002 | Venet et al. |
| 6,432,959 B1 | 8/2002 | Cooper et al. |
| 6,436,960 B1 | 8/2002 | Shin et al. |
| 6,440,974 B2 | 8/2002 | Doll et al. |
| 6,451,812 B1 | 9/2002 | End et al. |
| 6,458,935 B1 | 10/2002 | Burns et al. |
| 6,639,055 B1 | 10/2003 | Carter et al. |

(56) References Cited

U.S. PATENT DOCUMENTS

| | | | |
|---|---|---|---|
| 6,709,659 | B1 | 3/2004 | Lok et al. |
| 6,709,873 | B1 | 3/2004 | Yatscoff et al. |
| 6,719,971 | B1 | 4/2004 | Carter et al. |
| 6,753,407 | B2 | 6/2004 | Noga et al. |
| 6,787,153 | B1 | 9/2004 | Hosokawa et al. |
| 6,800,738 | B1 | 10/2004 | Carter et al. |
| 6,814,965 | B2 | 11/2004 | Gao et al. |
| 6,849,259 | B2 | 2/2005 | Haurum et al. |
| 6,861,572 | B1 | 3/2005 | Etches et al. |
| 6,875,434 | B1 | 4/2005 | Schenk |
| 6,881,557 | B2 | 4/2005 | Foote |
| 6,891,024 | B2 | 5/2005 | Marsh |
| 6,946,546 | B2 | 9/2005 | Vaughan et al. |
| 6,982,323 | B1 | 1/2006 | Wang et al. |
| 7,407,659 | B2 | 8/2008 | Karumanchi et al. |
| 8,178,098 | B2 | 5/2012 | Lahn et al. |
| 2003/0044407 | A1 | 3/2003 | Chang et al. |
| 2005/0074403 | A1 | 4/2005 | Kayyem et al. |
| 2005/0214860 | A1 | 9/2005 | Zhu et al. |
| 2011/0014438 | A1* | 2/2011 | Mataraza et al. |
| 2014/0242077 | A1 | 8/2014 | Choi et al. |
| 2020/0148768 | A1 | 5/2020 | Yoo et al. |

FOREIGN PATENT DOCUMENTS

| | | |
|---|---|---|
| EP | 0 519 596 B1 | 2/2005 |
| GB | 2 188 638 B | 5/1990 |
| GB | 2 209 757 B | 10/1990 |
| WO | WO 88/07089 A1 | 9/1988 |
| WO | WO 89/07142 A1 | 8/1989 |
| WO | WO 90/02809 A1 | 3/1990 |
| WO | WO 91/05548 A1 | 5/1991 |
| WO | WO 91/09967 A1 | 7/1991 |
| WO | WO 91/10737 A1 | 7/1991 |
| WO | WO 91/10741 A1 | 7/1991 |
| WO | WO 92/01047 A1 | 1/1992 |
| WO | WO 92/18619 A1 | 10/1992 |
| WO | WO 92/19244 A2 | 11/1992 |
| WO | WO 92/22324 A1 | 12/1992 |
| WO | WO 93/11236 A1 | 6/1993 |
| WO | WO 95/15982 A2 | 6/1995 |
| WO | WO 95/20401 A1 | 8/1995 |
| WO | WO 96/20698 A2 | 7/1996 |
| WO | WO 96/33735 A1 | 10/1996 |
| WO | WO 96/34096 A1 | 10/1996 |
| WO | WO 97/32572 A2 | 9/1997 |
| WO | WO 97/33899 A1 | 9/1997 |
| WO | WO 97/34911 A1 | 9/1997 |
| WO | WO 97/38731 A1 | 10/1997 |
| WO | WO 97/44013 A1 | 11/1997 |
| WO | WO 98/16654 A1 | 4/1998 |
| WO | WO 98/23289 A1 | 6/1998 |
| WO | WO 98/24893 A2 | 6/1998 |
| WO | WO 98/31346 A1 | 7/1998 |
| WO | WO 98/46645 A2 | 10/1998 |
| WO | WO 98/50433 A2 | 11/1998 |
| WO | WO 99/15154 A1 | 4/1999 |
| WO | WO 99/20253 A1 | 4/1999 |
| WO | WO 99/23105 A1 | 5/1999 |
| WO | WO 99/51642 A1 | 10/1999 |
| WO | WO 99/58572 A1 | 11/1999 |
| WO | WO 99/63088 A2 | 12/1999 |
| WO | WO 99/66903 A2 | 12/1999 |
| WO | WO 2000/042072 A2 | 7/2000 |
| WO | WO 2003/085124 A2 | 10/2003 |
| WO | WO 2004/028564 A2 | 4/2004 |
| WO | WO 2004/029092 A2 | 4/2004 |
| WO | WO 2004/029207 A2 | 4/2004 |
| WO | WO 2008/076560 A2 | 6/2008 |
| WO | WO 2009/030884 A2 | 3/2009 |
| WO | WO 2011/014438 A1 | 2/2011 |
| WO | WO 2015/100219 A1 | 7/2015 |
| WO | WO 2015/145360 A1 | 10/2015 |
| WO | WO 2015/191861 A1 | 12/2015 |
| WO | WO 2017/096017 A1 | 6/2017 |

OTHER PUBLICATIONS

Al-Lazikani et al., "Standard conformations for the canonical structures of immunoglobulins." *Journal of molecular biology* 273.4 (1997): 927-948.

Allen et al., "Large unilamellar liposomes with low uptake into the reticuloendothelial system." *FEBS letters* 223.1 (1987): 42-46.

Allen et al., "The use of glycolipids and hydrophilic polymers in avoiding rapid uptake of liposomes by the mononuclear phagocyte system." *Advanced drug delivery reviews* 13.3 (1994): 285-309.

Allen et al., "Antibody-Targeted Stealth® Liposomes", *Stealth Liposomes*, CRC Press, Boca Raton, 20: 233-244 (1995).

Alley et al., "Antibody-drug conjugates: targeted drug delivery for cancer," *Curr. Opin. Chem. Biol.*, 14(4):529-537 (2010).

Ames et al., "Conversion of murine Fabs isolated from a combinatorial phage display library to full length immunoglobulins," *J. Immunol. Methods*, 184:177-186 (1995).

Angal et al., "A single amino acid substitution abolishes the heterogeneity of chimeric mouse/human (IgG4) antibody," *Mol. Immunol.*, 30:105-108 (1993).

Anti-BTN1A1 antibody produced in rabbit affinity isolated antibody; Anti-BT; Sigma-Aldrich, retrieved from www.sigmaaldrich.com/catalog/product/sigma/av45164?lang=en®ion=US on May 14, 2021.

Arnett et al., "Immune modulation by butyrophilins," *Nat. Rev. Immunol.*, 14:559-569 (2014).

Arnon et al., "Monoclonal Antibodies for Immunotargeting of Drugs In Cancer Therapy", in Monoclonal Antibodies and Cancer Therapy, Reisfeld et al. (eds.), 1985, pp. 243-256, Alan R. Liss, Inc.

Aurrand-Lions et al., "Vanin-1, a novel GPI-linked perivascular molecule involved in thymus homing," *Immunity*, 5(5):391-405(1996).

Austin-Ward and Villaseca, "Gene therapy and its applications," *Rev Med Chil*, 126(7):838-845 (1998).

Ausubel et al., (Echoitds.), *Current Protocols in Moleuclar Biology*, John Wiley & Sons, Inc., New York, vol. I, pp. 6.3.1-6.3.6, 2.10.3 (1989).

Barbas et al., "In vitro evolution of a neutralizing human antibody to human immunodeficiency virus type 1 to enhance affinity and broaden strain cross-reactivity," *Proc. Natl. Acad. Sci. USA*, 91(9):3809-3813 (1994).

Barderas et al., "Affinity maturation of antibodies assisted by in silico modeling," *Proc. Natl. Acad. Sci. USA*, 105:9029-9034 (2008).

Barretina et al., "The Cancer Cell Line Encyclopedia enables predictive modelling of anticancer drug sensitivity," *Nature*, 483(7391):603-607 (2012).

Bendas, "Immunoliposomes," *BioDrugs*, 15(4):215-224 (2001).

Better et al., "*Escherichia coli* secretion of an active chimeric antibody fragment," *Science*, 240:1041-1043 (1988).

Blum et al., "Liposomes for the sustained drug release in vivo," *Biochim. Biophys. Acta.*, 1029: 91-97 (1990).

Bollenbach et al., "Evolution and multilevel optimization of the genetic code," *Genome Res.*, 17:401-404 (2007).

Bostrom et al., "Improving antibody binding affinity and ificity for therapeutic development," *Methods Mol. Biol.*, 525:353-376 (2009).

Brahmer et al., "Safety and activity of anti-PD-L1 antibody in patients with advanced cancer," *N. Engl. J. Med.*, 66:2455-2465 (2012).

Brinkmann et al., "Phage display of disulfide-stabilized Fv fragments." *Journal of immunological methods* 182.1 (1995): 41-50.

Buchwald et al., "Long-term, continuous intravenous heparin administration by an implantable infusion pump in ambulatory patients with recurrent venous thrombosis," *Surgery*, 88(4):507-516 (1980).

Bukowski et al., "Signal transduction abnormalities in T lymphocytes from patients with advanced renal carcinoma: clinical relevance and effects of cytokine therapy," *Clin. Cancer Res.*, 4(10):2337-2347 (1998).

Burton et al., "Human antibodies from combinatorial libraries," *Adv. Immunol.*, 57:191-280 (1994).

Carter et al., "Designer antibody-based therapeutics for oncology." *AACR Education Book* (2005): 147-54.

Carter et al., "Antibody-drug conjugates for cancer therapy," *Cancer J.*, 14(3):154-169 (2008).

(56) References Cited

OTHER PUBLICATIONS

Carter et al., "Humanization of an anti-p185HER2 antibody for human cancer therapy," *Proc. Natl. Acad. Sci. USA*, 89:4285-4289 (1992).
Chang et al., "p53 regulates epithelial-mesenchymal transition and stem cell properties through modulating miRNAs." *Nature cell biology* 13.3 (2011): 317-323.
Chang et al., "EZH2 promotes expansion of breast tumor initiating cells through activation of RAF1-β-catenin signaling," *Cancer Cell*, 19(1):86-100 (2011).
Chari, "Targeted cancer therapy: conferring ificity to cytotoxic drugs," *Acc. Chem. Res.*, 41(1):98-107 (2008).
Chen et al., "Selection and analysis of an optimized anti-VEGF antibody: crystal structure of an affinity-matured Fab in complex with antigen," *J. Mol. Biol.*, 293:865-881 (1999).
Cheng et al., "Structure and interactions of the human programmed cell death 1 receptor," *J. Biol. Chem.*, 288(17):11771-11785 (2013).
Cheung et al., "Scanning N-glycosylation mutagenesis of membrane proteins," *Methods*, 41:451-459 (2007).
Chothia et al., "Structural determinants in the sequenes of immunoglobulin variable domain," *J. Mol. Biol.*, 278:457-479 (1998).
Chothia et al., "The structural basis of antibody complementarity," *J. Mol. Biol.*, 196:901-917 (1987).
Christodoulides et al., "Immunization with recombinant class I outermembrane protein from Neisseria meningitidis: influence of liposomes and adjuvants on antibody avidity, recognition of native protein and the induction of a bactericidal immune response against meningococci." *Microbiology* 144.11 (1998): 3027-3037.
Cleek et al., "Biodegradable Polymeric Carriers for a bFGF Antibody for Cardiovascular Application," *Pro. Int'l. Symp. Control. Rel. Bioact. Mater.*, 24:853-854 (1997).
Compaan et al. "Attenuating lymphocyte activity: the crystal structure of the BTLA-HVEM complex." *J. Biol. Chem.*, 290.47 (2005): 39553-39561.
Davidson et al., "Intralesional cytokine therapy in cancer: a pilot study of GM-CSF infusion in mesothelioma," *J Immunother.*, 21(5):389-398(1998).
Davies et al., "Expression of GnTIII in a recombinant anti-CD20 CHO production cell line: Expression of antibodies with altered glycoforms leads to an increase in ADCC through higher affinity for FC gamma RIII," *Biotechnol. Bioeng.*, 74:288-294 (2001).
De Nardo et al., "Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts. ," *Clin Cancer Res.*, 4(10):2483-2490 (1998).
Desmyter et al., "Crystal structure of a camel single-domain VH antibody fragment in complex with lysozyme," *Nat. Struct. Biol.*, 3:803-811 (1996).
Dietrich et al., "Functional immobilization of a DNA-binding protein at a membrane interface via histidine tag and synthetic chelator lipids," *Biochemistry*, 35:1100-1105 (1996).
Doronina et al., "Development of potent monoclonal antibody aurtistatin conjugates for cancer therapy," *Nat. Biotechnol.*, 21(7):778-784(2003).
Ducry et al., "Antibody-drug conjugates: linking cytotoxic payloads to monoclonal antibodies," *Bioconjug. Chem.*, 21(1):5-13(2010).
Dunn et al., "Cancer immunoediting: from immunosurveillance to tumor escape." *Nature immunology* 3.11 (2002): 991-998.
During et al., "Controlled release of dopamine from a polymeric brain implant: in vivo characterization," *Ann. Neurol.*, 25(4):351-356 (1989).
Elliott et al., "Enhancement of therapeutic protein in vivo activities through glycoengineering," *Nat. Biotechnol.*, 21:414-421 (2003).
Eppstein et al., "Biological activity of liposome-encapsulated murine interferon gamma is mediated by a cell membrane receptor," *Proc. Natl. Acad. Sci. USA*, 82(11):3688-3692 (1985).
Finlay et al., "Affinity maturation of a humanized rat antibody for anti-RAGE therapy: comprehensive mutagenesis reveals a high level of mutational plasticity both inside and outside the complementarity-determining regions," *J. Mol. Biol.*, 388:541-558 (2009).
Foote et al., "Antibody framework residues affecting the conformation of the hypervariable loops," *J. Mol. Biol.*, 224(2):487-499 (1992).
Francisco et al. "The PD-1 pathway in tolerance and autoimmunity." *Immunological reviews* vol. 236 (2010): 219-42.
Gillies et al., "High-level expression of chimeric antibodies using adapted cDNA variable region cassettes," *J. Immunol. Methods*, 125:191-202 (1989).
Glaser et al., "Antibody engineering by codon-based mutagenesis in a filamentous phage vector system," *J. Immunol.*, 149:3903-3913 (1992).
Goodson, J. Max, "Medical Applications of Controlled Release", *Dental Applications*, 6:2, 115-138 (1984).
Gram et al., "In vitro selection and affinity maturation of antibodies from a naive combinatorial immunoglobulin library," *Proc. Natl. Acad. Sci. USA*, 89(8):3576-3580 (1992).
Grosjean et al., "Preferential codon usage in prokaryotic genes: the optimal codon-anticodon interaction energy and the selective codon usage in efficiently expressed genes," *Gene*, 18:199-209 (1982).
Gustchina et al., "Affinity maturation by targeted diversification of the CDR-H2 loop of a monoclonal Fab derived from a synthetic naive human antibody library and directed against the internal trimeric coiled-coil of gp41 yields a set of Fabs with improved HIV-1 neutralization potency and breadth," *Virology*, 393:112-119 (2009).
Hackel et al., "Stability and CDR composition biases enrich binder functionality landscapes," *J. Mol. Biol.*, 401:84-96 (2010).
Hamers-Casterman et al., "Naturally occurring antibodies devoid of light chains," *Nature*, 363:446-448 (1993).
Hamid et al., "Safety and tumor responses with lambrolizumab (anti-PD-1) in melanoma," *N. Eng. J. Med.*, 369(2):134-144 (2013).
Hanibuchi et al., "Therapeutic efficacy of mouse-human chimeric anti-ganglioside GM2 monoclonal antibody against multiple organ micrometastases of human lung cancer in NK cell-depleted SCID mice," *Int. J. Cancer*, 78(4):480-485 (1998).
Hansen et al., "Attachment of antibodies to sterically stabilized liposomes: evaluation, comparison and optimization of coupling procedures," *Biochim. Biophys. Acta.*, 1239(2):133-144 (1995).
Heifetz et al., "Mechanism of action of tunicamycin on the UDP-GlcNAc:dolichyl-phosphate Glc-NAc-1-phosphate transferase," *Biochemistry*, 18(11):2186-2192 (1979).
Helenius et al., "Intracellular functions of N-linked glycans," *Science*, 291:2364-2369 (2001).
Hellstrand et al., "Histamine and cytokine therapy," *Acta Oncol.*, 37(4):347-353 (1998).
Hellstrom et al., "Antibodies For Drug Delivery", in Controlled Drug Delivery, 2$^{nd}$ Edition, Robinson et al. (eds.), Marcel Dekker, Inc., pp. 623-653 (1987).
Hodi et al., "Improved survival with ipilimumab in patients with metastatic melanoma," *N. Engl. J. Med.*, 363(8):711-723 (2010).
Hollander, "Immunotherapy for B-Cell lymphoma: current status and prospective advances," *Frontiers in immunology* 3 (2012).
Honegger et al., "Yet another numbering scheme for immunoglobulin variable domains: an automatic modeling and analysis tool," *J. Mol. Biol.*, 309(3):657-670 (2001).
Howard et al., "Intracerebral drug delivery in rats with lesion-induced memory deficits," *J. Neurosurg.*, 71(1):105-112 (1989).
Hu et al., "IkappaB kinase promotes tumorigenesis through inhibition of forkhead FOXO3a," *Cell*, 117(2):225-237 (2004).
Hu et al., "Minibody: A novel engineered anti-carcinoembryonic antigen antibody fragment (single-chain Fv-CH3) which exhibits rapid, high-level targeting of xenografts," *Cancer Res.*, 56:3055-3061 (1996).
Hui et al., "Pathways for potentiation of immunogenicity during adjuvant-assisted immunizations with Plasmodium falciparum major merozoite surface protein 1," *Infect. Immun.*, 66(11):5329-5336(1998).
Huse, W. D. "Combinatorial antibody expression libraries in filamentous phage." *Antibody Engineering: A Practical Guide*, CAK Borrebaeck, ed. WH Freeman and Co., Publishers, New York (1991): 103-120.

(56) References Cited

OTHER PUBLICATIONS

Huston et al., "Antigen recognition and targeted delivery by the single-chain Fv," *Cell Biophys.*, 22:189-224 (1993).
Huston et al., "Protein engineering of single-chain Fv analogs and fusion proteins," *Methods Enzymol.*, 203:46-88 (1991).
Hwang et al., "Hepatic uptake and degradation of unilamellar sphingomyelin/cholesterol liposomes: a kinetic study," *Proc. Natl. Acad. Sci. USA*, 77: 4030-4034 (1980).
International Search Report issued for International Patent Application No. PCT/US2016/064385, dated Apr. 10, 2017 (7 pages).
Jestin et al., "Optimization models and the structure of the genetic code," *J. Mol. Evol.*, 69:452-457 (2009).
Joliot et al., "Antennapedia homeobox peptide regulates neural morphogenesis," *Proc. Natl. Acad. Sci. USA*, 88(5):1864-1868 (1991).
Jones et al., "Replacing the complementarity-determining regions in a human antibody with those from a mouse," *Nature*, 321(6069):522-525 (1986).
Kabat et al., "Unusual distributions of amino acids in complementarity-determining (hypervariable) segments of heavy and light chains of immunoglobulins and their possible roles in specificity of antibody-combining sites," *J. Biol. Chem.*, 252:6609-6616 (1977).
Kabat, Elvin A., "The structural basis for antibody complementary." *Advances in protein chemistry* 32 (1978): 1-75.
Kantarjian et al., "Treatment of Philadelphia chromosome-positive, accelerated-phase chronic myelogenous leukemia with imatinib mesylate," *Clin. Cancer Res.*, 8:2167-2176 (2002).
Katoh et al., "MAFFT: a novel method for rapid multiple sequence alignment based on fast Fourier transform," *Nucleic Acids Res.*, 30(14):3059-3066 (2002).
Kelley et al., "Folding of eukaryotic proteins produced in *Escherichia coli*." *Genetic engineering* (1990): 1-19p.
Kettleborough et al., "Isolation of tumor cell-specific single-chain Fv from immunized mice using phage-antibody libraries and the re-construction of whole antibodies from these antibody fragments," *Eur. J. Immunol.*, 24:952-958 (1994).
Klibanov et al., "Activity of amphipathic poly(ethylene glycol) 5000 to prolong the circulation time of liposomes depends on the liposome size and is unfavorable for immunoliposome binding to target," *Biochim Biophys Acta*, 1062(2):142-148 (1991).
Klibanov et al., "Amphipathic polyethyleneglycols effectively prolong the circulation time of liposomes," *FEBS Letts.*, 268(1):235-237 (1990).
Knappik et al., "An improved affinity tag based on the FLAG peptide for the detection and purification of recombinant antibody fragments," *Biotechniques*, 17(4):754-761 (1994).
Krause et al., "An insertion mutation that distorts antibody binding site architecture enhances function of a human antibody," *MBio*, 2:e000345-10, pp. 1-8 (2011).
Krieg et al., "Functional analysis of B and T lymphocyte attenuator engagement on CD4+ and CD8+ T cells," *J. Immunol.*, 175(10):6420-6427 (2005).
Kuan et al., "Affinity-matured anti-glycoprotein NMB recombinant immunotoxins targeting malignant gliomas and melanomas," *Int. J. Cancer*, 129:111-121 (2011).
Kurland et al., "Optimization of translation accuracy," *Prog. Nucleic Acid Res. Mol. Biol.*, 31:191-219 (1984).
La Mar et al., "Proton nuclear magnetic resonance investigation of the nature of solution conformational equilibriums of monomeric insect deoxyhemoglobins." *Biochemistry* 20.15 (1981): 4429-4436.
La Merrill et al., "Dietary fat alters pulmonary metastasis of mammary cancers through cancer autonomous and non-autonomous changes in gene expression," *Clin. Exp. Metastasis*, 27(2):107-116 (2010).
Lam et al., *Proc. Int'l. Symp. Control Rel. Bioact. Mater.* 24:759-760 (1997).
Langer et al., "Chemical and physical structure of polymers as carriers for controlled release of bioactive agents: a review," *J., Macromol. Sci. Rev. Macromol. Chem.*, 23:61-126 (1983).

Langer et al., "New methods of drug delivery," *Science*, 249(4976):1527-1533 (1990).
Leach et al., "Enhancement of antitumor immunity by CTLA-4 blockade." Science 271.5256 (1996): 1734-1736.
Lee et al., "IKKβ suppression of TSC1 links inflammation and tumor angiogenesis via the mTOR pathway," *Cell*, 130(3):440-455(2007).
Lefranc, Marie-Paule. "IMGT, the international ImMunoGeneTics database." *Nucleic acids research* 29.1 (2001): 207-209.
Levy et al. "Inhibition of calcification of bioprosthetic heart valves by local controlled-release diphosphonate." *Science* 228.4696 (1985): 190-192.
Lim et al., "Epigenetic changes induced by reactive oxygen species in hepatocellular carcinoma: methylation of the E-cadherin promoter," *Gastroenterology*, 135(6):2128-2140 (2008).
Lin et al., "The PD-1/PD-L1 complex resembles the antigen-binding Fv domains of antibodies and T cell receptors," *Proc. Natl. Acad. Sci. USA*, 105(8):3011-3016 (2008).
Litzinger et al., "Effect of liposome size on the circulation time and intraorgan distribution of amphipathic poly(ethylene glycol)-containing liposomes," *Biochim. Biophys. Acta*, 1190:99-107 (1994).
Lo et al., "Epidermal growth factor receptor cooperates with signal transducer and activator of transcription 3 to induce epithelial-mesenchymal transition in cancer cells via up-regulation of TWIST gene expression," *Cancer Res.*, 67(19):9066-9076 (2007).
Lonberg et al., "Human antibodies from transgenic mice," *Int. Rev. Immunol.*, 13:65-93 (1995).
Loughrey et al., "A non-covalent method of attaching antibodies to liposomes," *Biochim. Biophys. Acta*, 901:157-160 (1987).
Lowry et al., "Protein measurement with the folin phenol reagent," *J. Biol. Chem.*, 193:265-275 (1951).
Marchler-Bauer, et al. "CDD: a conserved domain database for the functional annotation of proteins," *Nucleic Acids Res.*, 39(Database issue):D225-D229 (2011).
Marglin et al., "Chemical synthesis of peptides and proteins." *Annual review of biochemistry* 39 (1970): 841-866.
Marks et al., "By-passing Immunization: building high affinity human antibodies by chain shuffling." *Bio/technology* 10.7 (1992): 779-783.
Martin et al., "Irreversible coupling of immunoglobulin fragments to preformed vesicles. An improved method for liposome targeting," *J. Biol. Chem.*, 257(1):286-288 (1982).
Martin et al., "Structural families in loops of homologous proteins: automatic classification, modelling and application to antibodies," *J. Mol. Biol.*, 263(5):800-815 (1996).
Maruyama et al., "Effect of molecular weight in amphipathic polyethyleneglycol on prolonging the circulation time of large unilamellar liposomes," *Chem. Pharm. Bull.*, 39: 1620-1622 (1991).
Maruyama, Kazuo. "In vivo targeting by liposomes." *Biological and Pharmaceutical Bulletin* 23.7 (2000): 791-799.
Merrifield, Robert B. "Solid phase peptide synthesis. I. The synthesis of a tetrapeptide." *Journal of the American Chemical Society* 85.14 (1963): 2149-2154.
Mohammad et al., "A new tubulin polymerization inhibitor, auristatin PE, induces tumor regression in a human Waldenstrom's macroglobulinemia xenograft model," *Int. J. Oncol.*, 15:367-372 (1999).
Mohammad et al., "Bryostatin 1 induces differentiation and potentiates the antitumor effect of Auristatin PE in a human pancreatic tumor (PANC-1) xenograft model," *Anticancer Drugs*, 12:735-740 (2001).
Monoclonal Anti-BTN1A1 antibody produced in mouse clone BTN1A1-A116, culture supernatant; Anti-BT; Sigma-Aldrich, retrieved from https://www.sigmaaldrich.com/catalog/product/sigma/sab4100132?lang=en®ion=US on May 14, 2021.
Montgomery et al., "Affinity maturation and characterization of a human monoclonal antibody against HIV-1 gp41 ," *MAbs*, 1:462-474 (2009).
Morea et al., "Antibody modeling: implications for engineering and design," *Methods*, 20:267-279 (2000).
Morrison et al., "Chimeric human antibody molecules: mouse antigen-binding domains with human constant region domains," *Proc. Natl. Acad. Sci. USA*, 81(21):6851-6855 (1984).

(56) References Cited

OTHER PUBLICATIONS

Morrison, "Transfectomas provide novel chimeric antibodies," *Science*, 229:1202-1207 (1985).
Mueller et al., "Humanized porcine VCAM-specific monoclonal antibodies with chimeric IgG2/G4 constant regions block human leukocyte binding to porcine endothelial cells," *Mol. Immunol.*, 34:441-452 (1997).
Mullinax et al., "Expression of a heterodimeric Fab antibody protein in one cloning step," *Biotechniques*, 12:864-869 (1992).
Murali et al., "Antibody like peptidomimetics as large scale immunodetection probes," *Cell Mol. Biol. (Noisy-le grand)*, 49:209-216 (2003).
Ning et al., "Intratumoral radioimmunotherapy of a human colon cancer xenograft using a sustained-release gel," *Radiother. Oncol.*, 39:179-189 (1996).
Oi et al., "Chimeric antibodies." *BioTechniques* 4.3 (1986): 214-221.
Okazaki et al., "A rheostat for immune responses: the unique properties of PD-1 and their advantages for clinical application," *Nat. Immunol.*, 14(12):1212-1218 (2013).
Order et al. "Analysis, results, and future prospective of the therapeutic use of radiolabeled antibody in cancer therapy." *Monoclonal antibodies for cancer detection and therapy*. 303-316 (1985).
Padlan, "A possible procedure for reducing the immunogenicity of antibody variable domains while preserving their ligand-binding properties," *Mol. Immunol.*, 28:489-498 (1991).
Page et al., "Immune modulation in cancer with antibodies," *Annu. Rev. Med.*, 65:185-202 (2014).
Park et al., "Immunoliposomes for cancer treatment," *Adv. Pharmacol.*, 40:399-435 (1997).
Park, Yong Serk. "Tumor-directed targeting of liposomes." *Bioscience reports* 22.2 (2002): 267-281.
Paulos et al., "Putting the brakes on BTLA in T cell-mediated cancer immunotherapy." *The Journal of clinical investigation* 120.1 (2010): 76-80.
Peng et al., "Epigenetic silencing of TH 1-type chemokines shapes tumour immunity and immunotherapy." *Nature*, 527:7577 (2015): 249-253.
Persic et al., "An integrated vector system for the eukaryotic expression of antibodies or their fragments after selection from phage display libraries," *Gene*, 187:9-19 (1997).
Peterson et al., "Enzymatic cleavage of peptide-linked radiolabels from immunoconjugates," *Bioconjug. Chem.*, 10(4):553-557 (1999).
Pettersen et al., "UCSF Chimera—a visualization system for exploratory research and analysis," *J. Comput. Chem.*, 25(13):1605-1612 (2004).
Pluckthun et al., "Expression of functional antibody Fv and Fab fragments in *Escherichia coli*," *Methods Enzymol.*, 178:497-515 (1989).
Presta, Leonard G. "Antibody engineering." *Current Opinion in Structural Biology* 2.4 (1992): 593-596.
Presta, Leonard G. "Molecular engineering and design of therapeutic antibodies." *Current opinion in immunology* 20.4 (2008): 460-470.
Qin et al., "Interferon-β gene therapy inhibits tumor formation and causes regression of established tumors in immune-deficient mice," *Proc Natl Acad Sci U S A*, 95(24):14411-14416(1998).
Riechmann et al., "Reshaping human antibodies for therapy," *Nature*, 332(6162):323-327 (1988).
Robenek et al., "Butyrophilin controls milk fat globule secretion," *Proc. Natl. Acad. Sci. USA*, 103(27):10385-10390 (2006).
Robert et al., "Efficacy and safety of retreatment with ipilimumab in patients with pretreated advanced melanoma who progressed after initially achieving disease control," *Clin. Cancer Res.*, 19(8):2232-2239 (2013).
Robert et al., "Ipilimumab plus dacarbazine for previously untreated metastatic melanoma," *N. Engl. J. Med.*, 364(26):2517-2526 (2011).
Roguska et al., "Humanization of murine monoclonal antibodies through variable domain resurfacing," *Proc. Natl. Acad. Sci. USA*, 91:969-973 (1994).
Routledge et al., "The effect of aglycosylation on the immunogenicity of a humanized therapeutic CD3 monoclonal antibody," *Transplantation*, 60:847-853 (1995).
Sali et al., "Comparative protein modelling by satisfaction of spatial restraints," *J. Molec. Biol.*, 234:779-815(1993).
Saudek et al., "A preliminary trial of the programmable implantable medication system for insulin delivery," *N.Engl. J. Med.* 321(9):574-579 (1989).
Sawai et al., "Direct production of the Fab fragment derived from the sperm immobilizing antibody using polymerase chain reaction and cDNA expression vectors," *Am. J. Reprod. Immunol.*, 34:26-34 (1995).
Schier et al., "Identification of functional and structural amino-acid residues by parsimonious mutagenesis," *Gene*, 169(2):147-155 (1996).
Schier et al., "Isolation of picomolar affinity anti-c-erbB-2 single-chain Fv by molecular evolution of the complementarity determining regions in the center of the antibody binding site," *J. Mol. Biol.*, 263:551-567 (1996).
Schwarz et al., "Mechanisms and principles of N-linked protein glycosylation," *Curr. Opin. Struct. Biol.*, 21:576-582 (2011).
Sefton, "Inplantable pumps," *CRC Crit. Ref Biomed. Eng.* 14:201-240 (1987).
Senter, "Potent antibody drug conjugates for cancer therapy," *Curr. Opin. Chem. Biol.*, 13(3):235-244 (2009).
Shen et al., "EGFR modulates microRNA maturation in response to hypoxia through phosphorylation of AGO2," *Nature*, 397(7449):383-387 (2013).
Sheppard et al., "PD-1 inhibits T-cell receptor induced phosphorylation of the ZAP70/CD3zeta signalosome and downstream signaling to PKCtheta," *FEBS Lett.*, 574(1-3):37-41 (2004).
Shields et al., "Lack of fucose on human IgG1 N-linked oligosaccharide improves binding to human Fcgamma RIII and antibody-dependent cellular toxicity," *J. Biol. Chem.*, 277:26733-26740 (2002).
Shu et al., "Secretion of a single-gene-encoded immunoglobulin from myeloma cells," *Proc. Natl. Acad. Sci. USA*, 90:7995-7999 (1993).
Skerra et al., "Assembly of a functional immunoglobulin Fv fragment in *Escherichia coli*," *Science*, 240:1038-1041 (1988).
Smith et al., "BTN1A1, the mammary gland butyrophilin, and BTN2A2 are both inhibitors of T cell activation," *J. Immunol.*, 184(7):3514-3525 (2010).
Song et al., "Antibody mediated lung targeting of long-circulating emulsions," *PDA J. Pharm. Sci. Tech.*, 50:372-377 (1996).
Steidl et al., "In vitro affinity maturation of human GM-CSF antibodies by targeted CDR-diversification," *Mol. Immunol.*, 46:135-144 (2008).
Stemmer, "Rapid evolution of a protein in vitro by DNA shuffling," *Nature*, 370(6488):389-391 (1994).
Studnicka et al., "Human-engineered monoclonal antibodies retain full specific binding activity by preserving non-CDR complementarity-modulating residues," *Protein Eng.*, 7:805-814 (1994).
Swann et al., "Considerations for the development of therapeutic monoclonal antibodies," *Curr. Opin. Immunol.*, 20:493-499 (2008).
Takahashi et al., "Human Fas ligand: gene structure, chromosomal location and species specificity," *Int. Immunol.*, 6:1567-1574 (1994).
Tao et al., "Studies of aglycosylated chimeric mouse-human IgG. Role of carbohydrate in the structure and effector functions mediated by the human IgG constant region," *J. Immunol.*, 143:2595-2601 (1989).
Taylor et al., "A transgenic mouse that expresses a diversity of human sequence heavy and light chain immunoglobulins," *Nucleic Acids Res.*, 20:6287-6295 (1992).
Teicher, "Antibody-drug conjugate targets," *Curr. Cancer Drug Targets*, 9(8):982-1004 (2009).
Thorpe et al., "The preparation and cytotoxic properties of antibody-toxin conjugates," *Immunol. Rev.*, 62:119-158 (1982).
Thorpe, "Antibody Carriers of Cytotoxic Agents In Cancer Therapy: A Review", in Monoclonal Antibodies '84: Biological and Clinical Applications, Pinchera et al. (eds.), pp. 475-506 (1985).
Topalian et al., "Safety, activity, and immune correlates of anti-PD-1 antibody in cancer," *N. Engl. J. Med.*, 366(26):2443-2454 (2012).
Torchilin et al., "How do polymers prolong circulation time of liposomes?." *Journal of Liposome Research* 6.1 (1996): 99-116.

(56) References Cited

OTHER PUBLICATIONS

Vigdorovich et al., "Structure and T cell inhibition properties of B7 family member, B7-H3," *Structure*, 21(5):707-717 (2013).

Vingerhoeads et al., "Immunoliposomes in vivo," *Immunomethods*, 4(3):259-272 (1994).

Wall et al., "Modulation of cIAP-1 by novel antitubulin agents when combined with bryostatin 1 results in increased *Apoptosis* in the human early pre-B acute lymphoblastic leukemia cell line Reh," *Biochem. Biophys. Res. Commun.*, 266:76-80 (1999).

Wallick et al., "Glycosylation of a VH residue of a monoclonal antibody against alpha (1—6) dextran increases its affinity for antigen," *J. Exp. Med.*, 168: 1099-1109 (1988).

Watanabe et al., "BTLA is a lymphocyte inhibitory receptor with similarities to CTLA-4 and PD-1," *Nat. Immunol.*, 4(7):670-679 (2003).

Wilson et al., "The structure of an antigenic determinant in a protein," *Cell*, 37:767-778 (1984).

Winn et al., "Overview of the CCP4 suite and current developments," *Acta Crystallogr D. Biol. Crystallogr.*, 67(Pt4):235-242 (2011).

Wohlgemuth et al., Evolutionary optimization of speed and accuracy of decoding on the ribosome, *Philos. Trans. R. Soc. Lond. B. Biol. Sci.*, 366:2979-2986 (2011).

Woyke et al., "Effect of auristatin PHE on microtubule integrity and nuclear localization in Cryptococcus neoformans," *Antimicrob. Agents Chemother.*, 46:3802-3808 (2002).

Woyke et al., "In vitro activities and postantifungal effects of the potent dolastatin 10 derivative auristatin PHE," *Antimcrob. Agents Chemother.*, 45:3580-3584 (2001).

Wu et al., "Receptor-mediated in vitro gene transformation by a soluble DNA carrier system," *J. Biol. Chem.*, 262(10):4429-4432 (1987).

Wu et al., "Stepwise in vitro affinity maturation of Vitaxin, an alphav beta3-specific humanized mAb," *Proc. Natl. Acad. Sci. USA*, 95:6037-6042 (1998).

Yang et al., "PD-L1 : PD-1 interaction contributes to the functional suppression of T-cell responses to human uveal melanoma cells in vitro," *Invest. Ophthalmol. Vis. Sci.*, 49(6):2518-2525 (2008).

Yelton et al., "Affinity maturation of the BR96 anti-carcinoma antibody by codon-based mutagenesis," *J. Immunol.*, 155:1994-2004 (1995).

Zimmermann et al., "A triglycine linker improves tumor uptake and biodistributions of 67-Cu-labeled anti-neuroblastoma MAb chCE7 F (ab') 2 fragments." *Nuclear medicine and biology* 26.8 (1999): 943-950.

\* cited by examiner

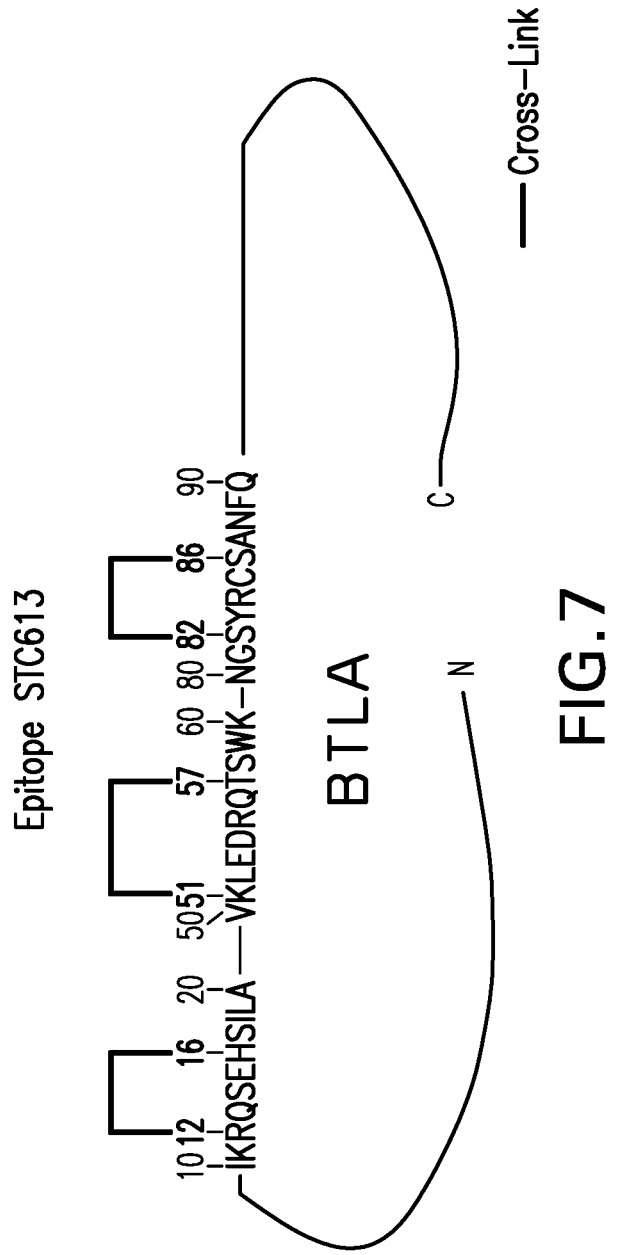

SEQUENCE LISTING

<160> NUMBER OF SEQ ID NOS: 169

<210> SEQ ID NO 1
<211> LENGTH: 289
<212> TYPE: PRT
<213> ORGANISM: Homo sapiens

<400> SEQUENCE: 1

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu

```
                    20                  25                  30
Ser Cys Asp Val Gln Leu Tyr Ile Lys Arg Gln Ser Glu His Ser Ile
                35                  40                  45

Leu Ala Gly Asp Pro Phe Glu Leu Glu Cys Pro Val Lys Tyr Cys Ala
            50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                    85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
                115                 120                 125

Thr Thr Leu Tyr Val Thr Asp Val Lys Ser Ala Ser Glu Arg Pro Ser
            130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
                180                 185                 190

Gly Arg Glu Ile Asn Leu Val Asp Ala His Leu Lys Ser Glu Gln Thr
            195                 200                 205

Glu Ala Ser Thr Arg Gln Asn Ser Gln Val Leu Leu Ser Glu Thr Gly
            210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
                260                 265                 270

Arg Asn Val Lys Glu Ala Pro Thr Glu Tyr Ala Ser Ile Cys Val Arg
            275                 280                 285

Ser

<210> SEQ ID NO 2
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Arg Asp Asp
                20                  25                  30

Tyr Val His Trp Leu Lys Gln Arg Pro Asp Gln Gly Leu Glu Trp Ile
                35                  40                  45

Gly Arg Ile Asp Pro Ala Asn Gly Lys Thr Lys Tyr Asp Pro Lys Phe
            50                  55                  60

Gln Asp Lys Ala Thr Ile Thr Ala Asp Thr Ser Ser Asn Thr Ala Tyr
65                  70                  75                  80
```

```
Leu Gln Leu Ser Ser Leu Thr Ser Glu Asp Thr Ala Val Tyr Phe Cys
            85                  90                  95

Val Arg Glu Gly Gly Ser Asn Tyr Asp Tyr Ala Met Asp Tyr Trp Gly
            100                 105                 110

Gln Gly Thr Ser Val Thr Val Ser Ser
            115                 120

<210> SEQ ID NO 3
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
gaggttcagc tgcagcagtc tggggctgag cttgtgaggc caggggcctc agtcaagttg      60
tcctgcacag cttctggctt aacattaga gacgactatg tgcactggtt gaaacagagg     120
cctgatcagg gcctggagtg gattggaagg attgatcctg cgaatggtaa aactaaatat     180
gacccgaagt tccaggacaa ggccactata actgcagaca catcctccaa cacagcctac     240
ctgcagctca gcagcctgac atctgaggac actgccgtct atttctgtgt tagagagggg     300
ggtagtaact acgactatgc tatggactac tggggtcaag gaacctcagt caccgtctcc     360
tca                                                                   363

<210> SEQ ID NO 4
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Ser Leu Ser Leu Leu Asp Ser
            20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Ile His Phe Pro Arg Thr Phe Gly Gly Gly Thr Lys Leu Glu Ile Lys
            100                 105                 110

<210> SEQ ID NO 5
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
```

-continued

```
gatgttgtga tgacccagac tccactcact ttgtcggtta ccattggaca accagcctcc    60
atctcttgca agtcaagtct gagcctctta gatagtgatg gaaagacata tttgaattgg   120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tgtgggagtt tattattgct ggcaaggtat tcatttctcct  300 cggacgttcg gtggaggcac caagctggaa atcaaa                             336
```

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Gly Phe Asn Ile Arg Asp Asp
1               5

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Asp Pro Ala Asn Gly Lys
1               5

<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Glu Gly Gly Ser Asn Tyr Asp Tyr Ala Met Asp Tyr
1               5                   10

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Gly Phe Asn Ile Arg Asp Asp Tyr Val His
1               5                   10

<210> SEQ ID NO 10
<211> LENGTH: 10
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 10

Arg Ile Asp Pro Ala Asn Gly Lys Thr Lys
1               5                   10

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Glu Gly Gly Ser Asn Tyr Asp Tyr Ala Met Asp Tyr
1               5                   10

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Asp Tyr Val His
1               5

<210> SEQ ID NO 13
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Ile Asp Pro Ala Asn Gly Lys Thr Lys Tyr Asp Pro Lys Phe Gln
1               5                   10                  15

Asp

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Glu Gly Gly Ser Asn Tyr Asp Tyr Ala Met Asp Tyr
1               5                   10

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

```
            Synthetic peptide"

<400> SEQUENCE: 15

Arg Asp Asp Tyr Val His
1               5

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Trp Ile Gly Arg Ile Asp Pro Ala Asn Gly Lys Thr Lys
1               5                  10

<210> SEQ ID NO 17
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Val Arg Glu Gly Gly Ser Asn Tyr Asp Tyr Ala Met Asp
1               5                  10

<210> SEQ ID NO 18
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Ser Ser Leu Ser Leu Leu Asp Ser Asp Gly Lys Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Leu Val Ser Lys Leu Asp Ser
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20
```

```
Trp Gln Gly Ile His Phe Pro Arg Thr
1               5

<210> SEQ ID NO 21
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Lys Ser Ser Leu Ser Leu Leu Asp Ser Asp Gly Lys Thr Tyr Leu Asn
1               5                   10                  15

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Val Ser Lys Leu Asp Ser
1               5

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Gln Gly Ile His Phe Pro Arg Thr
1               5

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Lys Ser Ser Leu Ser Leu Leu Asp Ser Asp Gly Lys Thr Tyr Leu Asn
1               5                   10                  15

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Leu Val Ser Lys Leu Asp Ser
1               5
```

```
<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Trp Gln Gly Ile His Phe Pro Arg Thr
1               5

<210> SEQ ID NO 27
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Leu Asp Ser Asp Gly Lys Thr Tyr Leu Asn Trp Leu
1               5                   10

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Arg Leu Ile Tyr Leu Val Ser Lys Leu Asp
1               5                   10

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Trp Gln Gly Ile His Phe Pro Arg
1               5

<210> SEQ ID NO 30
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45
```

Gly Trp Ile Asn Thr Asn Thr Gly Glu Pro Thr Tyr Ala Glu Glu Phe
            50                  55                  60

Lys Gly Arg Ile Ala Phe Ser Leu Glu Ser Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Glu Gly Val Arg Arg Gly Gly Tyr Phe Phe Asp Tyr Trp Gly
            100                 105                 110

Gln Gly Thr Thr Leu Thr Val Ser Ser
            115                 120

<210> SEQ ID NO 31
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacca acactggaga gccaacatat     180
gctgaagagt tcaagggacg gattgccttc tctttggaat cctctgccag cactgcctat     240
ttgcagatca caaccctcaa aaatgaggac acggccacat atttctgtgc aagagaggga     300
gtgcgacggg gggggtactt ttttgactac tggggccaag gcaccactct cacagtctcc     360
tca                                                                    363

<210> SEQ ID NO 32
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
             20                  25                  30

Leu Ala Trp Tyr Gln Gln Lys Gln Gly Lys Ser Pro Gln Leu Leu Val
         35                  40                  45

Tyr Ala Ala Thr Asn Leu Ala Asp Gly Val Pro Ser Arg Phe Ser Gly
     50                  55                  60

Ser Gly Ser Gly Thr Gln Tyr Ser Leu Lys Ile Asn Ser Leu Gln Ser
 65                  70                  75                  80

Glu Asp Phe Gly Ser Tyr His Cys Gln His Phe Trp Gly Phe Pro Phe
                 85                  90                  95

Thr Phe Gly Ala Gly Thr Lys Leu Glu Ile Lys Arg Ala
            100                 105

<210> SEQ ID NO 33
<211> LENGTH: 327
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
gacatccaga tgactcagtc tccagcctcc ctatctgtat ctgtgggaga aactgtcacc    60
atcacatgtc gagcaagtga gaatatttac agcaatttag catggtatca gcagaaacag   120
ggaaaatctc ctcagctcct ggtctatgct gcaacaaact tagcagatgg tgtgccatca   180
aggttcagtg gcagtggatc aggcacacag tattccctca agatcaacag cctgcagtct   240
gaagattttg ggagttatca ctgtcaacat ttttggggtt ttccattcac gttcggcgcg   300
gggacaaagt tggaaataaa acgggct                                       327

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Tyr Thr Phe Thr Asn Tyr
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Asn Thr Asn Thr Gly Glu
1               5

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Glu Gly Val Arg Arg Gly Gly Tyr Phe Phe Asp Tyr
1               5                   10

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Tyr Thr Phe Thr Asn Tyr Gly Met Asn
1               5                   10

```
<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Trp Ile Asn Thr Asn Thr Gly Glu Pro Thr
1               5                   10

<210> SEQ ID NO 39
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Glu Gly Val Arg Arg Gly Gly Tyr Phe Phe Asp Tyr
1               5                   10

<210> SEQ ID NO 40
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asn Tyr Gly Met Asn
1               5

<210> SEQ ID NO 41
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Trp Ile Asn Thr Asn Thr Gly Glu Pro Thr Tyr Ala Glu Glu Phe Lys
1               5                   10                  15

Gly

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Glu Gly Val Arg Arg Gly Gly Tyr Phe Phe Asp Tyr
1               5                   10
```

-continued

```
<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Thr Asn Tyr Gly Met Asn
1               5

<210> SEQ ID NO 44
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Met Gly Trp Ile Asn Thr Asn Thr Gly Glu Pro Thr
1               5                   10

<210> SEQ ID NO 45
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Arg Glu Gly Val Arg Arg Gly Gly Tyr Phe Phe Asp
1               5                   10

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Ala Ser Glu Asn Ile Tyr Ser Asn Leu Ala
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Ala Thr Asn Leu Ala Asp
1               5

<210> SEQ ID NO 48
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 48

Gln His Phe Trp Gly Phe Pro Phe Thr
1               5

<210> SEQ ID NO 49
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Ala Ser Glu Asn Ile Tyr Ser Asn Leu Ala
1               5                   10

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Ala Thr Asn Leu Ala Asp
1               5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln His Phe Trp Gly Phe Pro Phe Thr
1               5

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Ala Ser Glu Asn Ile Tyr Ser Asn Leu Ala
1               5                   10

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 53

Ala Ala Thr Asn Leu Ala Asp
1               5

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln His Phe Trp Gly Phe Pro Phe Thr
1               5

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Tyr Ser Asn Leu Ala Trp Tyr
1               5

<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Leu Leu Val Tyr Ala Ala Thr Asn Leu Ala
1               5                   10

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln His Phe Trp Gly Phe Pro Phe
1               5

<210> SEQ ID NO 58
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Val Gln Leu Gln Gln Ser Gly Ala Glu Leu Val Lys Pro Gly Ala
```

```
                1               5                   10                  15
            Ser Val Lys Leu Ser Cys Thr Ala Ser Gly Phe Asn Ile Lys Asp Thr
                            20                  25                  30

Tyr Met His Trp Val Arg Gln Arg Pro Glu Gln Gly Leu Glu Trp Ile
                        35                  40                  45

Gly Arg Ile Asp Pro Ala Asn Gly Tyr Thr Lys Tyr Asp Pro Lys Phe
                    50                  55                  60

Gln Gly Lys Ala Thr Ile Thr Ala Asp Thr Ser Ser Asn Thr Ala Tyr
            65                  70                  75                  80

Leu Gln Leu Ser Ser Leu Thr Ser Glu Asp Thr Ala Val Tyr Tyr Cys
                            85                  90                  95

Leu Ile Tyr Asp Gly Tyr Tyr Asp Ser Phe Asp Tyr Trp Gly Gln Gly
                            100                 105                 110

Thr Thr Leu Thr Val Ser Ser
                        115

<210> SEQ ID NO 59
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
gaggttcagc tgcagcagtc tggggcagag cttgtgaagc caggggcctc agtcaagttg        60
tcctgcacag cttctggctt caacattaaa gacacctata tgcactgggt gaggcagagg       120
cctgaacagg gcctggagtg gattggaagg attgatcctg cgaatggtta tactaaatat       180
gacccgaagt tccagggcaa ggccactata acagcagaca tcctccaa cacagcctac        240 ctgcagctca gcagcctgac atctgaggac actgccgtct attactgtct catctatgat       300
ggttactacg actcctttga ctactggggc caaggcacca ctctcacagt ctcctca          357

<210> SEQ ID NO 60
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Asp Val Val Met Thr Gln Thr Pro Leu Thr Leu Ser Val Pro Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Val
                85                  90                  95

Thr His Phe Pro Arg Thr Phe Gly Gly Gly Thr Lys Leu Glu Ile Lys
                100                 105                 110
```

<210> SEQ ID NO 61
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
gatgttgtga tgacccagac tccactcact ttgtcggttc ccattggaca accagcctcc      60
atctcttgca agtcaagtca gagcctctta gatagtgatg aaagacata tttgaattgg      120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaagttac acattttcct    300
cggacgttcg gtggaggcac caagctggaa atcaaa                                336
```

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

Gly Phe Asn Ile Lys Asp Thr
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Asp Pro Ala Asn Gly Tyr
1               5

<210> SEQ ID NO 64
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Tyr Asp Gly Tyr Tyr Asp Ser Phe Asp Tyr
1               5                   10

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 65

Gly Phe Asn Ile Lys Asp Thr Tyr Met His
1               5                   10

<210> SEQ ID NO 66
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Arg Ile Asp Pro Ala Asn Gly Tyr Thr Lys
1               5                   10

<210> SEQ ID NO 67
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Tyr Asp Gly Tyr Tyr Asp Ser Phe Asp Tyr
1               5                   10

<210> SEQ ID NO 68
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Thr Tyr Met His
1               5

<210> SEQ ID NO 69
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Arg Ile Asp Pro Ala Asn Gly Tyr Thr Lys Tyr Asp Pro Lys Phe Gln
1               5                   10                  15

Gly

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70
```

```
Tyr Asp Gly Tyr Tyr Asp Ser Phe Asp Tyr
1               5                   10

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Lys Asp Thr Tyr Met His
1               5

<210> SEQ ID NO 72
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Trp Ile Gly Arg Ile Asp Pro Ala Asn Gly Tyr Thr Lys
1               5                   10

<210> SEQ ID NO 73
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Leu Ile Tyr Asp Gly Tyr Tyr Asp Ser Phe Asp
1               5                   10

<210> SEQ ID NO 74
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Lys Ser Ser Gln Ser Leu Leu Asp Ser Asp Gly Lys Thr Tyr Leu Asn
1               5                   10                  15

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Leu Val Ser Lys Leu Asp Ser
1               5
```

```
<210> SEQ ID NO 76
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Trp Gln Val Thr His Phe Pro Arg Thr
1               5

<210> SEQ ID NO 77
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Lys Ser Ser Gln Ser Leu Leu Asp Ser Asp Gly Lys Thr Tyr Leu Asn
1               5                   10                  15

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Leu Val Ser Lys Leu Asp Ser
1               5

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Trp Gln Val Thr His Phe Pro Arg Thr
1               5

<210> SEQ ID NO 80
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Lys Ser Ser Gln Ser Leu Leu Asp Ser Asp Gly Lys Thr Tyr Leu Asn
1               5                   10                  15

<210> SEQ ID NO 81
<211> LENGTH: 7
<212> TYPE: PRT
```

-continued

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Leu Val Ser Lys Leu Asp Ser
1               5

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Trp Gln Val Thr His Phe Pro Arg Thr
1               5

<210> SEQ ID NO 83
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Leu Asp Ser Asp Gly Lys Thr Tyr Leu Asn Trp Leu
1               5                   10

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Arg Leu Ile Tyr Leu Val Ser Lys Leu Asp
1               5                   10

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Trp Gln Val Thr His Phe Pro Arg
1               5

<210> SEQ ID NO 86
<211> LENGTH: 128
<212> TYPE: PRT
<213> ORGANISM: Homo sapiens

<400> SEQUENCE: 86

-continued

```
Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
            20                  25                  30

Cys Ala Asn Arg Pro His Val Thr Trp Cys Lys Leu Asn Gly Thr Thr
        35                  40                  45

Cys Val Lys Leu Glu Asp Arg Gln Thr Ser Trp Lys Glu Glu Lys Asn
    50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
            85                  90                  95

His Ser Thr Thr Leu Tyr Val Thr Gly Lys Gln Asn Glu Leu Ser Asp
            100                 105                 110

Thr Ala Gly Arg Glu Ile Asn Leu Val Asp His His His His His His
            115                 120                 125
```

<210> SEQ ID NO 87
<211> LENGTH: 11
<212> TYPE: PRT
<213> ORGANISM: Homo sapiens

<400> SEQUENCE: 87

```
Lys Glu Ser Cys Asp Val Gln Leu Tyr Ile Lys
1               5                   10
```

<210> SEQ ID NO 88
<211> LENGTH: 11
<212> TYPE: PRT
<213> ORGANISM: Homo sapiens

<400> SEQUENCE: 88

```
Lys Glu Ser Cys Asp Val Gln Leu Tyr Ile Lys
1               5                   10
```

<210> SEQ ID NO 89
<211> LENGTH: 12
<212> TYPE: PRT
<213> ORGANISM: Homo sapiens

<400> SEQUENCE: 89

```
Lys Glu Ser Cys Asp Val Gln Leu Tyr Ile Lys Arg
1               5                   10
```

<210> SEQ ID NO 90
<211> LENGTH: 12
<212> TYPE: PRT
<213> ORGANISM: Homo sapiens

<400> SEQUENCE: 90

```
Lys Glu Ser Cys Asp Val Gln Leu Tyr Ile Lys Arg
1               5                   10
```

<210> SEQ ID NO 91
<211> LENGTH: 11
<212> TYPE: PRT
<213> ORGANISM: Homo sapiens

<400> SEQUENCE: 91

```
Glu Ser Cys Asp Val Gln Leu Tyr Ile Lys Arg
1               5                   10
```

-continued

<210> SEQ ID NO 92
<211> LENGTH: 32
<212> TYPE: PRT
<213> ORGANISM: Homo sapiens

<400> SEQUENCE: 92

Arg Gln Ser Glu His Ser Ile Leu Ala Gly Asp Pro Phe Glu Leu Glu
1               5                   10                  15

Cys Pro Val Lys Tyr Cys Ala Asn Arg Pro His Val Thr Trp Cys Lys
            20                  25                  30

<210> SEQ ID NO 93
<211> LENGTH: 20
<212> TYPE: PRT
<213> ORGANISM: Homo sapiens

<400> SEQUENCE: 93

Arg Gln Ser Glu His Ser Ile Leu Ala Gly Asp Pro Phe Glu Leu Glu
1               5                   10                  15

Cys Pro Val Lys
            20

<210> SEQ ID NO 94
<211> LENGTH: 20
<212> TYPE: PRT
<213> ORGANISM: Homo sapiens

<400> SEQUENCE: 94

Arg Gln Ser Glu His Ser Ile Leu Ala Gly Asp Pro Phe Glu Leu Glu
1               5                   10                  15

Cys Pro Val Lys
            20

<210> SEQ ID NO 95
<211> LENGTH: 19
<212> TYPE: PRT
<213> ORGANISM: Homo sapiens

<400> SEQUENCE: 95

Gln Ser Glu His Ser Ile Leu Ala Gly Asp Pro Phe Glu Leu Glu Cys
1               5                   10                  15

Pro Val Lys

<210> SEQ ID NO 96
<211> LENGTH: 19
<212> TYPE: PRT
<213> ORGANISM: Homo sapiens

<400> SEQUENCE: 96

Gln Ser Glu His Ser Ile Leu Ala Gly Asp Pro Phe Glu Leu Glu Cys
1               5                   10                  15

Pro Val Lys

<210> SEQ ID NO 97
<211> LENGTH: 31
<212> TYPE: PRT
<213> ORGANISM: Homo sapiens

<400> SEQUENCE: 97

Gln Ser Glu His Ser Ile Leu Ala Gly Asp Pro Phe Glu Leu Glu Cys
1               5                   10                  15

```
Pro Val Lys Tyr Cys Ala Asn Arg Pro His Val Thr Trp Cys Lys
            20                  25                  30
```

<210> SEQ ID NO 98
<211> LENGTH: 12
<212> TYPE: PRT
<213> ORGANISM: Homo sapiens

<400> SEQUENCE: 98

```
Tyr Cys Ala Asn Arg Pro His Val Thr Trp Cys Lys
1               5                   10
```

<210> SEQ ID NO 99
<211> LENGTH: 21
<212> TYPE: PRT
<213> ORGANISM: Homo sapiens

<400> SEQUENCE: 99

```
Asn Ile Ser Phe Phe Ile Leu His Phe Glu Pro Val Leu Pro Asn Asp
1               5                   10                  15

Asn Gly Ser Tyr Arg
            20
```

<210> SEQ ID NO 100
<211> LENGTH: 22
<212> TYPE: PRT
<213> ORGANISM: Homo sapiens

<400> SEQUENCE: 100

```
Cys Ser Ala Asn Phe Gln Ser Asn Leu Ile Glu Ser His Ser Thr Thr
1               5                   10                  15

Leu Tyr Val Thr Gly Lys
            20
```

<210> SEQ ID NO 101
<211> LENGTH: 10
<212> TYPE: PRT
<213> ORGANISM: Homo sapiens

<400> SEQUENCE: 101

```
Gln Asn Glu Leu Ser Asp Thr Ala Gly Arg
1               5                   10
```

<210> SEQ ID NO 102
<211> LENGTH: 12
<212> TYPE: PRT
<213> ORGANISM: Homo sapiens

<400> SEQUENCE: 102

```
Glu Ile Asn Leu Val Asp His His His His His His
1               5                   10
```

<210> SEQ ID NO 103
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Cys(carbamidomethyl)

<400> SEQUENCE: 103

```
Lys Glu Ser Cys Asp Val Gln Leu
1               5
```

-continued

```
<210> SEQ ID NO 104
<211> LENGTH: 8
<212> TYPE: PRT
<213> ORGANISM: Homo sapiens

<400> SEQUENCE: 104

Lys Glu Ser Cys Asp Val Gln Leu
1               5

<210> SEQ ID NO 105
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Cys(carbamidomethyl)

<400> SEQUENCE: 105

Lys Glu Ser Cys Asp Val Gln Leu Tyr
1               5

<210> SEQ ID NO 106
<211> LENGTH: 10
<212> TYPE: PRT
<213> ORGANISM: Homo sapiens

<400> SEQUENCE: 106

Ile Lys Arg Gln Ser Glu His Ser Ile Leu
1               5                   10

<210> SEQ ID NO 107
<211> LENGTH: 15
<212> TYPE: PRT
<213> ORGANISM: Homo sapiens

<400> SEQUENCE: 107

Ile Lys Arg Gln Ser Glu His Ser Ile Leu Ala Gly Asp Pro Phe
1               5                   10                  15

<210> SEQ ID NO 108
<211> LENGTH: 8
<212> TYPE: PRT
<213> ORGANISM: Homo sapiens

<400> SEQUENCE: 108

Glu Leu Glu Cys Pro Val Lys Tyr
1               5

<210> SEQ ID NO 109
<211> LENGTH: 17
<212> TYPE: PRT
<213> ORGANISM: Homo sapiens

<400> SEQUENCE: 109

Ile Lys Arg Gln Ser Glu His Ser Ile Leu Ala Gly Asp Pro Phe Glu
1               5                   10                  15

Leu

<210> SEQ ID NO 110
<211> LENGTH: 13
<212> TYPE: PRT
<213> ORGANISM: Homo sapiens
<220> FEATURE:
<221> NAME/KEY: MOD_RES
```

```
<222> LOCATION: (9)..(9)
<223> OTHER INFORMATION: Cys(carbamidomethyl)

<400> SEQUENCE: 110

Ala Gly Asp Pro Phe Glu Leu Glu Cys Pro Val Lys Tyr
1               5                   10

<210> SEQ ID NO 111
<211> LENGTH: 9
<212> TYPE: PRT
<213> ORGANISM: Homo sapiens

<400> SEQUENCE: 111

Cys Ala Asn Arg Pro His Val Thr Trp
1               5

<210> SEQ ID NO 112
<211> LENGTH: 9
<212> TYPE: PRT
<213> ORGANISM: Homo sapiens

<400> SEQUENCE: 112

Lys Glu Ser Cys Asp Val Gln Leu Tyr
1               5

<210> SEQ ID NO 113
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Cys(carbamidomethyl)
<220> FEATURE:
<221> NAME/KEY: MOD_RES
<222> LOCATION: (4)..(4)
<223> OTHER INFORMATION: Asn(Deamidated)
<220> FEATURE:
<221> NAME/KEY: MOD_RES
<222> LOCATION: (8)..(8)
<223> OTHER INFORMATION: Cys(carbamidomethyl)

<400> SEQUENCE: 113

Cys Lys Leu Asn Gly Thr Thr Cys Val Lys Leu Glu Asp Arg Gln Thr
1               5                   10                  15

Ser Trp

<210> SEQ ID NO 114
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Cys(carbamidomethyl)
<220> FEATURE:
<221> NAME/KEY: MOD_RES
<222> LOCATION: (8)..(8)
<223> OTHER INFORMATION: Cys(carbamidomethyl)

<400> SEQUENCE: 114

Cys Lys Leu Asn Gly Thr Thr Cys Val Lys Leu Glu Asp Arg Gln Thr
1               5                   10                  15

Ser Trp

<210> SEQ ID NO 115
<211> LENGTH: 15
```

```
<212> TYPE: PRT
<213> ORGANISM: Homo sapiens

<400> SEQUENCE: 115

Asn Gly Thr Thr Cys Val Lys Leu Glu Asp Arg Gln Thr Ser Trp
1               5                   10                  15

<210> SEQ ID NO 116
<211> LENGTH: 9
<212> TYPE: PRT
<213> ORGANISM: Homo sapiens

<400> SEQUENCE: 116

Ile Glu Ser His Ser Thr Thr Leu Tyr
1               5

<210> SEQ ID NO 117
<211> LENGTH: 9
<212> TYPE: PRT
<213> ORGANISM: Homo sapiens

<400> SEQUENCE: 117

Lys Glu Glu Lys Asn Ile Ser Phe Phe
1               5

<210> SEQ ID NO 118
<211> LENGTH: 9
<212> TYPE: PRT
<213> ORGANISM: Homo sapiens

<400> SEQUENCE: 118

Lys Glu Ser Cys Asp Val Gln Leu Tyr
1               5

<210> SEQ ID NO 119
<211> LENGTH: 17
<212> TYPE: PRT
<213> ORGANISM: Homo sapiens

<400> SEQUENCE: 119

Glu Pro Val Leu Pro Asn Asp Asn Gly Ser Tyr Arg Cys Ser Ala Asn
1               5                   10                  15

Phe

<210> SEQ ID NO 120
<211> LENGTH: 8
<212> TYPE: PRT
<213> ORGANISM: Homo sapiens

<400> SEQUENCE: 120

Val Thr Gly Lys Gln Asn Glu Leu
1               5

<210> SEQ ID NO 121
<211> LENGTH: 10
<212> TYPE: PRT
<213> ORGANISM: Homo sapiens

<400> SEQUENCE: 121

Arg Cys Ser Ala Asn Phe Gln Ser Asn Leu
1               5                   10

<210> SEQ ID NO 122
<211> LENGTH: 8
```

```
<212> TYPE: PRT
<213> ORGANISM: Homo sapiens

<400> SEQUENCE: 122

Asn Gly Thr Thr Cys Val Lys Leu
1               5

<210> SEQ ID NO 123
<211> LENGTH: 12
<212> TYPE: PRT
<213> ORGANISM: Homo sapiens

<400> SEQUENCE: 123

Gln Ser Asn Leu Ile Glu Ser His Ser Thr Thr Leu
1               5                   10

<210> SEQ ID NO 124
<211> LENGTH: 8
<212> TYPE: PRT
<213> ORGANISM: Homo sapiens

<400> SEQUENCE: 124

Lys Glu Glu Lys Asn Ile Ser Phe
1               5

<210> SEQ ID NO 125
<211> LENGTH: 13
<212> TYPE: PRT
<213> ORGANISM: Homo sapiens

<400> SEQUENCE: 125

Gln Ser Asn Leu Ile Glu Ser His Ser Thr Thr Leu Tyr
1               5                   10

<210> SEQ ID NO 126
<211> LENGTH: 9
<212> TYPE: PRT
<213> ORGANISM: Homo sapiens

<400> SEQUENCE: 126

Ile Glu Ser His Ser Thr Thr Leu Tyr
1               5

<210> SEQ ID NO 127
<211> LENGTH: 8
<212> TYPE: PRT
<213> ORGANISM: Homo sapiens

<400> SEQUENCE: 127

Glu Leu Glu Cys Pro Val Lys Tyr
1               5

<210> SEQ ID NO 128
<211> LENGTH: 18
<212> TYPE: PRT
<213> ORGANISM: Homo sapiens

<400> SEQUENCE: 128

Val Thr Gly Lys Gln Asn Glu Leu Ser Asp Thr Ala Gly Arg Glu Ile
1               5                   10                  15

Asn Leu

<210> SEQ ID NO 129
<211> LENGTH: 9
```

```
<212> TYPE: PRT
<213> ORGANISM: Homo sapiens

<400> SEQUENCE: 129

Cys Ala Asn Arg Pro His Val Thr Trp
1               5

<210> SEQ ID NO 130
<211> LENGTH: 6
<212> TYPE: PRT
<213> ORGANISM: Homo sapiens

<400> SEQUENCE: 130

Glu Cys Pro Val Lys Tyr
1               5

<210> SEQ ID NO 131
<211> LENGTH: 8
<212> TYPE: PRT
<213> ORGANISM: Homo sapiens

<400> SEQUENCE: 131

Glu Leu Glu Cys Pro Val Lys Tyr
1               5

<210> SEQ ID NO 132
<211> LENGTH: 8
<212> TYPE: PRT
<213> ORGANISM: Homo sapiens

<400> SEQUENCE: 132

Val Asp His His His His His His
1               5

<210> SEQ ID NO 133
<211> LENGTH: 26
<212> TYPE: PRT
<213> ORGANISM: Homo sapiens

<400> SEQUENCE: 133

Val Thr Gly Lys Gln Asn Glu Leu Ser Asp Thr Ala Gly Arg Glu Ile
1               5                   10                  15

Asn Leu Val Asp His His His His His His
            20                  25

<210> SEQ ID NO 134
<211> LENGTH: 26
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Asn(Deamidated)

<400> SEQUENCE: 134

Val Thr Gly Lys Gln Asn Glu Leu Ser Asp Thr Ala Gly Arg Glu Ile
1               5                   10                  15

Asn Leu Val Asp His His His His His His
            20                  25

<210> SEQ ID NO 135
<211> LENGTH: 10
<212> TYPE: PRT
<213> ORGANISM: Homo sapiens
```

```
<400> SEQUENCE: 135

Ser Asp Thr Ala Gly Arg Glu Ile Asn Leu
1               5                   10

<210> SEQ ID NO 136
<211> LENGTH: 9
<212> TYPE: PRT
<213> ORGANISM: Homo sapiens

<400> SEQUENCE: 136

Lys Glu Ser Cys Asp Val Gln Leu Tyr
1               5

<210> SEQ ID NO 137
<211> LENGTH: 18
<212> TYPE: PRT
<213> ORGANISM: Homo sapiens

<400> SEQUENCE: 137

Ser Asp Thr Ala Gly Arg Glu Ile Asn Leu Val Asp His His His His
1               5                   10                  15

His His

<210> SEQ ID NO 138
<211> LENGTH: 7
<212> TYPE: PRT
<213> ORGANISM: Homo sapiens

<400> SEQUENCE: 138

Glu Asp Arg Gln Thr Ser Trp
1               5

<210> SEQ ID NO 139
<211> LENGTH: 8
<212> TYPE: PRT
<213> ORGANISM: Homo sapiens

<400> SEQUENCE: 139

Val Thr Gly Lys Gln Asn Glu Leu
1               5

<210> SEQ ID NO 140
<211> LENGTH: 9
<212> TYPE: PRT
<213> ORGANISM: Homo sapiens

<400> SEQUENCE: 140

Tyr Val Thr Gly Lys Gln Asn Glu Leu
1               5

<210> SEQ ID NO 141
<211> LENGTH: 17
<212> TYPE: PRT
<213> ORGANISM: Homo sapiens

<400> SEQUENCE: 141

Asp Val Gln Leu Tyr Ile Lys Arg Gln Ser Glu His Ser Ile Leu Ala
1               5                   10                  15

Gly

<210> SEQ ID NO 142
<211> LENGTH: 17
<212> TYPE: PRT
```

<213> ORGANISM: Homo sapiens

<400> SEQUENCE: 142

Asp Thr Ala Gly Arg Glu Ile Asn Leu Val Asp His His His His
1               5                   10                  15
His

<210> SEQ ID NO 143
<211> LENGTH: 9
<212> TYPE: PRT
<213> ORGANISM: Homo sapiens

<400> SEQUENCE: 143

Lys Tyr Cys Ala Asn Arg Pro His Val
1               5

<210> SEQ ID NO 144
<211> LENGTH: 10
<212> TYPE: PRT
<213> ORGANISM: Homo sapiens

<400> SEQUENCE: 144

Asn Arg Pro His Val Thr Trp Cys Lys Leu
1               5                   10

<210> SEQ ID NO 145
<211> LENGTH: 5
<212> TYPE: PRT
<213> ORGANISM: Homo sapiens

<400> SEQUENCE: 145

Lys Gln Asn Glu Leu
1               5

<210> SEQ ID NO 146
<211> LENGTH: 10
<212> TYPE: PRT
<213> ORGANISM: Homo sapiens

<400> SEQUENCE: 146

Leu Tyr Ile Lys Arg Gln Ser Glu His Ser
1               5                   10

<210> SEQ ID NO 147
<211> LENGTH: 8
<212> TYPE: PRT
<213> ORGANISM: Homo sapiens

<400> SEQUENCE: 147

Leu Ile Glu Ser His Ser Thr Thr
1               5

<210> SEQ ID NO 148
<211> LENGTH: 8
<212> TYPE: PRT
<213> ORGANISM: Homo sapiens

<400> SEQUENCE: 148

Ile Lys Arg Gln Ser Glu His Ser
1               5

<210> SEQ ID NO 149
<211> LENGTH: 7
<212> TYPE: PRT

<213> ORGANISM: Homo sapiens

<400> SEQUENCE: 149

Lys Glu Ser Cys Asp Val Gln
1               5

<210> SEQ ID NO 150
<211> LENGTH: 7
<212> TYPE: PRT
<213> ORGANISM: Homo sapiens

<400> SEQUENCE: 150

Val Thr Gly Lys Gln Asn Glu
1               5

<210> SEQ ID NO 151
<211> LENGTH: 9
<212> TYPE: PRT
<213> ORGANISM: Homo sapiens

<400> SEQUENCE: 151

Ile Lys Arg Gln Ser Glu His Ser Ile
1               5

<210> SEQ ID NO 152
<211> LENGTH: 9
<212> TYPE: PRT
<213> ORGANISM: Homo sapiens

<400> SEQUENCE: 152

Val Lys Tyr Cys Ala Asn Arg Pro His
1               5

<210> SEQ ID NO 153
<211> LENGTH: 10
<212> TYPE: PRT
<213> ORGANISM: Homo sapiens

<400> SEQUENCE: 153

Ala Asn Arg Pro His Val Thr Trp Cys Lys
1               5                   10

<210> SEQ ID NO 154
<211> LENGTH: 15
<212> TYPE: PRT
<213> ORGANISM: Homo sapiens

<400> SEQUENCE: 154

Val Lys Leu Glu Asp Arg Gln Thr Ser Trp Lys Glu Lys Asn
1               5                   10                  15

<210> SEQ ID NO 155
<211> LENGTH: 9
<212> TYPE: PRT
<213> ORGANISM: Homo sapiens

<400> SEQUENCE: 155

Ile Glu Ser His Ser Thr Thr Leu Tyr
1               5

<210> SEQ ID NO 156
<211> LENGTH: 9
<212> TYPE: PRT
<213> ORGANISM: Mus sp.

```
<400> SEQUENCE: 156

Ser Cys Ala Ala Ser Gly Phe Thr Phe
1               5

<210> SEQ ID NO 157
<211> LENGTH: 18
<212> TYPE: PRT
<213> ORGANISM: Mus sp.

<400> SEQUENCE: 157

Ser Val Thr Ile Gly Gln Pro Ala Ser Ile Ser Cys Lys Ser Ser Leu
1               5                   10                  15

Ser Leu

<210> SEQ ID NO 158
<211> LENGTH: 16
<212> TYPE: PRT
<213> ORGANISM: Mus sp.

<400> SEQUENCE: 158

Thr Leu Lys Ile Ser Arg Val Glu Ala Glu Asp Val Gly Val Tyr Tyr
1               5                   10                  15

<210> SEQ ID NO 159
<211> LENGTH: 14
<212> TYPE: PRT
<213> ORGANISM: Mus sp.

<400> SEQUENCE: 159

Lys Ile Ser Arg Val Glu Ala Glu Asp Val Gly Val Tyr Tyr
1               5                   10

<210> SEQ ID NO 160
<211> LENGTH: 9
<212> TYPE: PRT
<213> ORGANISM: Mus sp.

<400> SEQUENCE: 160

Ile Ser Cys Lys Ser Ser Leu Ser Leu
1               5

<210> SEQ ID NO 161
<211> LENGTH: 11
<212> TYPE: PRT
<213> ORGANISM: Homo sapiens

<400> SEQUENCE: 161

Tyr Ile Lys Arg Gln Ser Glu His Ser Ile Leu
1               5                   10

<210> SEQ ID NO 162
<211> LENGTH: 7
<212> TYPE: PRT
<213> ORGANISM: Homo sapiens

<400> SEQUENCE: 162

Glu Asp Arg Gln Thr Ser Trp
1               5

<210> SEQ ID NO 163
<211> LENGTH: 10
<212> TYPE: PRT
<213> ORGANISM: Homo sapiens
```

```
<400> SEQUENCE: 163

Arg Cys Ser Ala Asn Phe Gln Ser Asn Leu
1               5                   10

<210> SEQ ID NO 164
<211> LENGTH: 8
<212> TYPE: PRT
<213> ORGANISM: Homo sapiens

<400> SEQUENCE: 164

Asn Gly Thr Thr Cys Val Lys Leu
1               5

<210> SEQ ID NO 165
<211> LENGTH: 11
<212> TYPE: PRT
<213> ORGANISM: Homo sapiens

<400> SEQUENCE: 165

Glu Pro Val Leu Pro Asn Asp Asn Gly Ser Tyr
1               5                   10

<210> SEQ ID NO 166
<211> LENGTH: 11
<212> TYPE: PRT
<213> ORGANISM: Homo sapiens

<400> SEQUENCE: 166

Leu Tyr Ile Lys Arg Gln Ser Glu His Ser Ile
1               5                   10

<210> SEQ ID NO 167
<211> LENGTH: 11
<212> TYPE: PRT
<213> ORGANISM: Homo sapiens

<400> SEQUENCE: 167

Ile Lys Arg Gln Ser Glu His Ser Ile Leu Ala
1               5                   10

<210> SEQ ID NO 168
<211> LENGTH: 11
<212> TYPE: PRT
<213> ORGANISM: Homo sapiens

<400> SEQUENCE: 168

Val Lys Leu Glu Asp Arg Gln Thr Ser Trp Lys
1               5                   10

<210> SEQ ID NO 169
<211> LENGTH: 11
<212> TYPE: PRT
<213> ORGANISM: Homo sapiens

<400> SEQUENCE: 169

Asn Gly Ser Tyr Arg Cys Ser Ala Asn Phe Gln
1               5                   10
```

US 11,253,590 B2

ANTIBODIES SPECIFIC TO GLYCOSYLATED BTLA (B- AND T-LYMPHOCYTE ATTENUATOR)

1. CROSS-REFERENCES TO RELATED APPLICATIONS

This Application is the U.S. national stage application of the International Application No. PCT/US2016/064385, filed Dec. 1, 2016, which claims benefit of priority to U.S. Provisional Application Ser. No. 62/262,293, filed Dec. 2, 2015, the content of each of which is incorporated herein by reference in its entirety.

2. SEQUENCE LISTING

The instant application contains a Sequence Listing which has been filed electronically in ASCII format and is hereby incorporated by reference in its entirety. Said ASCII copy, created on Sep. 7, 2021, is named 13532-009-999 Substitute SL.txt and is 48,413 bytes in size.

3. FIELD

The present invention relates generally to the fields of medicine, molecular biology and oncology. More particularly, it concerns antibodies for treating cancers

4. BACKGROUND

The immune system of humans and other mammals protects them against infections and diseases. Upregulation of coinhibitory molecules by the tumor cells or tumor-infiltrating lymphocytes attenuates T-cell responses against cancer and appears to be a mechanism exerted by the tumor to escape immune response. Today, a variety of coinhibitory molecules, including T lymphocyte-associated antigen 4 (CTLA-4) and programmed death 1 (PD-1) have been implicated in immune escape of cancer cells. Antagonist antibodies are developed to overcome immune evasion and until now anti-CTLA-4 and anti-PD1 antibodies have been tested in clinical trials with encouraging results. However, development of new therapeutics that safely and effectively treat diseases by modulating the immune system remain an urgent need. The compositions and methods described herein meet these needs and provide other related advantages.

5. SUMMARY

Provided herein is an isolated monoclonal antibody, wherein the antibody selectively binds to glycosylated B- and T-lymphocyte attenuator ("BTLA") relative to unglycosylated BTLA. In some aspects, the antibody selectively binds to BTLA glycosylated at positions N75, N94, and/or N110 relative to unglycosylated BTLA.

In some embodiments, the isolated antibodies provided herein selectively bind to human BTLA glycosylated at N75, N94, N110 or any combination thereof, relative to unglycosylated BTLA. In some embodiments, the isolated antibodies selectively bind to human BTLA that has N75 glycosylation. In some embodiments, the isolated antibodies selectively bind to human BTLA that has N94 glycosylation. In some embodiments, the isolated antibodies selectively bind to human BTLA that has N110 glycosylation. In some embodiments, the isolated antibodies selectively bind to human BTLA that has N75 and N94 glycosylation. In some embodiments, the isolated antibodies selectively bind to human BTLA that has N94 and N110 glycosylation. In some embodiments, the isolated antibodies selectively bind to human BTLA that has N75 and N110 glycosylation. In some embodiments, the isolated antibodies selectively bind to human BTLA that has N75, N94 and N110 glycosylation.

In some aspects, the antibody selectively binds to one or more glycosylation motifs. In some aspects, the antibody binds to a glycopeptide comprising a glycosylation motif and the adjacent peptide. In some aspects, the antibody binds to a peptide sequence that is located near one or more of the glycosylation motifs in three dimensions. In certain aspects, the antibody binds to glycosylated BTLA with Kd less than half of the Kd exhibited relative to unglycosylated BTLA. In further aspects, the antibody binds to glycosylated BTLA with Kd at least 10 times less than the Kd exhibited relative to unglycosylated BTLA.

In some embodiments, the antibody specifically masks a glycosylation motif of BTLA comprising BTLA positions N75, N94, N110, or any combination thereof.

In some embodiments, binding of the antibody to glycosylated BTLA is indicated in a fluorescence assay by an at least 2-fold, at least 3-fold, at least 4-fold, at least 5-fold, at least 6-fold, at least 7-fold, at least 8-fold, at least 9-fold, or at least 10-fold greater fluorescence intensity than the fluorescence intensity exhibited with unglycosylated BTLA.

In some embodiments, the antibody comprises a heavy variable region comprising the amino acid sequence of SEQ ID NO: 2 and a light chain variable region comprising the amino acid sequence of SEQ ID NO: 4.

In some embodiments, the antibody comprises a heavy variable region comprising the amino acid sequence of SEQ ID NO: 30 and a light chain variable region comprising the amino acid sequence of SEQ ID NO: 32.

In some embodiments, the antibody comprises a heavy variable region comprising the amino acid sequence of SEQ ID NO: 58 and a light chain variable region comprising the amino acid sequence of SEQ ID NO: 60.

In some embodiments, the antibody comprises (a) a heavy chain variable ($V_H$) region comprising (1) a $V_H$ CDR1 having an amino acid sequence selected from the group consisting of (i) SEQ ID NO: 6, 34, or 62, (ii) SEQ ID NO: 9, 37, or 65, (iii) SEQ ID NO: 12, 40, or 68, and (iv) SEQ ID NO: 15, 43, or 71; (2) a $V_H$ CDR2 having an amino acid sequence selected from the group consisting of (i) SEQ ID NO: 7, 35, or 63, (ii) SEQ ID NO: 10, 38, or 66, (iii) SEQ ID NO: 13, 41, or 69, and (iv) SEQ ID NO: 16, 44, or 72; and (3) a $V_H$ CDR3 having an amino acid sequence selected from the group consisting of (i) SEQ ID NO: 8, 36, or 64, (ii) SEQ ID NO: 11, 39, or 67, (iii) SEQ ID NO: 14, 42, or 70, and (iv) SEQ ID NO: 17, 45, or 73; and/or (b) a light chain variable ($V_L$) region comprising (1) a $V_L$ CDR1 having an amino acid sequence selected from the group consisting of (i) SEQ ID NO: 18, 46, or 74, (ii) SEQ ID NO: 21, 49, or 77, (iii) SEQ ID NO: 24, 52, or 80, and (iv) SEQ ID NO: 27, 55, or 83; (2) a $V_L$ CDR2 having an amino acid sequence selected from the group consisting of (i) SEQ ID NO: 19, 47, or 75, (ii) SEQ ID NO: 22, 50, or 78, (iii) SEQ ID NO: 25, 53, or 81, and (iv) SEQ ID NO: 28, 56, or 84; and (3) a $V_L$ CDR3 having an amino acid sequence selected from the group consisting of (i) SEQ ID NO: 20, 48, or 76, (ii) SEQ ID NO: 23, 51, or 79, and (iii) SEQ ID NO: 26, 54, or 82.

In some embodiments, the antibody competes with the antibody designated as STC613, the antibody designated as STC626, or the antibody designated as STC635 for binding to glycosylated BTLA.

In some embodiments, the antibody specifically binds to a BTLA epitope comprising a sequence of five or more consecutive amino acids of an amino acid sequence of SEQ ID NOS: 161, 162, 163, 164, 165, 166, 167, 168, or 169.

In some embodiments, the antibody specifically binds to a BTLA epitope comprising one or more of amino acids corresponding to R12, H16, K51, T57, S82, or S86 of a BTLA of SEQ ID NO: 86.

In some embodiments, the antibody specifically binds to glycosylated BTLA with a dissociation constant (Kd) of no more than 1 µM.

In some embodiments, the antibody specifically binds to glycosylated BTLA with a dissociation constant (Kd) of no more than 100 nM, no more than 10 nM, or no more than 5 nM.

In some embodiments, the antibody specifically binds to glycosylated BTLA with a dissociation constant (Kd) of no more than 5 nM.

In some embodiments, the antibody inhibits HVEM binding to BTLA.

In some embodiments, the antibody inhibits HVEM binding with an IC50 of no more than 1 µg/ml.

In some embodiments, the antibody inhibits HVEM binding with an IC50 of no more than 0.8 µg/ml, no more than 0.6 µg/ml, no more than 0.4 µg/ml, no more than 0.2 µg/ml.

In some embodiments, the antibody inhibits HVEM binding with an IC50 of no more than 0.2 µg/ml.

In some aspects, the antibody is recombinant. In certain aspects, the antibody is an IgG, IgM, IgA or an antigen binding fragment thereof. In other aspects, the antibody is a Fab', a F(ab')2, a F(ab')3, a monovalent scFv, a bivalent scFv, a bispecific antibody, a bispecific scFv, or a single domain antibody. In some aspects, the antibody is a human or humanized antibody. In further aspects, the antibody is conjugated to an imaging agent, a chemotherapeutic agent, a toxin or a radionuclide.

In a further embodiment, provided herein is a composition comprising an antibody of the embodiments (e.g., an antibody selectively binds to glycosylated BTLA relative to unglycosylated BTLA) in a pharmaceutically acceptable carrier.

In still a further embodiment there is provided an isolated polypeptide comprising a fragment of at least 7 (e.g., at least 8, 9, 10, 11, 12, 13, 14, 15, 16, 17, 18, 19, 20 or more) contiguous amino acids of human BTLA comprising at least one amino acid corresponding to position N75, N94, or N110 of human BTLA. In further aspects, an isolated polypeptide of the embodiments comprises a fragment of at least 7 (e.g., at least 8, 9, 10, 11, 12, 13, 14, 15, 16, 17, 18, 19, 20 or more) contiguous amino acids of human BTLA, comprising at least one amino acid corresponding to position N75, N94, or N110 of human BTLA and wherein at least one of said amino acids corresponding to position N75, N94, or N110 of human BTLA is glycosylated. In some aspects, a polypeptide of the embodiments is fused or conjugated to an immunogenic polypeptide (e.g., keyhole limpet hemocyanin, KLH). In certain aspects, the polypeptide further comprises a Cys residue at the C- or N-terminus. For example, in some aspects, the polypeptide is conjugated to an immunogenic polypeptide by a disulfide linkage at the Cys residue.

In yet a further embodiment, a composition is provided comprising a polypeptide comprising a fragment of at least 7 (e.g., at least 8, 9, 10, 11, 12, 13, 14, 15, 16, 17, 18, 19, 20 or more) contiguous amino acids of human BTLA comprising at least one amino acid corresponding to position N75, N94, or N110 of human BTLA, wherein at least one of said amino acids corresponding to position N75, N94, or N110 of human BTLA is glycosylated, wherein the polypeptide is formulated in a pharmaceutically acceptable carrier.

In yet a further embodiment, an immunogenic composition is provided comprising a polypeptide comprising a fragment of at least 7 contiguous amino acids of human BTLA comprising at least one amino acid corresponding to position N75, N94, or N110 of human BTLA, wherein at least one of said amino acids corresponding to position N75, N94, or N110 of human BTLA is glycosylated, wherein the polypeptide is formulated in a pharmaceutically acceptable carrier. In some aspects, the immunogenic composition further comprises an adjuvant, such as alum or Freund's adjuvant.

In still a further embodiment provided herein is a method for treating a subject having a cancer comprising administering an effective amount of an antibody or an isolated polypeptide of the embodiments to the subject. In certain aspects, a method for treating a cancer comprises administering an effective amount of a polypeptide (e.g., a glycosylated BTLA polypeptide) to a subject. In further aspects, a method of treating a cancer comprises administering an effective amount of an antibody of the embodiments (e.g., an antibody selectively binds to glycosylated BTLA relative to unglycosylated BTLA) to a subject. In some aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In certain aspects, the cancer is an adrenal cancer, an anal cancer, a bile duct cancer, a bladder cancer, a bone cancer, a brain/CNS tumor in an adult, a brain/CNS tumor in a child, a breast cancer, a breast cancer in a man, cancer in an adolescent, cancer in a child, cancer in a young adult, cancer of unknown primary, Castleman disease, cervical cancer, colon/rectum cancer, endometrial cancer, esophagus cancer, Ewing family tumor, eye cancer, gallbladder cancer, gastrointestinal carcinoid tumor, gastrointestinal stromal tumor (GIST), gestational trophoblastic disease, Hodgkin disease, Kaposi sarcoma, kidney cancer, laryngeal or hypopharyngeal cancer, leukemia (e.g., adult acute lymphocytic (ALL), acute myeloid (AML), chronic lymphocytic (CLL), chronic myeloid (CML), chronic myelomonocytic (CMML), childhood leukemia), liver cancer, lung cancer (e.g., non-small cell, small cell), lung carcinoid tumor, lymphoma, lymphoma of the skin, malignant mesothelioma, multiple myeloma, myelodysplastic syndrome, naval cavity cancer, paranasal sinus cancer, nasopharyngeal cancer, neuroblastoma, non-Hodgkin lymphoma, non-Hodgkin lymphoma in a child, oral cavity cancer, oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma (e.g., adult soft tissue cancer), skin cancer (e.g., basal and squamous cell, melanoma, merkel cell), small intestine cancer, stomach cancer, testicular cancer, thymus cancer, thyroid cancer, uterine sarcoma, vaginal cancer, vulvar cancer, Waldenstrom macroglobulinemia, or Wilms tumor. In certain aspects, the antibody is in a pharmaceutically acceptable composition. In further aspects, the antibody is administered systemically. In particular aspects, the antibody is administered intravenously, intradermally, intratumorally, intramuscularly, intraperitoneally, subcutaneously or locally.

In some aspects, the method further comprises administering at least a second anticancer therapy to the subject. In certain aspects, wherein the second anticancer therapy is a surgical therapy, chemotherapy, radiation therapy, cryotherapy, hormonal therapy, immunotherapy or cytokine therapy.

In yet still a further embodiment provided herein is a method for assessing BTLA glycosylation, N-linked glycosylation or N-glycosylation comprising contacting the BTLA-containing sample with an antibody of the embodiments (e.g., an antibody selectively binds to glycosylated BTLA relative to unglycosylated BTLA). In some aspects, the method is an in vitro method. In certain aspects, the sample is cell sample.

In yet still a further embodiment a method of making an antibody is provided comprising administering a polypeptide according to the embodiments (e.g., a polypeptide having a fragment of at least 7 contiguous amino acids of human BTLA comprising at least one amino acid corresponding to position N75, N94, or N110 of human BTLA, wherein at least one of said amino acids corresponding to position N75, N94, or N110 of human BTLA is glycosylated) to an animal and isolating the antibody from the animal. For example, the animal can be a mouse, rat, rabbit or human. In certain aspects a method further includes identifying the CDRs of the antibody and humanizing the sequences surrounding the CDRs to produce a humanized antibody. In still further aspects, the method comprises recombinantly expressing the humanized antibody. Thus, in a further embodiment, provided herein is an isolated antibody produced by the foregoing method. Thus, in some embodiments, provided herein is an isolated antibody that selectively binds to a polypeptide of the embodiments (e.g., a polypeptide comprising a fragment of at least 7 contiguous amino acids of human BTLA comprising at least one amino acid corresponding to position N75, N94, or N110 of human BTLA, wherein at least one of said amino acids corresponding to position N75, N94, or N110 of human BTLA is glycosylated) relative to unglycosylated BTLA.

6. BRIEF DESCRIPTION OF THE DRAWINGS

The following drawings form part of the present specification and are included to further demonstrate certain aspects of the present invention. The invention can be better understood by reference to one or more of these drawings in combination with the detailed description of specific embodiments presented herein.

FIG. 1A—Dot blot analysis of anti-BTLA mAbs; experimental layout. FIG. 1A shows a schematic illustrating the layout of anti-BTLA mAb samples (STC601-STC636) and controls (IgG control antibody; commercially available BTLA antibody by Biolegend, San Diego, Calif., US) tested in a dot blot assay. "PNGase F+" indicates endoglycosidase treated BTLA; "PNGase F—" indicated untreated, glycosylated BTLA.

FIG. 1B—Dot blot analysis of anti-BTLA mAbs; experimental results. FIG. 1B shows exemplary results of a dot blot assay evaluating glyco-specific BTLA binding of anti-BTLA mAbs STC601-STC636.

Figure 2:
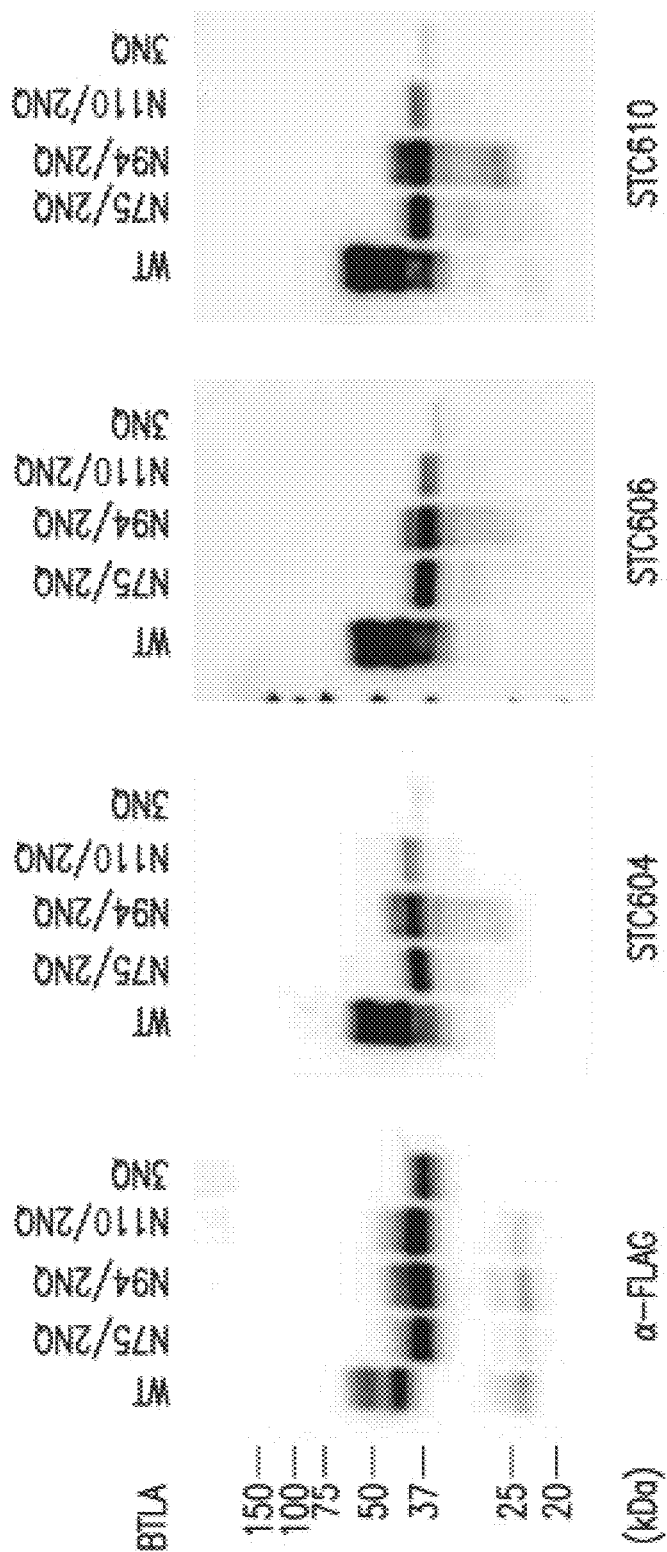
Figure 2:
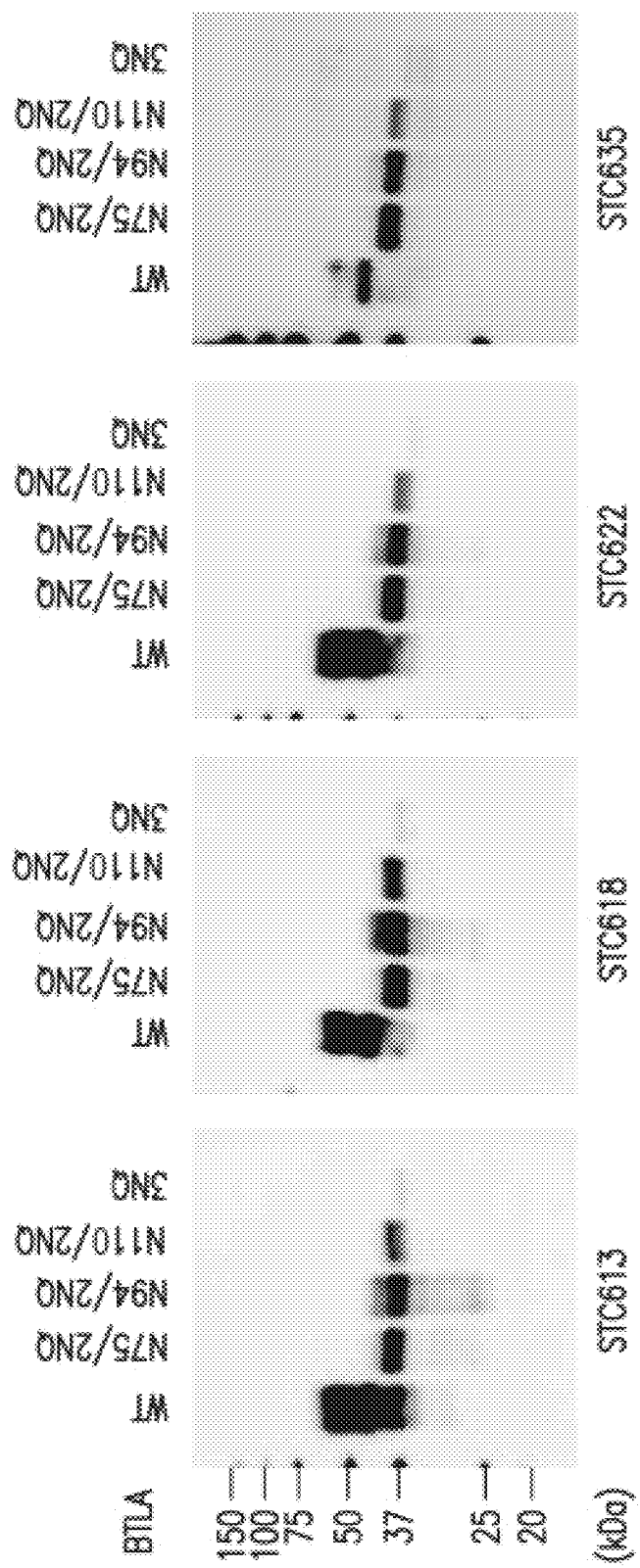
Figure 2:
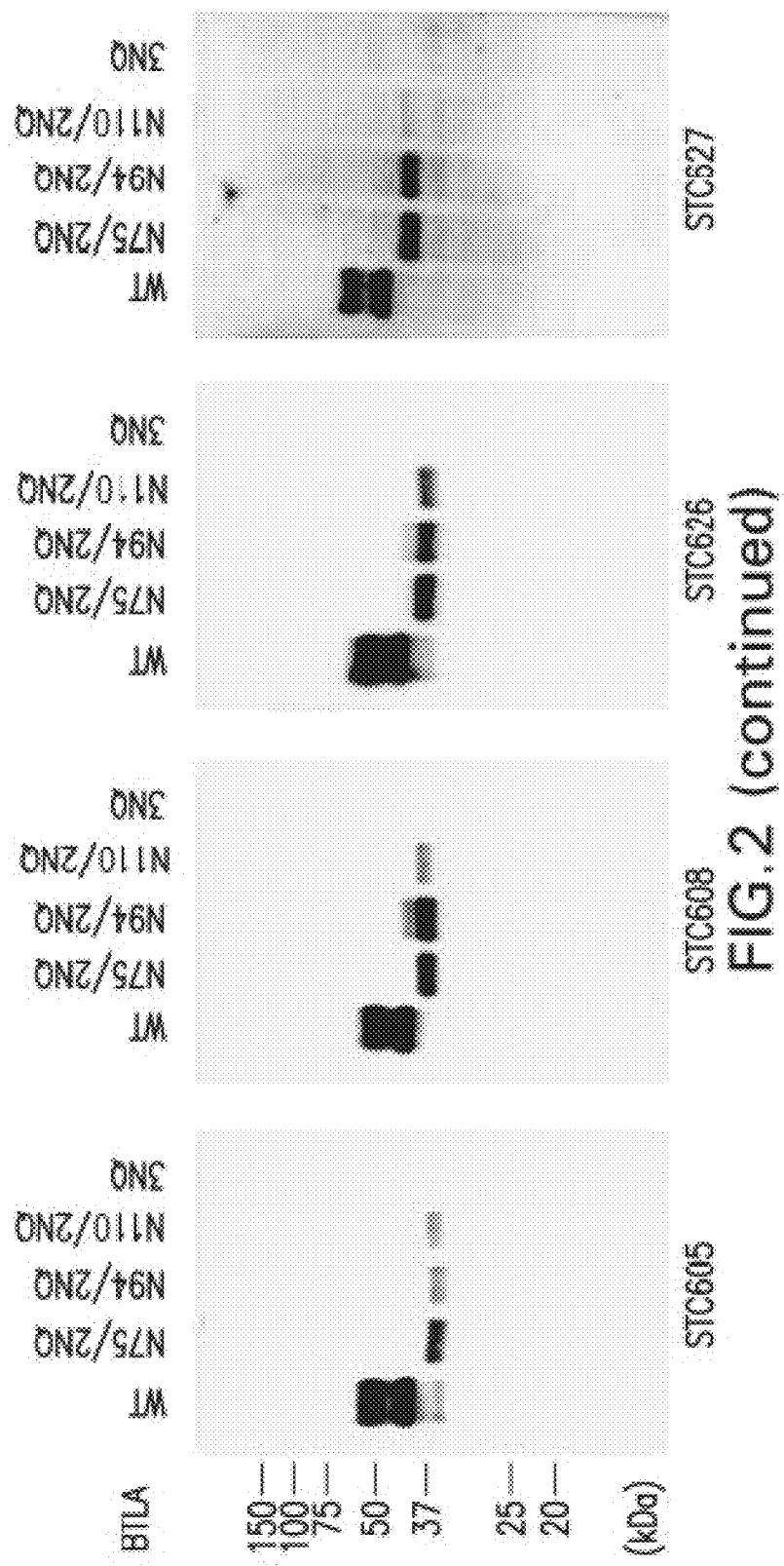
Figure 2:
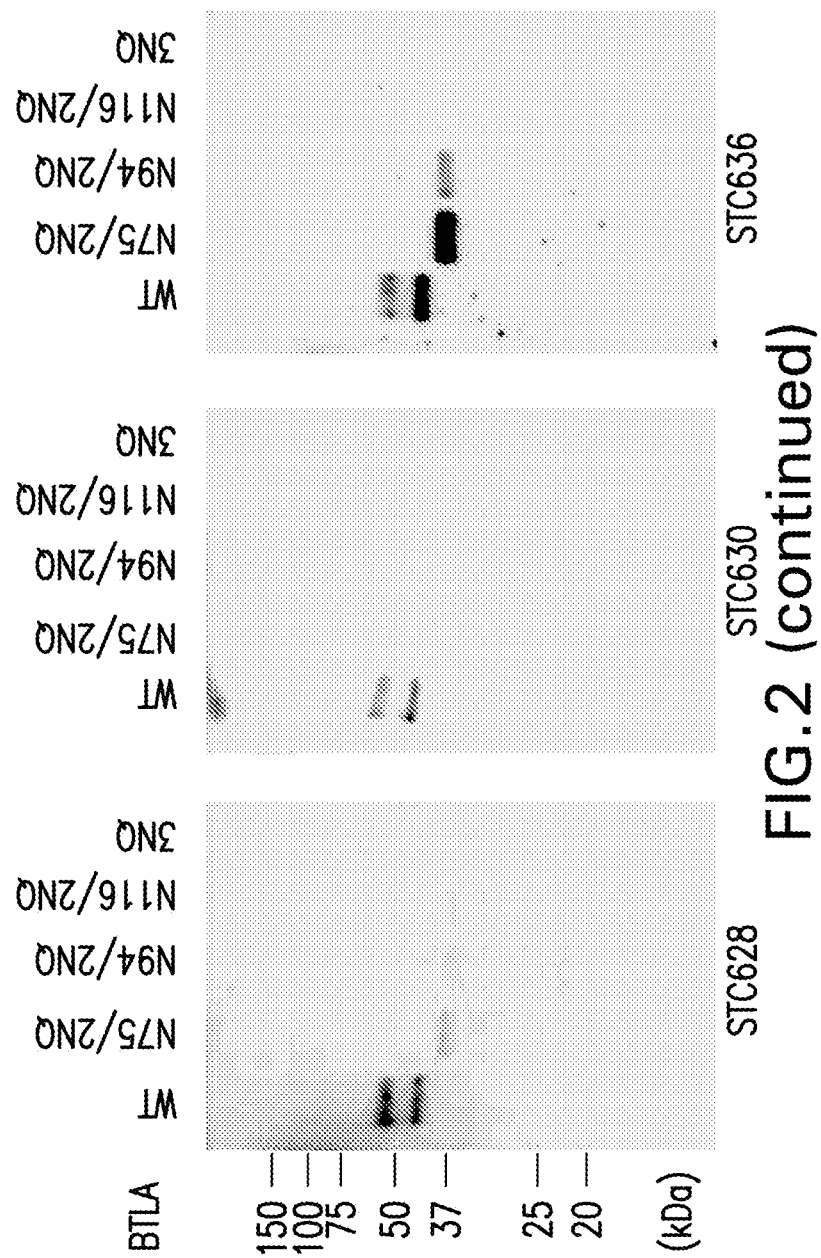

FIG. 2 Western blot analysis of anti-BTLA mAbs. FIG. 2 shows exemplary Western blot results illustrating binding of BTLA mAbs to wild-type (WT) BTLA and to BTLA mutants retaining a single N-glycosylation site (N75/2NQ, N94/2NQ, N110/2NQ) or no N-glycosylation site (3NQ).

Figure 3A:
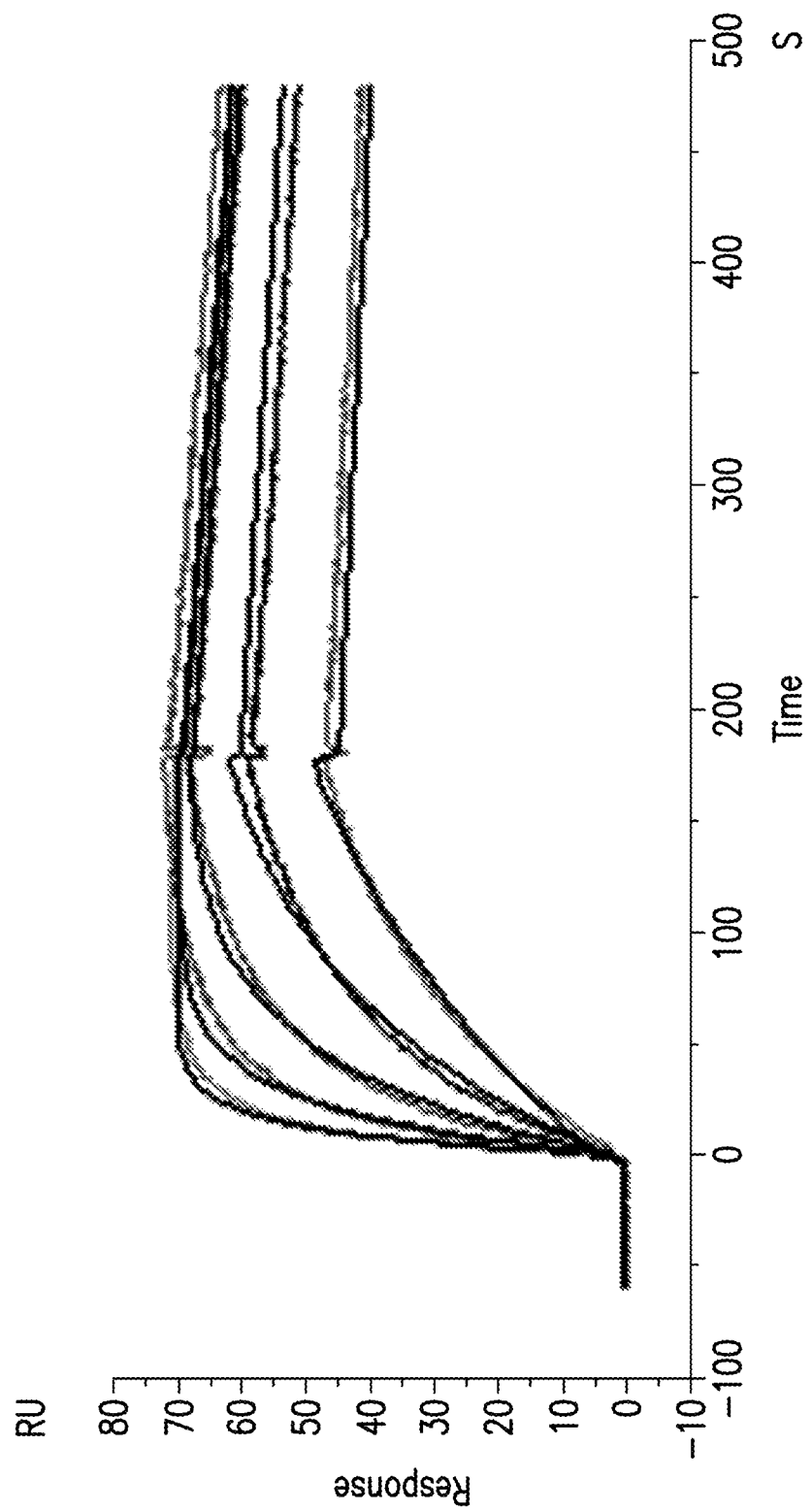

FIG. 3A—Surface plasmon resonance BTLA binding assay; FIG. 3A shows sensograms illustrating a BTLA titration experiment and BTLA binding to immobilized anti-BTLA mAb designated as STC613.

Figure 3B:
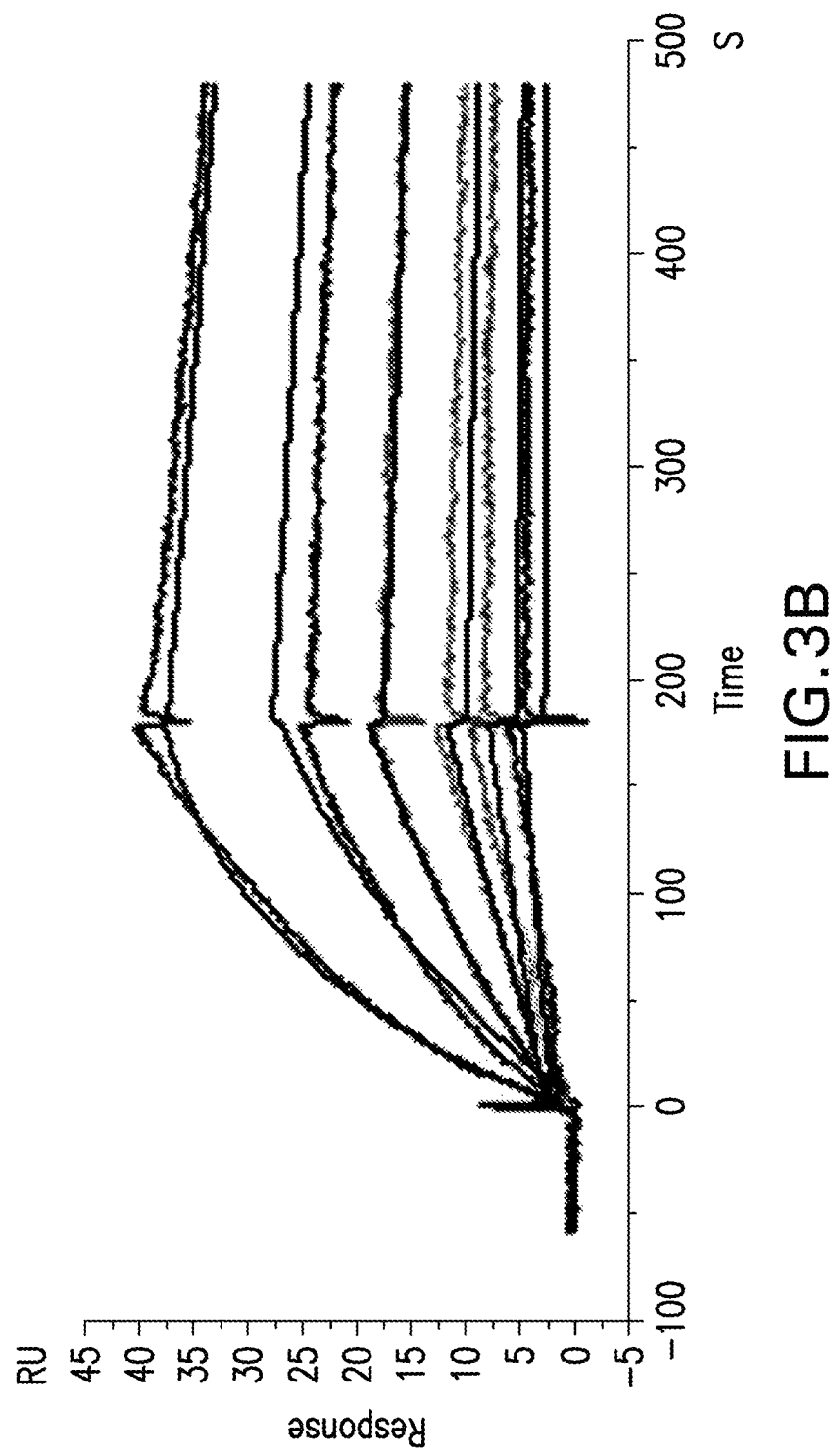

FIG. 3B—Surface plasmon resonance BTLA binding assay; FIG. 3B shows sensograms illustrating a BTLA titration experiment and BTLA binding to immobilized anti-BTLA mAb designated as STC626.

Figure 3C:
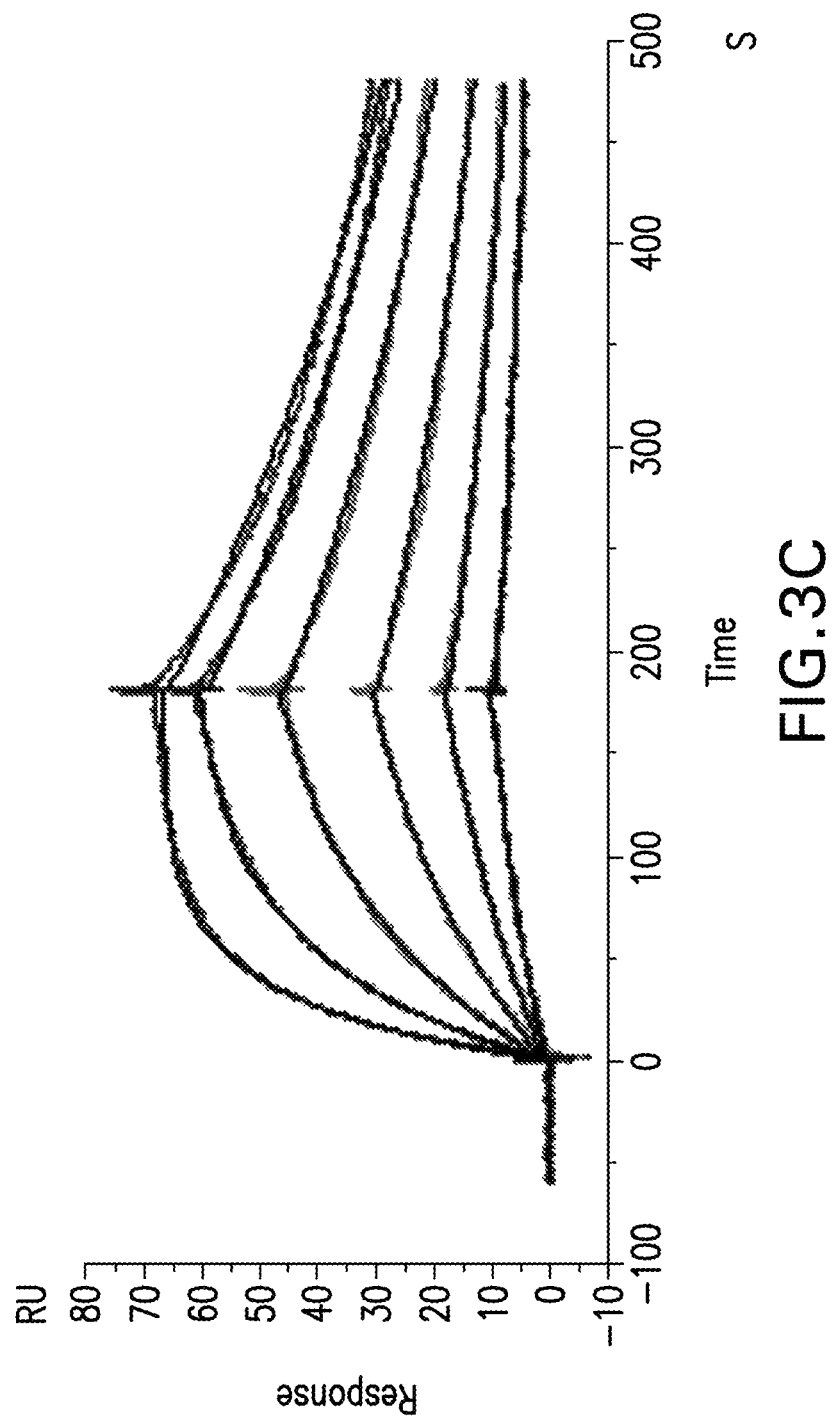

FIG. 3C—Surface plasmon resonance BTLA binding assay; FIG. 3C shows sensograms illustrating a BTLA titration experiment and BTLA binding to immobilized anti-BTLA mAb designated as STC636.

Figure 4A:
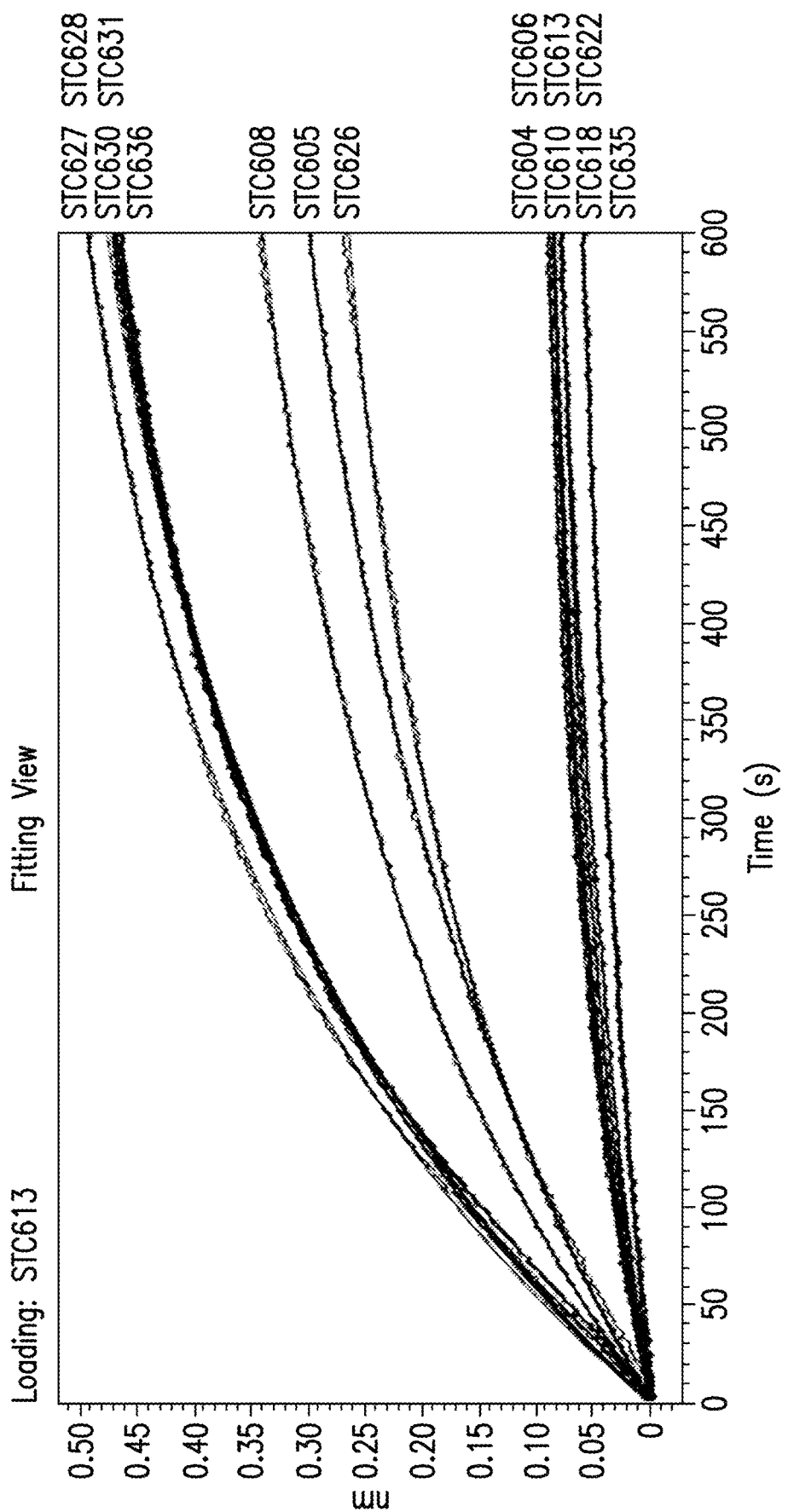

FIG. 4A—Binning of anti-BTLA mAbs with STC613. FIG. 4A shows exemplary results of a surface plasmon resonance experiment illustrating binding of anti-BTLA mAbs to a BTLA-STC613 complex.

Figure 4B:
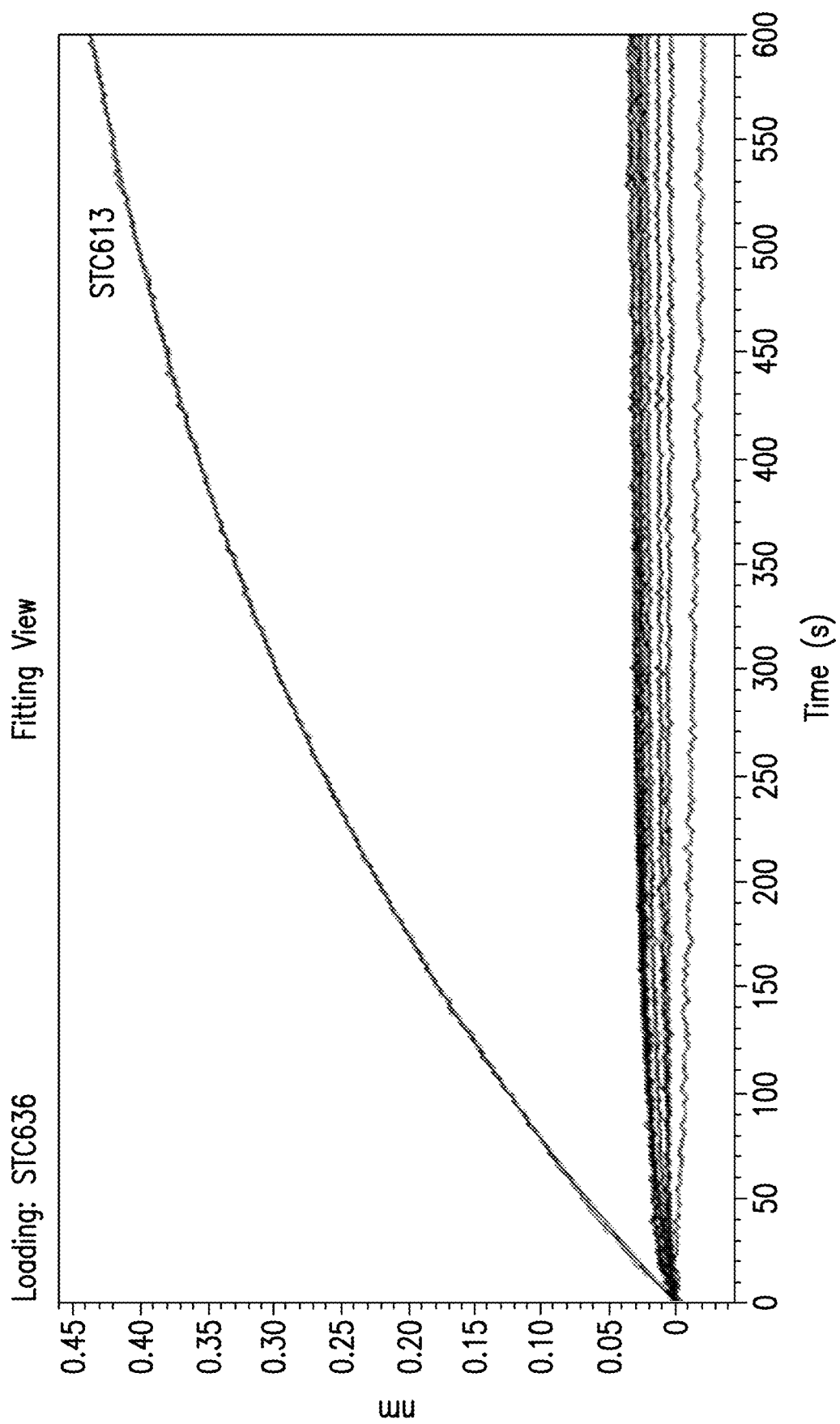

FIG. 4B—Binning of anti-BTLA mAbs with STC636. FIG. 4B shows exemplary results of a surface plasmon resonance experiment illustrating binding of anti-BTLA mAbs to a BTLA-STC636 complex.

Figure 5:
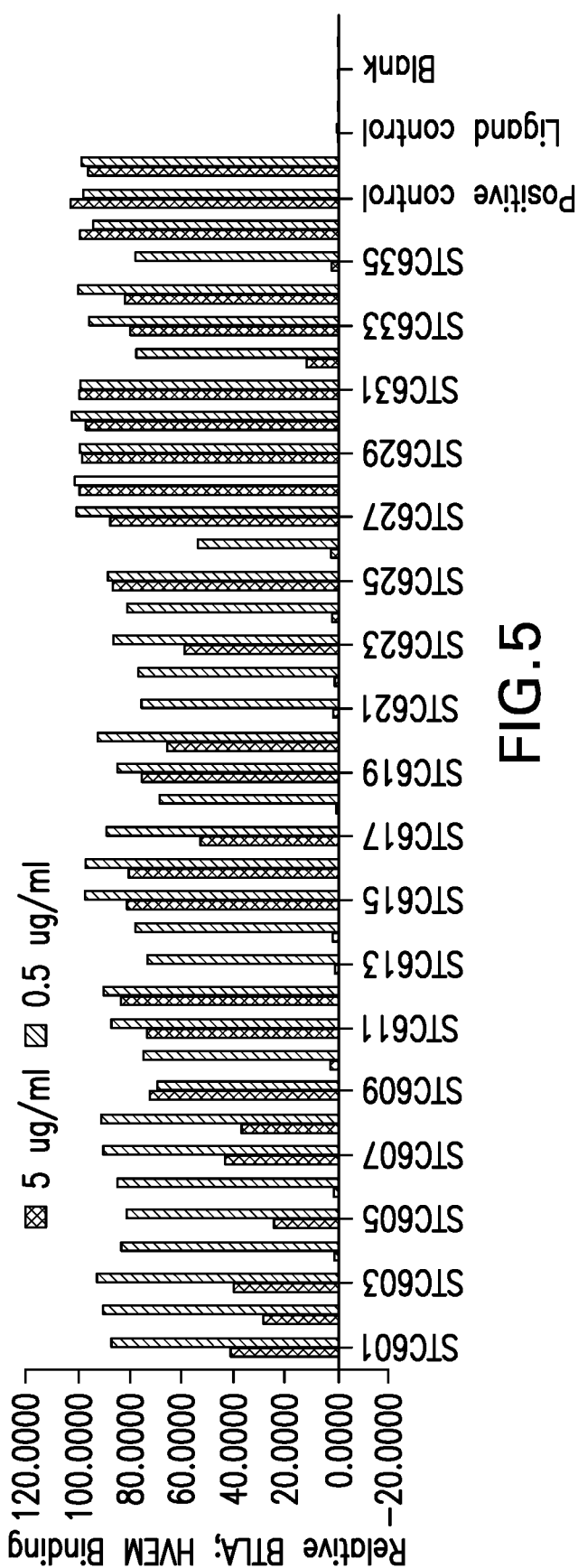

FIG. 5—Neutralizing Activity of anti-BTLA mAbs. FIG. 5 shows a bar diagram illustrating exemplary results of an ELISA assay analyzing BTLA:HVEM complex formation in the presence of 5 µg/ml or 0.5 µg/ml anti-BTLA mAbs.

Figure 6:
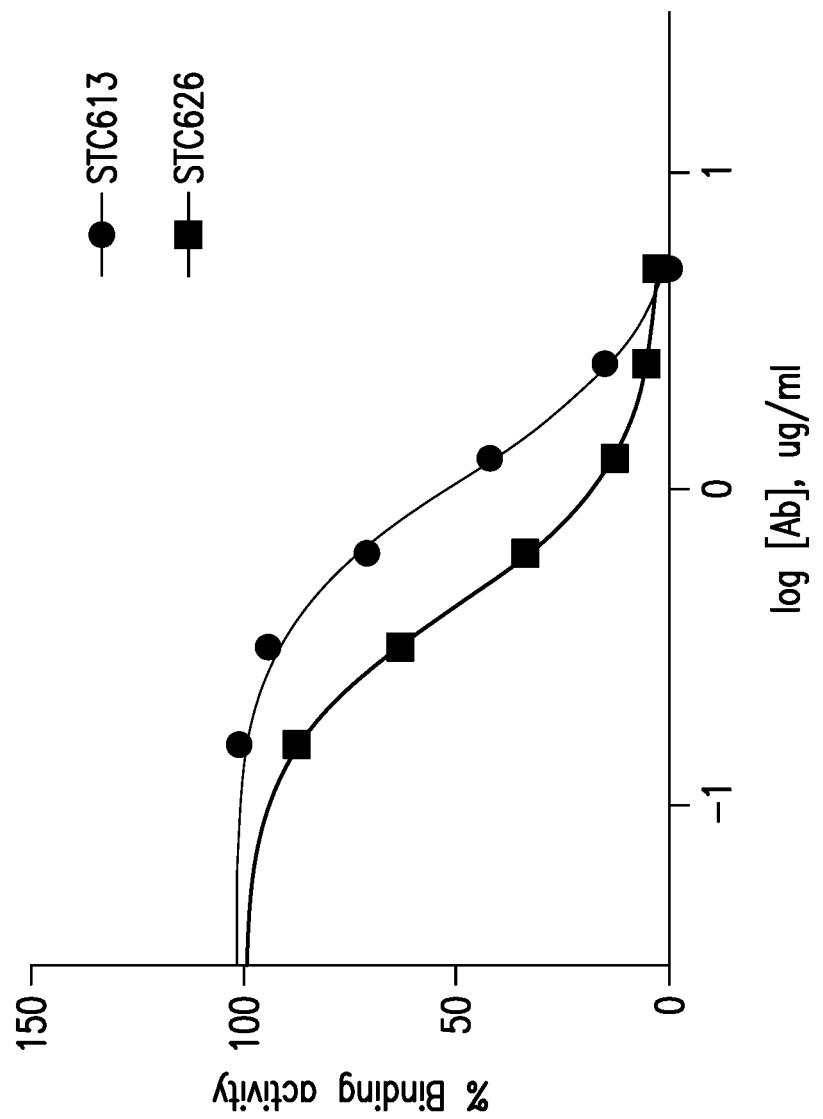

FIG. 6—Neutralizing Activity of STC613 and STC626. FIG. 6 a graph illustrating titration curves for STC613 and STC626 in an ELISA-based BTLA:HVEM competition assay.

FIG. 7 BTLA Epitope Mapping of STC613. FIG. 7 shows a graph illustrating BTLA regions and amino acid positions found to be cross-linked to STC613 in a BTLA-STC613 complex. Particularly, shown in this figure is a synthesized epitope of BTLA antigen (SEQ ID NO: 86) for STC613: IKRQSEHSILA (SEQ ID NO: 167)—VKLEDRQTSWK (SEQ ID NO: 168)-NGSYRCSANFQ (SEQ ID NO: 169).

7. DETAILED DESCRIPTION

7.1. Overview

BTLA was identified as an immunoglobulin domain-containing glycoprotein with two immunoreceptor tyrosine-based inhibitory motifs. BTLA is an inhibitory receptor on T lymphocytes that is not expressed by naive T cells, but induced during activation of T cells. Watanabe et al., *Nature Immunology* 4, 670-679(2003).

N-glycosylation is a posttranslational modification that is initiated in the endoplasmic reticulum (ER) and subsequently processed in the Golgi (Schwarz & Aebi, *Current Opinion in Structural Biology* 21, 576-582(2011)). This type of modification is first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, *Methods* 41(4): 451-59 (2007); Helenius and Aebi, *Science* 291 (5512): 2364-69 (2001)). The addition or removal of saccharides from the preformed glycan is mediated by a group of glycotransferases and glycosidases, respectively, which tightly regulate the N-glycosylation cascade in a cell- and location-dependent manner.

As used herein, and unless otherwise specified, the term "B- and T-lymphocyte attenuator" or "BTLA" refers to BTLA from any vertebrate source, including mammals such as primates (e.g., humans, cynomolgus monkey (cyno)), dogs, and rodents (e.g., mice and rats). Unless otherwise specified, BTLA also includes various BTLA isoforms, related BTLA polypeptides, including SNP variants thereof, as well as different modified forms of BTLA, including but not limited to phosphorylated BTLA, glycosylated BTLA, and ubiquitinated BTLA.

An exemplary amino acid sequence of human BTLA is provided below, in which the sites for N-linked glycosylation are bolded underlined (N75, N94, and N110):

(SEQ ID NO: 1)
MKTLPAMLGT GKLFWVFFLI PYLDIWNIHG KESCDVQLYI

KRQSEHSILA GDPFELECPV KYCANRPHVT WCKLNGTTCV

KLEDRQTSWK EEKNISFFIL HFEPVLPNDN GSYRCSANFQ

SNLIESHSTT LYVTDVKSAS ERPSKDEMAS RPWLLYRLLP

LGGLPLLITT CFCLFCCLRR HQGKQNELSD TAGREINLVD

AHLKSEQTEA STRQNSQVLL SETGIYDNDP DLCFRMQEGS

EVYSNPCLEE NKPGIVYASL NHSVIGPNSR LARNVKEAPT

EYASICVRS

As shown in the table below, all three N-glycosylation sites are located in the extracellular domain of BTLA.

| Feature key | Position(s) | Length | Description |
|---|---|---|---|
| Topological domain | 31-157 | 127 | Extracellular |
| Transmembrane | 158-178 | 21 | Helical |
| Topological domain | 179-289 | 111 | Cytoplasmic |

The specific glycosylation sites of a particular BTLA isoform or variant can vary from amino acids 75, 94, and 110 of that particular BTLA isoform or variant. In those circumstances, a person of ordinary skill in the art would be able to determine the glycosylation sites of any particular BTLA isoform or variant that corresponding to N75, N94, and N110 of the human BTLA exemplified above based on sequence alignment and other common knowledge in the art. As such, provided herein also are antibodies that selectively bind to a glycosylated form of a BTLA isoform or variant relative to the unglycosylated BTLA isoform or variant. The glycosylated sites of a BTLA isoform or variant can be the corresponding sites of N75, N94, and N110 of human BTLA sequence as provided above. Provided herein are also polypeptides comprising a fragment of at least 7 (e.g., at least 8, 9, 10, 11, 12, 13, 14, 15, 16, 17, 18, 19, 20 or more) contiguous amino acids of a BTLA isoform or variant comprising at least one amino acid corresponding to position N75, N94, or N110 of human BTLA sequence as provided above.

As used herein, and unless otherwise specified, the articles "a," "an," and "the" refer to one or to more than one of the grammatical object of the article. By way of example, an antibody refers to one antibody or more than one antibodies.

As used herein, and unless otherwise specified, the term "or" is used interchangeably with "and/or" unless explicitly indicated to refer to alternatives only or the alternatives are mutually exclusive. As used herein, and unless otherwise specified, "another" refers to at least a second or more.

As used herein, and unless otherwise specified, the term "about" indicates that a value includes the inherent variation of error for the device, the method being employed to determine the value, or the variation that exists among the study subjects.

7.2. Antibodies and Polypeptides

As used herein, and unless otherwise specified, the term "antibody" refers to a polypeptide product of B cells within the immunoglobulin (or "Ig") class of polypeptides that is able to bind to a specific molecular antigen, such as IgG, IgM, IgA, IgD, IgE, as well as other molecules having an antigen binding fragment. An antibody can be composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press; Kuby (1997) *Immunology*, Third Edition, W.H. Freeman and Company, New York). Here, the specific molecular antigen includes the glycosylated human BTLA. Antibodies provided herein include, but are not limited to, polyclonal antibodies, monoclonal antibodies, synthetic antibodies, recombinantly produced antibodies, bi-specific antibodies, multispecific antibodies, human antibodies, humanized antibodies, camelized antibodies, chimeric antibodies, intrabodies, anti-idiotypic (anti-Id) antibodies.

As used herein, and unless otherwise specified, the term "isolated" when used in reference to an antibody, antigen binding fragment or polynucleotide means that the referenced molecule is free of at least one component as it is found in nature. The term includes an antibody, antigen binding fragment or polynucleotide that is removed from some or all other components as it is found in its natural environment. Components of an antibody's natural environment include, for example, erythrocytes, leukocytes, thrombocytes, plasma, proteins, nucleic acids, salts and nutrients. Components of an antigen binding fragment's or polynucleotide's natural environment include, for example, lipid membranes, cell organelles, proteins, nucleic acids, salts and nutrients. An antibody, antigen binding fragment or polynucleotide of the invention can also be free or all the way to substantially free from all of these components or any other component of the cells from which it is isolated or recombinantly produced.

As used herein, and unless otherwise specified, the term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, and unless otherwise specified, the term "human antibody" refers to an antibody that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. Here, a human antibody can include an antibody that binds to glycosylated human BTLA and is encoded by a nucleic acid sequence that is a naturally occurring somatic variant of the human germline immunoglobulin nucleic acid sequence.

As used herein, and unless otherwise specified, the term "chimeric antibody" refers to an antibody that a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)).

As used herein, and unless otherwise specified, the term "humanized antibody" refers to chimeric antibodies that include human immunoglobulins (e.g., recipient antibody) in which the native Complementarity Determining Region ("CDR") residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can have residues that are not found in the recipient antibody or in the donor antibody. These modifications are made to further refine antibody performance. A humanized antibody heavy or light chain can have substantially all of at least one or more variable regions, in which all or substantially all of the CDRs correspond to those of a nonhuman immunoglobulin and all or substantially all of the FRs are those of a human immunoglobulin sequence. The humanized antibody can have at least a portion of an immunoglobulin constant region (Fc), typically that of a human immunoglobulin. For further details, see, Jones et al., *Nature*, 321:522-525 (1986); Riechmann et al., *Nature*, 332:323-329 (1988); and Presta, *Curr. Op. Struct. Biol.*, 2:593-596 (1992); Carter et al., *Proc. Natl. Acd. Sci. USA* 89:4285-4289 (1992); and U.S. Pat. Nos. 6,800,738, 6,719,971, 6,639,055, 6,407,213, and 6,054,297.

As used herein, and unless otherwise specified, the term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295(1992)) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (see Kabat, E. A. et al. (1991) *Sequences of Proteins of Immunological Interest*, Fifth Edition, U.S. Department of Health and Human Services, NIH Publication No. 91-3242). The recombinant antibodies can also be subjected to in vitro mutagenesis (or, when an animal transgenic for human Ig sequences is used, in vivo somatic mutagenesis) and thus the amino acid sequences of the VH and VL regions of the recombinant antibodies can be sequences that, while derived from and related to human germline VH and VL sequences, do not naturally exist within the human antibody germline repertoire in vivo.

As used herein, and unless otherwise specified, a "neutralizing antibody" refers to an antibody that blocks the binding of BTLA with its natural ligands, such as the herpesvirus-entry mediator (HVEM), and inhibits the signaling pathways mediated by BTLA and/or its other physiological activities. The IC50 of a neutralizing antibody refers to the concentration of the antibody that is required to neutralize 50% of BTLA in a neutralization assay, such as an ELISA assay analyzing BTLA-HVEM complex formation. The IC50 of the neutralizing antibody can range between 0.01-10 µg/ml in the neutralization assay.

As used herein, and unless otherwise specified, the term "antigen binding fragment" and similar terms refer to a portion of an antibody which includes the amino acid residues that immunospecifically bind to an antigen and confer on the antibody its specificity and affinity for the antigen. An antigen binding fragment can be referred to as a functional fragment of an antibody. An antigen binding fragment can be monovalent, bivalent, or multivalent.

Molecules having an antigen binding fragment include, for example, an Fd, Fv, Fab, F(ab'), F(ab)$_2$, F(ab')$_2$, F(ab)$_3$, F(ab')$_3$, single chain Fv (scFv), diabody, triabody, tetrabody, minibody, or a single domain antibody. A scFv can be monovalent scFv or bivalent scFv. Other molecules having an antigen binding fragment can include, for example, heavy or light chain polypeptides, variable region polypeptides or CDR polypeptides or portions thereof so long as such antigen binding fragments retain binding activity. Such antigen binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990). An antigen binding fragment can be a polypeptide having an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The heavy chain of an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\epsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The light chain of an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The variable domain or variable region of an antibody refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5$^{th}$ ed. A variable region can be a human variable region.

A CDR refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to standard designations, are set forth in the Table 1 below.

TABLE 1

CDR Definitions

| | Exemplary (Kabat + Chothia) | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

The "framework" or "FR" residues refer to those variable domain residues flanking the CDRs. FR residues are present, e.g., in chimeric, humanized, human, domain antibodies, diabodies, linear antibodies, and bispecific antibodies. FR residues are those variable domain residues other than the hypervariable region residues herein defined.

As used herein, and unless otherwise specified, the term "isolated" as used in reference to an antibody means the antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated.

As used herein, and unless otherwise specified, the term "polynucleotide," "nucleotide," nucleic acid" "nucleic acid molecule" and other similar terms are used interchangeable and include DNA, RNA, mRNA and the like.

As used herein, and unless otherwise specified, the term "isolated" as used in reference to a nucleic acid molecule means the nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

As used herein and unless otherwise specified, the term "bind" or "binding" refers to an interaction between molecules. Interactions can be, for example, non-covalent interactions including hydrogen bonds, ionic bonds, hydrophobic interactions, and/or van der Waals interactions. The strength of the total non-covalent interactions between an antibody and a single epitope of a target molecule, such as glycosylated human BTLA, is the affinity of the antibody for that epitope. "Binding affinity" generally refers to the strength of the sum total of noncovalent interactions between a single binding site of a molecule (e.g., a binding protein such as an antibody) and its binding partner (e.g., an antigen).

The affinity of a binding molecule X, such as an antibody, for its binding partner Y, such as the antibody's cognate antigen can generally be represented by the dissociation constant ($K_D$). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. The "$K_D$" or "$K_D$ value" can be measured by assays known in the art, for example by a binding assay. The $K_D$ can be measured in a radiolabeled antigen binding assay (RIA), for example, performed with the Fab version of an antibody of interest and its antigen (Chen, et al., (1999) *J Mol. Biol.* 293:865-881). The $K_D$ or $K_D$ value can also be measured by using surface plasmon resonance assays by Biacore, using, for example, a BIAcore™-2000 or a BIAcore™-3000 BIAcore, Inc., Piscataway, N.J.), or by biolayer interferometry using, for example, the OctetQK384 system (ForteBio, Menlo Park, Calif.). As used herein, and unless otherwise specified, an antibody that is said to be able to "selectively bind" a first molecular antigen relative to a second molecular antigen if the antibody binds to the first molecular antigen with higher affinity than the second molecular antigen. An antibody in general do not bind to a totally unrelated antigen.

As used herein, and unless otherwise specified, the term "polypeptide," as used herein, includes an oligopeptide having between 2 and 30 amino acids (e.g., 2, 3, 4, 5, 6, 7, 8, 9, 10, 12, 14, 16, 18, 20, 25 or 30 amino acids) as well as longer amino acid chains, for example, more than 30 amino acids, more than 50 amino acids, more than 100 amino acids, more than 150 amino acids, more than 200 amino acids, more than 300 amino acids, more than 400 amino acids, more than 500 amino acids, or more than 600 amino acids. A polypeptide can be produced, for example, recombinant expression, or by chemical synthesis. The polypeptide of this disclosure can be posttranslationally or chemically modified (e.g., glycosylation, carbamylation, phosphorylation, biotinylation, attachment of fluorescent dyes, and the like). A polypeptide can be glycosylated at specific sites. A polypeptide can include unnatural amino acids that are not encoded by the natural genetic code. For example, a polypeptide can include methylated backbone structures, peptoid backbone structures (poly-N-substituted glycines), L-amino acids, R-amino acids, and the like. A polypeptide can have a wild-type sequence, naturally occurring variant sequence, mutant sequences (e.g., point mutants, deletion mutants), and the like.

As used herein, and unless otherwise specified, the term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-BTN1A1 antibody provided herein), and it is further understood that expression levels can be optimized to obtain sufficient expression using methods well known in the art.

As used herein, and unless otherwise specified, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

7.2.1. Anti-Glycosylated BTLA Antibodies

Provided herein are isolated antibodies that selectively binds to glycosylated BTLA relative to unglycosylated BTLA. The BTLA can be human BTLA. The glycosylated BTLA can be a specific N-glycan structure of BTLA or a glycopeptide of BTLA. In some embodiments, the antibodies provided herein are antigen binding fragments that selectively bind to glycosylated BTLA relative to unglycosylated BTLA.

In some embodiments, the isolated antibodies provided herein selectively bind to human BTLA glycosylated at N75, N94, N110 or any combination thereof, relative to unglycosylated BTLA. In some embodiments, the isolated antibodies selectively bind to human BTLA that has N75 glycosylation. In some embodiments, the isolated antibodies selectively bind to human BTLA that has N94 glycosylation. In some embodiments, the isolated antibodies selectively bind to human BTLA that has N110 glycosylation. In some embodiments, the isolated antibodies selectively bind to human BTLA that has N75 and N94 glycosylation. In some embodiments, the isolated antibodies selectively bind to human BTLA that has N94 and N110 glycosylation. In some embodiments, the isolated antibodies selectively bind to human BTLA that has N75 and N110 glycosylation. In some embodiments, the isolated antibodies selectively bind to human BTLA that has N75, N94 and N110 glycosylation.

In some embodiments, the isolated antibodies provided herein specifically mask a glycosylation motif of BTLA comprising BTLA positions N75, N94, N110, or any combination thereof. In some embodiments, the isolated antibodies specifically mask a glycosylation motif of BTLA comprising position N75 of human BTLA. In some embodiments, the isolated antibodies specifically mask a glycosylation motif of BTLA comprising position N94 of human BTLA. In some embodiments, the isolated antibodies specifically mask a glycosylation motif of BTLA comprising position N110 of human BTLA. In some embodiments, the isolated antibodies specifically mask a glycosylation motif of BTLA comprising positions N75 and N94 of human BTLA. In some embodiments, the isolated antibodies specifically mask a glycosylation motif of BTLA comprising positions N75 and N110 of human BTLA. In some embodiments, the isolated antibodies specifically mask a glycosylation motif of BTLA comprising positions N94 and N110 of human BTLA. In some embodiments, the isolated antibodies specifically mask a glycosylation motif of BTLA comprising positions N75, N94, and N110 of human BTLA.

In some embodiments, the antibodies provided herein selectively bind to one or more glycosylation motifs of BTLA. In some embodiments, the antibodies selectively binds to a glycopeptide having a glycosylation motif and the adjacent peptide. In some embodiments, the antibodies selectively bind to glycosylated BTLA with $K_D$ less than at least 30%, 40%, 50%, 60%, 70%, 80%, or 90% of the $K_D$ exhibited relative to unglycosylated BTLA. In certain embodiments, the antigen binding fragment binds to glycosylated BTLA with $K_D$ less than 50% of the $K_D$ exhibited relative to unglycosylated BTLA. In some embodiments, the antibodies bind to glycosylated BTLA with Kd that is less than 1%, 2%, 3%, 4%, 5%, 6%, 7%, 8%, 9%, 10%, 15%, 20%, 30%, 40%, 50% of the $K_D$ exhibited relative to unglycosylated BTLA. In further aspects, the antibodies bind to glycosylated BTLA with $K_D$ at least 10 times less than the $K_D$ exhibited relative to unglycosylated BTLA.

In some embodiments, selective binding of the antibodies provided herein to glycosylated BTLA relative to unglycosylated BTLA is determined using a fluorescence intensity (e.g., MFI) measurement, e.g., in a FACS assay or an ELISA. See, e.g., Examples 1 and 3. In some embodiments, the measured fluorescence intensity (e.g., MFI) indicates binding of a fluorescent labeled antibody provided herein (e.g., a FITC labeled antibody) to glycosylated or unglycosylated BTLA (e.g., cell surface expressed BTLA, BTLA immobilized on a surface or bead, or BTLA in bulk solution). In some embodiments, binding of the antibody to glycosylated BTLA is indicated in a fluorescence assay by an at least 2-fold, at least 3-fold, at least 4-fold, at least 5-fold, at least 6-fold, at least 7-fold, at least 8-fold, at least 9-fold, at least 10-fold, at least 12-fold, at least 14-fold, at least 16-fold, at least 18-fold, at least 20-fold, at least 25-fold, at least 30-fold, at least 35-fold, at least 40-fold, at least 45-fold, at least 50-fold, at least 60-fold, at least 70-fold, at least 80-fold, at least 90-fold, at least 100-fold, at least 120-fold, at least 140-fold, at least 160-fold, at least 180-fold, or at least 200-fold greater fluorescence intensity than the fluorescence intensity exhibited with unglycosylated BTLA. See, e.g., Table 10. In some embodiments, binding of the antibody to glycosylated BTLA is indicated in a fluorescence assay by an at least 2-fold, at least 3-fold, at least 4-fold, at least 5-fold, at least 6-fold, at least 7-fold, at least 8-fold, at least 9-fold, or at least 10-fold greater fluorescence intensity than the fluorescence intensity exhibited with unglycosylated BTLA. In some embodiments, binding of the antibody to glycosylated BTLA is indicated in a fluorescence assay by an at least 10-fold, at least 12-fold, at least 14-fold, at least 16-fold, at least 18-fold, or at least 20-fold greater fluorescence intensity than the fluorescence intensity exhibited with unglycosylated BTLA. In some embodiments, binding of the antibody to glycosylated BTLA is indicated in a fluorescence assay by an at least 10-fold, at least 20-fold, at least 25-fold, at least 30-fold, at least 35-fold, at least 40-fold, at least 45-fold, at least 50-fold, at least 60-fold, at least 70-fold, at least 80-fold, at least 90-fold, or at least 100-fold greater fluorescence intensity than the fluorescence intensity exhibited with unglycosylated BTLA. In some embodiments, binding of the antibody to glycosylated BTLA is indicated in a fluorescence assay by an at least 100-fold, at least 120-fold, at least 140-fold, at least 160-fold, at least 180-fold, or at least 200-fold greater fluorescence intensity than the fluorescence intensity exhibited with unglycosylated BTLA.

In some embodiments, the anti-glycosylated BTLA antibodies provided herein can be an IgG, IgM, IgA, IgD, or IgE. The anti-glycosylated BTLA antibody can also be a chimeric antibody, an affinity matured antibody, a humanized antibody, or a human antibody. The anti-glycosylated BTLA antibody can also be a camelized antibody, an intrabody, an anti-idiotypic (anti-Id) antibody. In some embodiments, the anti-glycosylated BTLA antibody can be a polyclonal antibody or monoclonal antibody.

In some embodiments, the antibodies provided herein are antigen binding fragments that selectively bind to glycosylated BTLA relative to unglycosylated BTLA. The antigen binding fragment can be Fd, Fv, Fab, F(ab'), F(ab)$_2$, F(ab')$_2$, F(ab)$_3$, F(ab')$_3$, single chain Fv (scFv), diabody, triabody, tetrabody, minibody, or a single domain antibody. A scFv can be a monovalent scFv, or a bivalent scFv.

Several exemplary mouse monoclonal antibodies (mAbs) that selectively bind to glycosylated BTLA relative to unglycosylated BTLA were produced and characterized. See, e.g., Examples 1-7. The exemplary anti-BTLA mAbs, include IgG1, IgG2A, IgG2B, IgG3 and IgGM isotypes. See, e.g., Table 8. The antibodies designated as STC604, STC605, STC606, STC608, STC610, STC613, STC618, STC622, STC626, STC627, STC628, STC630, and STC636, for example, show glycosylation-specific binding to BTLA. See, e.g., FIG. 1 and FIG. 2. The antibodies designated as STC604, STC610, STC613, STC618, STC622, STC626, and STC635, for example, bind BTLA with high affinity, with KDs ranging from 0.256 nM (STC613) to 5.61 nM (STC635). See, e.g., Table 11. The antibodies designated as STC613 and STC626, for example, inhibit BTLA binding to its natural ligand HVEM with IC50s of 1.088 µg/ml (STC613) and 0.416 µg/ml (STC626). See, e.g., FIG. 6. The BTLA epitope of one exemplary anti-BTLA mAb, designated as STC613, is also provided herein. Accordingly, provided herein are neutralizing anti-BTLA mAbs with specific sequence features, anti-BTLA mAbs that glycol-specifically bind BTLA, and specific BTLA epitopes, as well as uses thereof in cancer treatment.

In some embodiments, the anti-glycosylated BTLA antibodies provided herein comprise a VH region, VL region, VH CDR1, VH CDR2, VH CDR3, VL CDR1, VL CDR2, and/or VL CDR3 of any one of the monoclonal antibodies described herein (e.g., STC613, STC626, or STC635), such as an amino acid sequence depicted in Tables 2-7. Accordingly, in some embodiments, the antibodies provided herein comprise one, two, and/or three heavy chain CDRs and/or one, two, and/or three light chain CDRs from: (a) the antibody designated STC613; (b) the antibody designated STC626, or (c) the antibody designated STC635, as shown in Tables 3, 5, and 7.

The antibody designated STC613 comprises a VH sequence that is SEQ ID NO: 2 and a VL sequence that is SEQ ID NO:4.

The antibody designated STC626 comprises a VH sequence that is SEQ ID NO: 30 and a VL sequence that is SEQ ID NO: 32.

The antibody designated STC635 comprises a VH sequence that is SEQ ID NO: 58 and a VL sequence that is SEQ ID NO: 60.

TABLE 2

Sequences of heavy chain variable (VH) region and light chain variable (VL) region of mouse monoclonal anti-human BTLA antibody STC613

| | DNA sequence | Protein sequence |
|---|---|---|
| Heavy chain | GAGGTTCAGCTGCAGCAGTCTGGGGCTG AGCTTGTGAGGCCAGGGGCCTCAGTCA AGTTGTCCTGCACAGCTTCTGGCTTTAA CATTAGAGACGACTATGTGCACTGGTTG AAACAGAGGCCTGATCAGGGCCTGGAG TGGATTGGAAGGATTGATCCTGCGAATG GTAAAACTAAATATGACCCGAAGTTCCA GGACAAGGCCACTATAACTGCAGACAC ATCCTCCAACACAGCCTACCTGCAGCTC AGCAGCCTGACATCTGAGGACACTGCC GTCTATTTCTGTGTTAGAGAGGGGGTA GTAACTACGACTATGCTATGGACTACTG GGGTCAAGGAACCTCAGTCACCGTCTCC TCA (SEQ ID NO: 3) | EVQLQQSGAELVRPGASVKL SCTASGFNIRDDYVHWLKQR PDQGLEWIGRIDPANGKTKY DPKFQDKATITADTSSNTAYL QLSSLTSEDTAVYFCVREGGS NYDYAMDYWGQGTSVTVSS (SEQ ID NO: 2) |
| Kappa Light chain | GATGTTGTGATGACCCAGACTCCACTCA CTTTGTCGGTTACCATTGGACAACCAGC CTCCATCTCTTGCAAGTCAAGTCTGAGC CTCTTAGATAGTGATGGAAAGACATATT TGAATTGGTTGTTACAGAGGCCAGGCCA GTCTCCAAAGCGCCTAATCTATCTGGTG TCTAAACTGGACTCTGGAGTCCCTGACA GGTTCACTGGCAGTGGATCAGGGACAG ATTTCACACTGAAAATCAGCAGAGTGG AGGCTGAGGATGTGGGAGTTTATTATTG CTGGCAAGGTATTCATTTTCCTCGGACG TTCGGTGGAGGCACCAAGCTGGAAATC AAA (SEQ ID NO: 5) | DVVMTQTPLTLSVTIGQPASI SCKSSLSLLDSDGKTYLNWL LQRPGQSPKRLIYLVSKLDSG VPDRFTGSGSGTDFTLKISRV EAEDVGVYYCWQGIHFPRTF GGGTKLEIK (SEQ ID NO: 4) |

TABLE 3

CDR Sequences of mouse monoclonal anti-human BTLA antibody STC613

| | Region definition | CDR1 | CDR2 | CDR3 |
|---|---|---|---|---|
| Heavy chain | Chothia | GFNIRDD (SEQ ID NO: 6) | DPANGK (SEQ ID NO: 7) | EGGSNYDYAMDY (SEQ ID NO: 8) |
| | AbM | GFNIRDDYVH (SEQ ID NO: 9) | RIDPANGKTK (SEQ ID NO: 10) | EGGSNYDYAMDY (SEQ ID NO: 11) |
| | Kabat | DDYVH (SEQ ID NO: 12) | RIDPANGKTKYDP KFQD (SEQ ID NO: 13) | EGGSNYDYAMDY (SEQ ID NO: 14) |
| | Contact | RDDYVH (SEQ ID NO: 15) | WIGRIDPANGKTK (SEQ ID NO: 16) | VREGGSNYDYAMD (SEQ ID NO: 17) |

TABLE 3-continued

CDR Sequences of mouse monoclonal anti-human BTLA antibody STC613

| | Region definition | CDR1 | CDR2 | CDR3 |
|---|---|---|---|---|
| Kappa light chain | Chothia | KSSLSLLDSDGKT YLN (SEQ ID NO: 18) | LVSKLDS (SEQ ID NO: 19) | WQGIHFPRT (SEQ ID NO: 20) |
| | AbM | KSSLSLLDSDGKT YLN (SEQ ID NO: 21) | LVSKLDS (SEQ ID NO: 22) | WQGIHFPRT (SEQ ID NO: 23) |
| | Kabat | KSSLSLLDSDGKT YLN (SEQ ID NO: 24) | LVSKLDS (SEQ ID NO: 25) | WQGIHFPRT (SEQ ID NO: 26) |
| | Contact | LDSDGKTYLNWL (SEQ ID NO: 27) | RLIYLVSKLD (SEQ ID NO: 28) | WQGIHFPR (SEQ ID NO: 29) |

TABLE 4

Sequences of heavy chain variable (VH) region and light chain variable (VL) region of mouse monoclonal anti-human BTLA antibody STC626

| | DNA sequence | Protein sequence |
|---|---|---|
| Heavy chain | CAGATCCAGTTGGTGCAGTCTGGACCTG AGCTGAAGAAGCCTGGAGAGACAGTCA AGATCTCCTGCAAGGCTTCTGGGTATAC CTTCACAAACTATGGAATGAACTGGGTG AAGCAGGCTCCAGGAAAGGGTTTAAAG TGGATGGGCTGGATAAACACCAACACT GGAGAGCCAACATATGCTGAAGAGTTC AAGGGACGGATTGCCTTCTCTTTGGAAT CCTCTGCCAGCACTGCCTATTTGCAGAT CAACAACCTCAAAAATGAGGACACGGC CACATATTTCTGTGCAAGAGAGGGAGTG CGACGGGGGGGGTACTTTTTTGACTACT GGGGCCAAGGCACCACTCTCACAGTCTC CTCA (SEQ ID NO: 31) | QIQLVQSGPELKKPGETVKIS CKASGYTFTNYGMNWVKQA PGKGLKWMGWINTNTGEPT YAEEFKGRIAFSLESSASTAY LQINNLKNEDTATYFCAREG VRRGGYFFDYWGQGTTLTVS S (SEQ ID NO: 30) |
| Kappa Light chain | GACATCCAGATGACTCAGTCTCCAGCCT CCCTATCTGTATCTGTGGGAGAAACTGT CACCATCACATGTCGAGCAAGTGAGAA TATTTACAGCAATTTAGCATGGTATCAG CAGAAACAGGGAAAATCTCCTCAGCTC CTGGTCTATGCTGCAACAAACTTAGCAG ATGGTGTGCCATCAAGGTTCAGTGGCAG TGGATCAGGCACACAGTATTCCCTCAAG ATCAACAGCCTGCAGTCTGAAGATTTTG GGAGTTATCACTGTCAACATTTTTGGGG TTTTCCATTCACGTTCGGCGCGGGGACA AAGTTGGAAATAAAACGGGCT (SEQ ID NO: 33) | DIQMTQSPASLSVSVGETVTI TCRASENIYSNLAWYQQKQG KSPQLLVYAATNLADGVPSR FSGSGSGTQYSLKINSLQSED FGSYHCQHFWGFPFTFGAGT KLEIKRA (SEQ ID NO: 32) |

TABLE 5

CDR Sequences of mouse monoclonal anti-human BTLA antibody STC626

| | Region definition | CDR1 | CDR2 | CDR3 |
|---|---|---|---|---|
| Heavy chain | Chothia | GYTFTNY (SEQ ID NO: 34) | NTNTGE (SEQ ID NO: 35) | EGVRRGGYFFDY (SEQ ID NO: 36) |
| | AbM | GYTFTNYGMN (SEQ ID NO: 37) | WINTNTGEPT (SEQ ID NO: 38) | EGVRRGGYFFDY (SEQ ID NO: 39) |
| | Kabat | NYGMN (SEQ ID NO: 40) | WINTNTGEPTYAEE FKG (SEQ ID NO: 41) | EGVRRGGYFFDY (SEQ ID NO: 42) |

TABLE 5-continued

CDR Sequences of mouse monoclonal anti-human BTLA antibody STC626

| | Region definition | CDR1 | CDR2 | CDR3 |
|---|---|---|---|---|
| | Contact | TNYGMN (SEQ ID NO: 43) | WMGWINTNTGEPT (SEQ ID NO: 44) | AREGVRRGGYFFD (SEQ ID NO: 45) |
| Kappa light chain | Chothia | RASENIYSNLA (SEQ ID NO: 46) | AATNLAD (SEQ ID NO: 47) | QHFWGFPFT (SEQ ID NO: 48) |
| | AbM | RASENIYSNLA (SEQ ID NO: 49) | AATNLAD (SEQ ID NO: 50) | QHFWGFPFT (SEQ ID NO: 51) |
| | Kabat | RASENIYSNLA (SEQ ID NO: 52) | AATNLAD (SEQ ID NO: 53) | QHFWGFPFT (SEQ ID NO: 54) |
| | Contact | YSNLAWY (SEQ ID NO: 55) | LLVYAATNLA (SEQ ID NO: 56) | QHFWGFPF (SEQ ID NO: 57) |

TABLE 6

Sequences of heavy chain variable (VH) region and light chain variable (VL) region of mouse monoclonal anti-human BTLA antibody STC635

| | DNA sequence | Protein sequence |
|---|---|---|
| Heavy chain | GAGGTTCAGCTGCAGCAGTCTGGGCA GAGCTTGTGAAGCCAGGGGCCTCAGTC AAGTTGTCCTGCACAGCTTCTGGCTTCA ACATTAAAGACACCTATATGCACTGGGT GAGGCAGAGGCCTGAACAGGGCCTGGA GTGGATTGGAAGGATTGATCCTGCGAAT GGTTATACTAAATATGACCCGAAGTTCC AGGGCAAGGCCACTATAACAGCAGACA CATCCTCCAACACAGCCTACCTGCAGCT CAGCAGCCTGACATCTGAGGACACTGCC GTCTATTACTGTCTCATCTATGATGGTTA CTACGACTCCTTTGACTACTGGGGCCAA GGCACCACTCTCACAGTCTCCTCA (SEQ ID NO: 59) | EVQLQQSGAELVKPGASVKL SCTASGFNIKDTYMHWVRQR PEQGLEWIGRIDPANGYTKY DPKFQGKATITADTSSNTAYL QLSSLTSEDTAVYYCLIYDGY YDSFDYWGQGTTLTVSS (SEQ ID NO: 58) |
| Kappa Light chain | GATGTTGTGATGACCCAGACTCCACTCA CTTTGTCGGTTCCCATTGGACAACCAGC CTCCATCTCTTGCAAGTCAAGTCAGAGC CTCTTAGATAGTGATGGAAAGACATATT TGAATTGGTTGTTACAGAGGCCAGGCCA GTCTCCAAAGCGCCTAATCTATCTGGTG TCTAAACTGGACTCTGGAGTCCCTGACA GGTTCACTGGCAGTGGATCAGGGACAG ATTTCACACTGAAAATCAGCAGAGTGG AGGCTGAGGATTTGGGAGTTTATTATTG CTGGCAAGTTACACATTTTCCTCGGACG TTCGGTGGAGGCACCAAGCTGGAAATC AAA (SEQ ID NO: 61) | DVVMTQTPLTLSVPIGQPASI SCKSSQSLLDSDGKTYLNWL LQRPGQSPKRLIYLVSKLDSG VPDRFTGSGSGTDFTLKISRV EAEDLGVYYCWQVTHFPRTF GGGTKLEIK (SEQ ID NO: 60) |

TABLE 7

CDR Sequences of mouse monoclonal anti-human BTLA antibody STC635

| | Region definition | CDR1 | CDR2 | CDR3 |
|---|---|---|---|---|
| Heavy chain | Chothia | GFNIKDT (SEQ ID NO: 62) | DPANGY (SEQ ID NO: 63) | YDGYYDSFDY (SEQ ID NO: 64) |
| | AbM | GFNIKDTYMH (SEQ ID NO: 65) | RIDPANGYTK (SEQ ID NO: 66) | YDGYYDSFDY (SEQ ID NO: 67) |
| | Kabat | DTYMH (SEQ ID NO: 68) | RIDPANGYTKYDP KFQG (SEQ ID NO: 69) | YDGYYDSFDY (SEQ ID NO: 70) |

TABLE 7-continued

CDR Sequences of mouse monoclonal anti-human BTLA antibody STC635

|  | Region definition | CDR1 | CDR2 | CDR3 |
|---|---|---|---|---|
|  | Contact | KDTYMH (SEQ ID NO: 71) | WIGRIDPANGYTK (SEQ ID NO: 72) | LIYDGYYDSFD (SEQ ID NO: 73) |
| Kappa light chain | Chothia | KSSQSLLDSDGKT YLN (SEQ ID NO: 74) | LVSKLDS (SEQ ID NO: 75) | WQVTHFPRT (SEQ ID NO: 76) |
|  | AbM | KSSQSLLDSDGKT YLN (SEQ ID NO: 77) | LVSKLDS (SEQ ID NO: 78) | WQVTHFPRT (SEQ ID NO: 79) |
|  | Kabat | KSSQSLLDSDGKT YLN (SEQ ID NO: 80) | LVSKLDS (SEQ ID NO: 81) | WQVTHFPRT (SEQ ID NO: 82) |
|  | Contact | LDSDGKTYLNWL (SEQ ID NO: 83) | RLIYLVSKLD (SEQ ID NO: 84) | WQVTHFPR (SEQ ID NO: 85) |

In some embodiments, the anti-glycosylated BTLA antibodies provided herein comprise a VH region or VH domain. In other embodiments, the antibodies provided herein comprise a VL region or VL chain. In some embodiments, the antibodies provided herein have a combination of (i) a VH domain or VH region; and/or (ii) a VL domain or VL region.

In some embodiments, the anti-glycosylated BTLA antibodies provided herein comprises or consists of six CDRs, for example, VH CDR1, VH CDR2, VH CDR3, VL CDR1, VL CDR2, and/or VL CDR3 identified in Tables 3, 5, or 7. In some embodiments, the antibodies provided herein can comprise less than six CDRs. In some embodiments, the antibodies comprise or consists of one, two, three, four, or five CDRs selected from the group consisting of VH CDR1, VH CDR2, VH CDR3, VL CDR1, VL CDR2, and/or VL CDR3 identified in Tables 3, 5, or 7. In some embodiments, the antibodies comprise or consists of one, two, three, four, or five CDRs selected from the group consisting of VH CDR1, VH CDR2, VH CDR3, VL CDR1, VL CDR2, and/or VL CDR3 of the murine monoclonal antibody selected from the group consisting of: (a) the antibody designated STC613; (b) the antibody designated STC626; or (c) the antibody designated STC635 described herein. Accordingly, in some embodiments, the antibodies comprise or consists of one, two, three four or five CDRs of anyone of the VH CDR1, VH CDR2, VH CDR3, VL CDR1, VL CDR2, and/or VL CDR3 identified in Tables 3, 5, or 7.

In some embodiments, the antibodies provided herein comprise one or more (e.g., one, two or three) VH CDRs listed in Tables 3, 5, or 7. In other embodiments, the antibodies provided herein comprise one or more (e.g., one, two or three) VL CDRs listed in Tables 3, 5, or 7. In yet other embodiments, the antibodies provided herein comprise one or more (e.g., one, two or three) VH CDRs listed in Tables 3, 5, and 7 and one or more VL CDRs listed in Tables 3, 5, or 7. Accordingly, in certain embodiments, the antibodies comprise a VH CDR1 having the amino acid sequence of any one of SEQ ID NOS: 6, 9, 12, 15, 34, 37, 40, 43, 62, 65, 68, or 71. In another embodiment, the antibodies comprise a VH CDR2 having the amino acid sequence of any one of SEQ ID NOS: 7, 10, 13, 16, 35, 38, 41, 44, 63, 66, 69, or 72. In another embodiment, the antibodies comprise a VH CDR3 having the amino acid sequence of any one of SEQ ID NOS: 8, 11, 14, 17, 36, 39, 42, 45, 64, 67, 70, or 73. In certain embodiments, the antibodies comprise a VH CDR1 and/or a VH CDR2 and/or a VH CDR3 independently selected from a VH CDR1, VH CDR2, VH CDR3 as depicted in any one of the amino acid sequences depicted in Table 3, 5, or 7. In certain embodiments, the antibodies comprise a VL CDR1 having the amino acid sequence of any one of SEQ ID NOS: 18, 21, 24, 27, 46, 49, 52, 55, 74, 77, 80, or 83. In another embodiment, the antibodies comprise a VL CDR2 having the amino acid sequence of any one of SEQ ID NOS: 19, 22, 25, 28, 47, 50, 53, 56, 75, 78, 81, or 84. In another embodiment, the antibodies comprise a VL CDR3 having the amino acid sequence of any one of SEQ ID NOS: 20, 23, 26, 29, 48, 51, 54, 57, 76, 79, 82, or 85. In certain embodiments, the antibodies comprise a VL CDR1 and/or a VL CDR2 and/or a VL CDR3 independently selected from a VL CDR1, VL CDR2, VL CDR3 as depicted in any one of the amino acid sequences depicted in Tables 3, 5, or 7.

In some embodiments, the antibodies provided herein comprise a heavy chain variable (VH) region comprising: (1) a VH CDR1 having an amino acid sequence selected from the group consisting of: (i) SEQ ID NO: 6, 34, or 62, (ii) SEQ ID NO: 9, 37, or 65, (iii) SEQ ID NO: 12, 40, or 68, and (iv) SEQ ID NO: 15, 43, or 71; (2) a VH CDR2 having an amino acid sequence selected from the group consisting of: (i) SEQ ID NO: 7, 35, or 63, (ii) SEQ ID NO: 10, 38, or 66, (iii) SEQ ID NO: 13, 41, or 69, and (iv) SEQ ID NO: 16, 44, or 72; and (3) a VH CDR3 having an amino acid sequence selected from the group consisting of: (i) SEQ ID NO: 8, 36, or 64; (ii) SEQ ID NO: 11, 39, or 67; (iii) SEQ ID NO: 14, 42, or 70, and (iv) SEQ ID NO: 17, 45, or 73; and/or a light chain variable (VL) region comprising: (1) a VL CDR1 having an amino acid sequence selected from the group consisting of: (i) SEQ ID NO: 18, 46, or 74; (ii) SEQ ID NO: 21, 49, or 77; (iii) SEQ ID NO: 24, 52, or 80, and (iv) SEQ ID NO: 27, 55, or 83; (2) a VL CDR2 having an amino acid sequence selected from the group consisting of: (i) SEQ ID NO: 19, 47, or 75; (ii) SEQ ID NO: 22, 50, or 78; (iii) SEQ ID NO: 25, 53, or 81, and (iv) SEQ ID NO: 28, 56, or 84; and (3) a VL CDR3 having an amino acid sequence selected from the group consisting of: (i) SEQ ID NO: 20, 48, or 76; (ii) SEQ ID NO: 23, 51, or 79; (iii) SEQ ID NO: 26, 54, or 82; and (iv) SEQ ID NO: 29, 57, or 85.

In some embodiments, the antibodies provided herein comprise a heavy chain variable (VH) region comprising: (1) a VH CDR1 having an amino acid sequence selected from the group consisting of: (i) SEQ ID NO: 6, 34, or 62, (ii) SEQ ID NO: 9, 37, or 65, (iii) SEQ ID NO: 12, 40, or 68, and (iv) SEQ ID NO: 15, 43, or 71; (2) a VH CDR2 having an amino acid sequence selected from the group consisting of: (i) SEQ ID NO: 7, 35, or 63, (ii) SEQ ID NO: 10, 38, or 66, (iii) SEQ ID NO: 13, 41, or 69, and (iv) SEQ ID NO: 16, 44, or 72; and (3) a VH CDR3 having an amino acid sequence selected from the group consisting of: (i) SEQ ID NO: 8, 36, or 64; (ii) SEQ ID NO: 11, 39, or 67; (iii) SEQ ID NO: 14, 42, or 70, and (iv) SEQ ID NO: 17, 45, or 73.

In some embodiments, the antibodies provided herein comprise a light chain variable (VL) region comprising: (1) a VL CDR1 having an amino acid sequence selected from the group consisting of: (i) SEQ ID NO: 18, 46, or 74; (ii) SEQ ID NO: 21, 49, or 77; (iii) SEQ ID NO: 24, 52, or 80, and (iv) SEQ ID NO: 27, 55, or 83; (2) a VL CDR2 having an amino acid sequence selected from the group consisting of: (i) SEQ ID NO: 19, 47, or 75, (ii) SEQ ID NO: 22, 50, or 78, (iii) SEQ ID NO: 25, 53, or 81, and (iv) SEQ ID NO: 28, 56, or 84; and (3) a VL CDR3 having an amino acid sequence selected from the group consisting of: (i) SEQ ID NO: 20, 48, or 76, (ii) SEQ ID NO: 23, 51, or 79, (iii) SEQ ID NO: 26, 54, or 82, and (iv) SEQ ID NO: 29, 57, or 85.

Also provided herein are antibodies comprising one or more (e.g., one, two or three) VH CDRs and one or more (e.g., one, two or three) VL CDRs listed in Tables 3, 5, or 7. In particular, provided herein is an antibody comprising: a VH CDR1 (SEQ ID NOS: 6, 9, 12, 15, 34, 37, 40, 43, 62, 65, 68, or 71) and a VL CDR1 (SEQ ID NOS: 18, 21, 24, 27, 46, 49, 52, 55, 74, 77, 80, or 83); a VH CDR1 (SEQ ID NOS: 6, 9, 12, 15, 34, 37, 40, 43, 62, 65, 68, or 71) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71) and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72) and a VL CDR1 (SEQ ID NOS: 18, 21, 24, 27, 46, 49, 52, 55, 74, 77, 80, or 83); a VH CDR2 (SEQ ID NOS: 7, 10, 13, 16, 35, 38, 41, 44, 63, 66, 69, or 72) and a VL CDR2 (SEQ ID NOS: 19, 22, 25, 28, 47, 50, 53, 56, 75, 78, 81, or 84); a VH CDR2 (SEQ ID NOS: 7, 10, 13, 16, 35, 38, 41, 44, 63, 66, 69, or 72) and a VL CDR3 (SEQ ID NOS: 20, 23, 26, 29, 48, 51, 54, 57, 76, 79, 82, or 85); a VH CDR3 (SEQ ID NOS: 8, 11, 14, 17, 36, 39, 42, 45, 64, 67, 70, or 73) and a VL CDR1 (SEQ ID NOS: 18, 21, 24, 27, 46, 49, 52, 55, 74, 77, 80, or 83); a VH CDR3 (SEQ ID NOS: 8, 11, 14, 17, 36, 39, 42, 45, 64, 67, 70, or 73) and a VL CDR2 (SEQ ID NOS: 19, 22, 25, 28, 47, 50, 53, 56, 75, 78, 81, or 84); a VH CDR3 (SEQ ID NOS: 8, 11, 14, 17, 36, 39, 42, 45, 64, 67, 70, or 73) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72) and a VL CDR1 (SEQ ID NOS: 18, 21, 24, 27, 46, 49, 52, 55, 74, 77, 80, or 83); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72) and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73) and a VL CDR1 (SEQ ID NOS: 18, 21, 24, 27, 46, 49, 52, 55, 74, 77, 80, or 83); a VH CDR2 (SEQ ID NOS: 7, 10, 13, 16, 35, 38, 41, 44, 63, 66, 69, or 72); a VH CDR3 (SEQ ID NOS: 8, 11, 14, 17, 36, 39, 42, 45, 64, 67, 70, or 73) and a VL CDR2 (SEQ ID NOS: 19, 22, 25, 28, 47, 50, 53, 56, 75, 78, 81, or 84); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VL CDR1 (SEQ ID NOS: 18, 21, 24, 27, 46, 49, 52, 55, 74, 77, 80, or 83) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71), a VL CDR1 (SEQ ID NOS: 18, 21, 24, 27, 46, 49, 52, 55, 74, 77, 80, or 83) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VL CDR2 (SEQ ID NOS: 19, 22, 25, 28, 47, 50, 53, 56, 75, 78, 81, or 84) and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72), a VL CDR1 (SEQ ID NOS: 18, 21, 24, 27, 46, 49, 52, 55, 74, 77, 80, or 83) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72), a VL CDR1 (SEQ ID NOS: 18, 21, 24, 27, 46, 49, 52, 55, 74, 77, 80, or 83) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72), a VL CDR2 (SEQ ID NOS: 19, 22, 25, 28, 47, 50, 53, 56, 75, 78, 81, or 84) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR3 (SEQ ID NOS: 8, 11, 14, 17, 36, 39, 42, 45, 64, 67, 70, or 73), a VL CDR2 (SEQ ID NOS: 19, 22, 25, 28, 47, 50, 53, 56, 75, 78, 81, or 84) and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83) and a VL CDR2 (SEQ ID NOS: 19, 22, 25, 28, 47, 50, 53, 56, 75, 78, 81, or 84); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83) and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR2 (SEQ ID NOS: 19, 22, 25, 28, 47, 50, 53, 56, 75, 78, 81, or 84) and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83) and a VL CDR2 (SEQ ID NOS: 19, 22, 25, 28, 47, 50, 53, 56, 75, 78, 81, or 84); a VH CDR1 (SEQ ID NOS: 6, 9, 12, 15, 34, 37, 40, 43, 62, 65, 68, or 71), a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83), a VL CDR2 (SEQ ID NOS: 19, 22, 25, 28, 47, 50, 53, 56, 75, 78, 81, or 84), and a VL CDR3 (SEQ ID NOS: 20, 23, 26, 29, 48, 51, 54, 57, 76, 79, 82, or 85); a VH CDR1 (SEQ ID NOS: 6, 9, 12, 15, 34, 37, 40, 43, 62, 65, 68, or 71), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83), a VL CDR2 (SEQ ID NOS: 19, 22, 25, 28, 47, 50, 53, 56, 75, 78, 81, or 84), and a VL CDR3 (SEQ ID NOS: 20, 23, 26, 29, 48, 51, 54, 57, 76, 79, 82, or 85); a VH CDR2 (SEQ ID NOS: 7, 10, 13, 16, 35, 38, 41, 44, 63, 66, 69, or 72), a VH CDR3 (SEQ ID NOS: 8, 11, 14, 17, 36, 39, 42, 45, 64, 67, 70, or 73), a VL CDR1 (SEQ ID NOS: 18, 21, 24, 27, 46, 49, 52, 55, 74, 77, 80, or 83), a VL CDR2 (SEQ ID NOS: 19, 22, 25, 28, 47, 50, 53, 56, 75, 78, 81, or 84), and a VL CDR3 (SEQ ID NOS: 20, 23, 26, 29, 48, 51, 54, 57, 76, 79, 82, or 85); or any combination thereof of the VH CDRs (SEQ ID NOS: 6, 7, 8, 9, 10, 11, 12, 13, 14, 15, 16, 17, 34, 35, 36, 37, 38, 39, 40, 41, 42, 43, 44, 45, 62, 63, 64, 65, 66, 67, 68, 69, 70, 71, 72, or 73) and VL CDRs (SEQ ID NOS: 18, 19, 20, 21, 22, 23, 24, 25, 26, 27, 28, 29, 46, 47, 48, 49, 50, 51, 52, 53, 54, 55, 56, 57, 74, 75, 76, 77, 78, 79, 80, 81, 82, 83, 84, or 85) listed in Tables 3, 5, and 7.

In some embodiments, the antibodies provided herein have a heavy chain variable (VH) region comprising: (1) a VH CDR1 comprising an amino acid sequence of SEQ ID NOS: 6, 9, 12, 15, 34, 37, 40, 43, 62, 65, 68, or 71; (2) a VH CDR2 comprising an amino acid sequence of SEQ ID NOS: 7, 10, 13, 16, 35, 38, 41, 44, 63, 66, 69, or 72; and/or (3) a VH CDR3 comprising an amino acid sequence of SEQ ID NOS: 8, 11, 14, 17, 36, 39, 42, 45, 64, 67, 70, or 73. In some embodiments, the heavy chain variable (VH) region comprises (1) a VH CDR1 comprising an amino acid sequence of SEQ ID NOS: 6, 9, 12, 15, 34, 37, 40, 43, 62, 65, 68, or 71; and (2) a VH CDR2 comprising an amino acid sequence of SEQ ID NOS: 7, 10, 13, 16, 35, 38, 41, 44, 63, 66, 69, or 72. In some embodiments, the heavy chain variable (VH) region comprises (1) a VH CDR1 comprising an amino acid sequence of SEQ ID NOS: 6, 9, 12, 15, 34, 37, 40, 43, 62, 65, 68, or 71; and (3) a VH CDR3 comprising an amino acid sequence of SEQ ID NOS: 8, 11, 14, 17, 36, 39, 42, 45, 64, 67, 70, or 73. In some embodiments, the antibodies provided herein have a heavy chain variable (VH) region comprising: (1) a VH CDR2 comprising an amino acid sequence of SEQ ID NOS: 7, 10, 13, 16, 35, 38, 41, 44, 63, 66, 69, or 72; and (3) a VH CDR3 comprising an amino acid sequence of SEQ ID NOS: 8, 11, 14, 17, 36, 39, 42, 45, 64, 67, 70, or 73.

In some embodiments, the antibodies provided herein comprise a heavy chain variable (VH) region having a VH CDR1 comprising an amino acid sequence of SEQ ID NOS: 6, 9, 12, 15, 34, 37, 40, 43, 62, 65, 68, or 71. The VH CDR1 can comprise an amino acid sequence of SEQ ID NO: 6. The VH CDR1 can comprise an amino acid sequence of SEQ ID NO: 9. The VH CDR1 can comprise an amino acid sequence of SEQ ID NO: 12. The VH CDR1 can comprise an amino acid sequence of SEQ ID NO: 15. The VH CDR1 can comprise an amino acid sequence of SEQ ID NO: 34. The VH CDR1 can comprise an amino acid sequence of SEQ ID NO: 37. The VH CDR1 can comprise an amino acid sequence of SEQ ID NO: 40. The VH CDR1 can comprise an amino acid sequence of SEQ ID NO: 43. The VH CDR1 can comprise an amino acid sequence of SEQ ID NO: 62. The VH CDR1 can comprise an amino acid sequence of SEQ ID NO: 65. The VH CDR1 can comprise an amino acid sequence of SEQ ID NO: 68. The VH CDR1 can comprise an amino acid sequence of SEQ ID NO: 71.

In some embodiments, the antibodies provided herein comprise a heavy chain variable (VH) region having a VH CDR2 comprising an amino acid sequence of SEQ ID NOS: 7, 10, 13, 16, 35, 38, 41, 44, 63, 66, 69, or 72. The VH CDR2 can comprise an amino acid sequence of SEQ ID NO: 7. The VH CDR2 can comprise an amino acid sequence of SEQ ID NO: 10. The VH CDR2 can comprise an amino acid sequence of SEQ ID NO: 13. The VH CDR2 can comprise an amino acid sequence of SEQ ID NO: 16. The VH CDR2 can comprise an amino acid sequence of SEQ ID NO: 35. The VH CDR2 can comprise an amino acid sequence of SEQ ID NO: 38. The VH CDR2 can comprise an amino acid sequence of SEQ ID NO: 41. The VH CDR2 can comprise an amino acid sequence of SEQ ID NO: 44. The VH CDR2 can comprise an amino acid sequence of SEQ ID NO: 63. The VH CDR2 can comprise an amino acid sequence of SEQ ID NO: 66. The VH CDR2 can comprise an amino acid sequence of SEQ ID NO: 69. The VH CDR2 can comprise an amino acid sequence of SEQ ID NO: 72.

In some embodiments, the antibodies provided herein have a heavy chain variable (VH) region having a VH CDR3 comprising an amino acid sequence of SEQ ID NOS: 8, 11, 14, 17, 36, 39, 42, 45, 64, 67, 70, or 73. The VH CDR3 can comprise an amino acid sequence of SEQ ID NO: 8. The VH CDR3 can comprise an amino acid sequence of SEQ ID NO: 11. The VH CDR3 can comprise an amino acid sequence of SEQ ID NO: 14. The VH CDR3 can comprise an amino acid sequence of SEQ ID NO: 17. The VH CDR3 can comprise an amino acid sequence of SEQ ID NO: 36. The VH CDR3 can comprise an amino acid sequence of SEQ ID NO: 39. The VH CDR3 can comprise an amino acid sequence of SEQ ID NO: 42. The VH CDR3 can comprise an amino acid sequence of SEQ ID NO: 45. The VH CDR3 can comprise an amino acid sequence of SEQ ID NO: 64. The VH CDR3 can comprise an amino acid sequence of SEQ ID NO: 67. The VH CDR3 can comprise an amino acid sequence of SEQ ID NO: 70. The VH CDR3 can comprise an amino acid sequence of SEQ ID NO: 73.

In some embodiments, the antibodies provided herein have a heavy chain variable (VH) region comprising: (1) a VH CDR1 comprising an amino acid sequence of SEQ ID NO: 6; (2) a VH CDR2 comprising an amino acid sequence of SEQ ID NO: 7; and/or (3) a VH CDR3 comprising an amino acid sequence of SEQ ID NO: 8.

In some embodiments, the antibodies provided herein have a heavy chain variable (VH) region comprising: (1) a VH CDR1 comprising an amino acid sequence of SEQ ID NO: 9; (2) a VH CDR2 comprising an amino acid sequence of SEQ ID NO: 10; and/or (3) a VH CDR3 comprising an amino acid sequence of SEQ ID NO: 11.

In some embodiments, the antibodies provided herein have a heavy chain variable (VH) region comprising: (1) a VH CDR1 comprising an amino acid sequence of SEQ ID NO: 12; (2) a VH CDR2 comprising an amino acid sequence of SEQ ID NO: 13; and/or (3) a VH CDR3 comprising an amino acid sequence of SEQ ID NO: 14.

In some embodiments, the antibodies provided herein have a heavy chain variable (VH) region comprising: (1) a VH CDR1 comprising an amino acid sequence of SEQ ID NO: 15; (2) a VH CDR2 comprising an amino acid sequence of SEQ ID NO: 16; and/or (3) a VH CDR3 comprising an amino acid sequence of SEQ ID NO: 17.

In some embodiments, the antibodies provided herein have an antigen binding fragment that has a heavy chain variable (VH) region comprising: (1) a VH CDR1 having an amino acid sequence of SEQ ID NO: 34; (2) a VH CDR2 having an amino acid sequence of SEQ ID NO: 35; and/or (3) a VH CDR3 having an amino acid sequence of SEQ ID NO: 36.

In some embodiments, the antibodies provided herein have a heavy chain variable (VH) region comprising: (1) a VH CDR1 comprising an amino acid sequence of SEQ ID NO: 37; (2) a VH CDR2 comprising an amino acid sequence of SEQ ID NO: 38; and/or (3) a VH CDR3 comprising an amino acid sequence of SEQ ID NO: 39.

In some embodiments, the antibodies provided herein have a heavy chain variable (VH) region comprising: (1) a VH CDR1 comprising an amino acid sequence of SEQ ID NO: 40; (2) a VH CDR2 comprising an amino acid sequence of SEQ ID NO: 41; and/or (3) a VH CDR3 comprising an amino acid sequence of SEQ ID NO: 42.

In some embodiments, the antibodies provided herein have a heavy chain variable (VH) region comprising: (1) a VH CDR1 comprising an amino acid sequence of SEQ ID NO: 43; (2) a VH CDR2 comprising an amino acid sequence of SEQ ID NO: 44; and/or (3) a VH CDR3 comprising an amino acid sequence of SEQ ID NO: 45.

In some embodiments, the antibodies provided herein have a heavy chain variable (VH) region comprising: (1) a VH CDR1 comprising an amino acid sequence of SEQ ID NO: 62; (2) a VH CDR2 comprising an amino acid sequence of SEQ ID NO: 63; and/or (3) a VH CDR3 comprising an amino acid sequence of SEQ ID NO: 64.

In some embodiments, the antibodies provided herein have a heavy chain variable (VH) region comprising: (1) a VH CDR1 comprising an amino acid sequence of SEQ ID NO: 65; (2) a VH CDR2 comprising an amino acid sequence of SEQ ID NO: 66; and/or (3) a VH CDR3 comprising an amino acid sequence of SEQ ID NO: 67.

In some embodiments, the antibodies provided herein have a heavy chain variable (VH) region comprising: (1) a VH CDR1 comprising an amino acid sequence of SEQ ID NO: 68; (2) a VH CDR2 comprising an amino acid sequence of SEQ ID NO: 69; and/or (3) a VH CDR3 comprising an amino acid sequence of SEQ ID NO: 70.

In some embodiments, the antibodies provided herein have a heavy chain variable (VH) region comprising: (1) a VH CDR1 comprising an amino acid sequence of SEQ ID NO: 71; (2) a VH CDR2 comprising an amino acid sequence of SEQ ID NO: 72; and/or (3) a VH CDR3 comprising an amino acid sequence of SEQ ID NO: 73.

In some embodiments, the antibodies provided herein have a heavy chain variable (VH) region that comprises the amino acid sequence of SEQ ID NO: 2. The antibody can be a monoclonal antibody. The antibody can be a humanized antibody.

In some embodiments, the antibodies provided herein have a heavy chain variable (VH) region that comprises the amino acid sequence of SEQ ID NO: 30. The antibody can be a monoclonal antibody. The antibody can be a humanized antibody.

In some embodiments, the antibodies provided herein have a heavy chain variable (VH) region that comprises the amino acid sequence of SEQ ID NO: 58. The antibody can be a monoclonal antibody. The antibody can be a humanized antibody.

In some embodiments, the antibodies provided herein have a light chain variable (VL) region comprising: (1) a VL CDR1 comprising an amino acid sequence of SEQ ID NOS: 18, 21, 24, 27, 46, 49, 52, 55, 74, 77, 80, or 83; and (2) a VL CDR2 comprising an amino acid sequence of SEQ ID NOS: 19, 22, 25, 28, 47, 50, 53, 56, 75, 78, 81, or 84. In some embodiments, the antibodies provided herein have a light chain variable (VL) region comprising: (1) a VL CDR1 comprising an amino acid sequence of SEQ ID NOS: 18, 21, 24, 27, 46, 49, 52, 55, 74, 77, 80, or 83; and (3) a VL CDR3 comprising an amino acid sequence of SEQ ID NOS: 20, 23, 26, 29, 48, 51, 54, 57, 76, 79, 82, or 85. In some embodiments, the antibodies provided herein have a light chain variable (VL) region comprising: (2) a VL CDR2 comprising an amino acid sequence of SEQ ID NOS: 19, 22, 25, 28, 47, 50, 53, 56, 75, 78, 81, or 84; and (3) a VL CDR3 comprising an amino acid sequence of SEQ ID NOS: 20, 23, 26, 29, 48, 51, 54, 57, 76, 79, 82, or 85.

In some embodiments, the antibodies provided herein have a light chain variable (VL) region having a VL CDR1 comprising an amino acid sequence of SEQ ID NOS: 18, 21, 24, 27, 46, 49, 52, 55, 74, 77, 80, or 83. The VL CDR1 can comprising an amino acid sequence of SEQ ID NO: 18. The VL CDR1 can comprising an amino acid sequence of SEQ ID NO: 21. The VL CDR1 can comprising an amino acid sequence of SEQ ID NO: 24. The VL CDR1 can comprising an amino acid sequence of SEQ ID NO: 27. The VL CDR1 can comprising an amino acid sequence of SEQ ID NO: 46. The VL CDR1 can comprising an amino acid sequence of SEQ ID NO: 49. The VL CDR1 can comprising an amino acid sequence of SEQ ID NO: 52. The VL CDR1 can comprising an amino acid sequence of SEQ ID NO: 55. The VL CDR1 can comprising an amino acid sequence of SEQ ID NO: 74. The VL CDR1 can comprising an amino acid sequence of SEQ ID NO: 77. The VL CDR1 can comprising an amino acid sequence of SEQ ID NO: 80. The VL CDR1 can comprising an amino acid sequence of SEQ ID NO: 83.

In some embodiments, the antibodies provided herein have a light chain variable (VL) region having a VL CDR2 comprising an amino acid sequence of SEQ ID NOS: 19, 22, 25, 28, 47, 50, 53, 56, 75, 78, 81, or 84. The VL CDR2 can comprise an amino acid sequence of SEQ ID NO: 19. The VL CDR2 can comprise an amino acid sequence of SEQ ID NO: 22. The VL CDR2 can comprise an amino acid sequence of SEQ ID NO: 25. The VL CDR2 can comprise an amino acid sequence of SEQ ID NO: 28. The VL CDR2 can comprise an amino acid sequence of SEQ ID NO: 47. The VL CDR2 can comprise an amino acid sequence of SEQ ID NO: 50. The VL CDR2 can comprise an amino acid sequence of SEQ ID NO: 53. The VL CDR2 can comprise an amino acid sequence of SEQ ID NO: 56. The VL CDR2 can comprise an amino acid sequence of SEQ ID NO: 75. The VL CDR2 can comprise an amino acid sequence of SEQ ID NO: 78. The VL CDR2 can comprise an amino acid sequence of SEQ ID NO: 81. The VL CDR2 can comprise an amino acid sequence of SEQ ID NO: 84.

In some embodiments, the antibodies provided herein have a light chain variable (VL) region having a VL CDR3 comprising an amino acid sequence of SEQ ID NOS: 20, 23, 26, 29, 48, 51, 54, 57, 76, 79, 82, or 85. The VL CDR3 can comprise an amino acid sequence of SEQ ID NO: 20. The VL CDR3 can comprise an amino acid sequence of SEQ ID NO: 23. The VL CDR3 can comprise an amino acid sequence of SEQ ID NO: 26. The VL CDR3 can comprise an amino acid sequence of SEQ ID NO: 29. The VL CDR3 can comprise an amino acid sequence of SEQ ID NO: 48. The VL CDR3 can comprise an amino acid sequence of SEQ ID NO: 51. The VL CDR3 can comprise an amino acid sequence of SEQ ID NO: 54. The VL CDR3 can comprise an amino acid sequence of SEQ ID NO: 57. The VL CDR3 can comprise an amino acid sequence of SEQ ID NO: 76. The VL CDR3 can comprise an amino acid sequence of SEQ ID NO: 79. The VL CDR3 can comprise an amino acid sequence of SEQ ID NO: 82. The VL CDR3 can comprise an amino acid sequence of SEQ ID NO: 85.

In some embodiments, the antibodies provided herein have a light chain variable (VL) region that has (1) a VL CDR1 comprising an amino acid sequence of SEQ ID NO: 18; (2) a VL CDR2 comprising an amino acid sequence of SEQ ID NO: 19; and/or (3) a VL CDR3 comprising an amino acid sequence of SEQ ID NO: 20.

In some embodiments, the antibodies provided herein have a light chain variable (VL) region that has (1) a VL CDR1 comprising an amino acid sequence of SEQ ID NO: 21; (2) a VL CDR2 comprising an amino acid sequence of SEQ ID NO: 22; and/or (3) a VL CDR3 comprising an amino acid sequence of SEQ ID NO: 23.

In some embodiments, the antibodies provided herein have a light chain variable (VL) region that has (1) a VL CDR1 comprising an amino acid sequence of SEQ ID NO: 24; (2) a VL CDR2 comprising an amino acid sequence of SEQ ID NO: 25; and/or (3) a VL CDR3 comprising an amino acid sequence of SEQ ID NO: 26.

In some embodiments, the antibodies provided herein have a light chain variable (VL) region that has (1) a VL CDR1 comprising an amino acid sequence of SEQ ID NO: 27; (2) a VL CDR2 comprising an amino acid sequence of SEQ ID NO: 28; and/or (3) a VL CDR3 comprising an amino acid sequence of SEQ ID NO: 29.

In some embodiments, the antibodies provided herein have a light chain variable (VL) region that has (1) a VL CDR1 comprising an amino acid sequence of SEQ ID NO: 46; (2) a VL CDR2 comprising an amino acid sequence of SEQ ID NO: 47; and/or (3) a VL CDR3 comprising an amino acid sequence of SEQ ID NO: 48.

In some embodiments, the antibodies provided herein have a light chain variable (VL) region that has (1) a VL CDR1 comprising an amino acid sequence of SEQ ID NO: 49; (2) a VL CDR2 comprising an amino acid sequence of SEQ ID NO: 50; and/or (3) a VL CDR3 comprising an amino acid sequence of SEQ ID NO: 51.

In some embodiments, the antibodies provided herein have a light chain variable (VL) region that has (1) a VL CDR1 comprising an amino acid sequence of SEQ ID NO: 52; (2) a VL CDR2 comprising g an amino acid sequence of SEQ ID NO: 53; and/or (3) a VL CDR3 comprising an amino acid sequence of SEQ ID NO: 54.

In some embodiments, the antibodies provided herein have a light chain variable (VL) region that has (1) a VL CDR1 comprising an amino acid sequence of SEQ ID NO: 55; (2) a VL CDR2 comprising an amino acid sequence of SEQ ID NO: 56; and/or (3) a VL CDR3 comprising an amino acid sequence of SEQ ID NO: 57.

In some embodiments, the antibodies provided herein have a light chain variable (VL) region that has (1) a VL CDR1 comprising an amino acid sequence of SEQ ID NO: 74; (2) a VL CDR2 comprising an amino acid sequence of SEQ ID NO: 75; and/or (3) a VL CDR3 comprising an amino acid sequence of SEQ ID NO: 76.

In some embodiments, the molecules provided herein have a light chain variable (VL) region that has (1) a VL CDR1 comprising an amino acid sequence of SEQ ID NO: 77; (2) a VL CDR2 comprising an amino acid sequence of SEQ ID NO: 78; and/or (3) a VL CDR3 comprising an amino acid sequence of SEQ ID NO: 79.

In some embodiments, the antibodies provided herein have a light chain variable (VL) region that has (1) a VL CDR1 comprising an amino acid sequence of SEQ ID NO: 80; (2) a VL CDR2 comprising an amino acid sequence of SEQ ID NO: 81; and/or (3) a VL CDR3 comprising an amino acid sequence of SEQ ID NO: 82.

In some embodiments, the antibodies provided herein have a light chain variable (VL) region that has (1) a VL CDR1 comprising an amino acid sequence of SEQ ID NO: 83; (2) a VL CDR2 comprising an amino acid sequence of SEQ ID NO: 84; and/or (3) a VL CDR3 comprising an amino acid sequence of SEQ ID NO: 85.

In some embodiments, the antibodies provided herein have a light chain variable (VL) region that comprises the amino acid sequence of SEQ ID NO: 4. The antibodies can be monoclonal antibodies. The antibodies can be a humanized antibodies.

In some embodiments, the antibodies provided herein have a light chain variable (VL) region that comprises the amino acid sequence of SEQ ID NO: 32. The antibodies can be monoclonal antibodies. The antibodies can be humanized antibodies.

In some embodiments, the antibodies provided herein have a light chain variable (VL) region that comprises the amino acid sequence of SEQ ID NO: 60. The antibodies can be monoclonal antibodies. The antibodies can be a humanized antibodies.

In some embodiments, the antibodies provided herein have (a) a heavy chain variable (VH) region comprising: (1) a VH CDR1 comprising an amino acid sequence of SEQ ID NO 6; (2) a VH CDR2 comprising an amino acid sequence of SEQ ID NO 7; and/or (3) a VH CDR3 comprising an amino acid sequence of SEQ ID NO 8; and (b) a light chain variable (VL) region comprising: (1) a VL CDR1 comprising an amino acid sequence of SEQ ID NO: 18; (2) a VL CDR2 comprising an amino acid sequence of SEQ ID NO: 19; and/or (3) a VL CDR3 comprising an amino acid sequence of SEQ ID NO: 20. The antibodies can be a monoclonal antibodies. The antibodies can be a humanized antibodies.

In some embodiments, the antibodies provided herein have (a) a heavy chain variable (VH) region comprising: (1) a VH CDR1 comprising an amino acid sequence of SEQ ID NO 9; (2) a VH CDR2 comprising an amino acid sequence of SEQ ID NO 10; and/or (3) a VH CDR3 comprising an amino acid sequence of SEQ ID NO 11; and (b) a light chain variable (VL) region comprising: (1) a VL CDR1 comprising an amino acid sequence of SEQ ID NO: 21; (2) a VL CDR2 comprising an amino acid sequence of SEQ ID NO: 22; and/or (3) a VL CDR3 comprising an amino acid sequence of SEQ ID NO: 23. The antibodies can be monoclonal antibodies. The antibodies can be humanized antibodies.

In some embodiments, the antibodies provided herein have (a) a heavy chain variable (VH) region comprising: (1) a VH CDR1 comprising an amino acid sequence of SEQ ID NO 12; (2) a VH CDR2 comprising an amino acid sequence of SEQ ID NO 13; and/or (3) a VH CDR3 comprising an amino acid sequence of SEQ ID NO 14; and (b) a light chain variable (VL) region comprising: (1) a VL CDR1 comprising an amino acid sequence of SEQ ID NO: 24; (2) a VL CDR2 comprising an amino acid sequence of SEQ ID NO: 25; and/or (3) a VL CDR3 comprising an amino acid sequence of SEQ ID NO: 26. The antibodies can be monoclonal antibodies. The antibodies can be humanized antibodies.

In some embodiments, the antibodies provided herein have (a) a heavy chain variable (VH) region comprising: (1) a VH CDR1 comprising an amino acid sequence of SEQ ID NO 15; (2) a VH CDR2 comprising an amino acid sequence of SEQ ID NO 16; and (3) a VH CDR3 comprising an amino acid sequence of SEQ ID NO 17; and (b) a light chain variable (VL) region comprising: (1) a VL CDR1 comprising an amino acid sequence of SEQ ID NO: 27; (2) a VL CDR2 comprising an amino acid sequence of SEQ ID NO: 28; and (3) a VL CDR3 comprising an amino acid sequence of SEQ ID NO: 29. The antibodies can be monoclonal antibodies. The antibodies can be a humanized antibodies.

In some embodiments, the antibodies provided herein have (a) a heavy chain variable (VH) region comprising: (1) a VH CDR1 comprising an amino acid sequence of SEQ ID NO 34; (2) a VH CDR2 comprising an amino acid sequence of SEQ ID NO 35; and (3) a VH CDR3 comprising g an amino acid sequence of SEQ ID NO 36; and (b) a light chain variable (VL) region comprising: (1) a VL CDR1 comprising an amino acid sequence of SEQ ID NO: 46; (2) a VL CDR2 comprising an amino acid sequence of SEQ ID NO: 47; and (3) a VL CDR3 comprising an amino acid sequence of SEQ ID NO: 48. The antibodies can be monoclonal antibodies. The antibodies can be a humanized antibodies.

In some embodiments, the antibodies provided herein have (a) a heavy chain variable (VH) region comprising: (1) a VH CDR1 comprising an amino acid sequence of SEQ ID NO 37; (2) a VH CDR2 comprising an amino acid sequence of SEQ ID NO 38; and (3) a VH CDR3 comprising an amino acid sequence of SEQ ID NO 39; and (b) a light chain variable (VL) region comprising: (1) a VL CDR1 comprising an amino acid sequence of SEQ ID NO: 49; (2) a VL CDR2 comprising an amino acid sequence of SEQ ID NO: 50; and (3) a VL CDR3 comprising an amino acid sequence of SEQ ID NO: 51. The antibodies can be a monoclonal antibodies. The antibodies can be a humanized antibodies.

In some embodiments, the antibodies provided herein have s (a) a heavy chain variable (VH) region comprising: (1) a VH CDR1 comprising an amino acid sequence of SEQ ID NO 40; (2) a VH CDR2 comprising an amino acid sequence of SEQ ID NO 41; and (3) a VH CDR3 comprising an amino acid sequence of SEQ ID NO 42; and (b) a light chain variable (VL) region comprising: (1) a VL CDR1 comprising an amino acid sequence of SEQ ID NO: 52; (2) a VL CDR2 comprising an amino acid sequence of SEQ ID NO: 53; and (3) a VL CDR3 comprising an amino acid sequence of SEQ ID NO: 54. The antibodies can be monoclonal antibodies. The antibodies can be humanized antibodies.

In some embodiments, the molecules provided herein have (a) a heavy chain variable (VH) region comprising: (1) a VH CDR1 comprising an amino acid sequence of SEQ ID NO 43; (2) a VH CDR2 comprising an amino acid sequence of SEQ ID NO 44; and (3) a VH CDR3 comprising an amino acid sequence of SEQ ID NO 45; and (b) a light chain variable (VL) region comprising: (1) a VL CDR1 comprising an amino acid sequence of SEQ ID NO: 55; (2) a VL CDR2 comprising an amino acid sequence of SEQ ID NO: 56; and (3) a VL CDR3 comprising an amino acid sequence of SEQ ID NO: 57. The antibodies can be monoclonal antibodies. The antibodies can be humanized antibodies.

In some embodiments, the molecules provided herein have (a) a heavy chain variable (VH) region comprising: (1) a VH CDR1 comprising an amino acid sequence of SEQ ID NO 62; (2) a VH CDR2 comprising an amino acid sequence of SEQ ID NO 63; and (3) a VH CDR3 comprising an amino acid sequence of SEQ ID NO 64; and (b) a light chain variable (VL) region comprising: (1) a VL CDR1 comprising an amino acid sequence of SEQ ID NO: 74; (2) a VL CDR2 comprising an amino acid sequence of SEQ ID NO: 75; and (3) a VL CDR3 comprising an amino acid sequence of SEQ ID NO: 76. The antibodies can be monoclonal antibodies. The antibodies can be humanized antibodies.

In some embodiments, the antibodies provided herein have (a) a heavy chain variable (VH) region comprising: (1) a VH CDR1 comprising an amino acid sequence of SEQ ID NO 65; (2) a VH CDR2 comprising an amino acid sequence of SEQ ID NO 66; and (3) a VH CDR3 comprising an amino acid sequence of SEQ ID NO 67; and (b) a light chain variable (VL) region comprising: (1) a VL CDR1 comprising an amino acid sequence of SEQ ID NO: 77; (2) a VL CDR2 comprising an amino acid sequence of SEQ ID NO:

78; and (3) a VL CDR3 comprising an amino acid sequence of SEQ ID NO: 79. The antibodies can be monoclonal antibodies. The antibodies can be humanized antibodies.

In some embodiments, the antibodies provided herein have (a) a heavy chain variable (VH) region comprising: (1) a VH CDR1 comprising an amino acid sequence of SEQ ID NO 68; (2) a VH CDR2 comprising an amino acid sequence of SEQ ID NO 69; and (3) a VH CDR3 comprising an amino acid sequence of SEQ ID NO 70; and (b) a light chain variable (VL) region comprising: (1) a VL CDR1 comprising an amino acid sequence of SEQ ID NO: 80; (2) a VL CDR2 comprising an amino acid sequence of SEQ ID NO: 81; and (3) a VL CDR3 comprising an amino acid sequence of SEQ ID NO: 82. The antibodies can be monoclonal antibodies. The antibodies can be humanized antibodies.

In some embodiments, the antibodies provided herein have (a) a heavy chain variable (VH) region comprising: (1) a VH CDR1 comprising an amino acid sequence of SEQ ID NO 71; (2) a VH CDR2 comprising an amino acid sequence of SEQ ID NO 72; and (3) a VH CDR3 comprising an amino acid sequence of SEQ ID NO 73; and (b) a light chain variable (VL) region comprising: (1) a VL CDR1 comprising an amino acid sequence of SEQ ID NO: 83; (2) a VL CDR2 comprising an amino acid sequence of SEQ ID NO: 84; and (3) a VL CDR3 comprising an amino acid sequence of SEQ ID NO: 85. The antibodies can be monoclonal antibodies. The antibodies can be humanized antibodies.

In some embodiments, the antibodies provided herein have a VH region that comprises the amino acid sequence of SEQ ID NO: 2 and the VL region that has the the amino acid sequence of SEQ ID NO: 4. The antibodies can be monoclonal antibodies. The antibodies can be humanized antibodies.

In some embodiments, the antibodies provided herein have a VH region that has the amino acid sequence of SEQ ID NO: 30 and the VL region that has the the amino acid sequence of SEQ ID NO: 32. The molecule can be an antibody. The antibodies can be monoclonal antibodies. The antibodies can be humanized antibodies.

In some embodiments, the antibodies provided herein have a VH region that has the amino acid sequence of SEQ ID NO: 58 and the VL region that has the the amino acid sequence of SEQ ID NO: 60. The antibody can be a monoclonal antibody. The antibodies can be monoclonal antibodies. The antibodies can be humanized antibodies.

In some embodiments, the antibodies provided herein is the mouse monoclonal antibody designated as STC613, or a humanized antibody version thereof. A humanized STC613 antibody can comprise the VH region, the VL region, or both the VH and VL region of STC613 as described herein. A humanized STC613 antibody can also comprise six CDR regions (VH CDR1, VH CDR2, VH CDR3, VL CDR1, VL CDR2 and VL CDR3) of STC613 as described herein. The humanized STC613 antibody can also comprise less than the six CDR regions of STC613. In some embodiments, the humanized STC613 antibody can also comprise one, two, three, four, or five CDR regions (VH CDR1, VH CDR2, VH CDR3, VL CDR1, VL CDR2 and VL CDR3) of STC613.

In some embodiments, the antibody provided herein is the mouse monoclonal antibody designated as STC626, or a humanized antibody version thereof. A humanized STC626 antibody can comprise the VH region, the VL region, or both the VH and VL region of STC626 as described herein. A humanized STC626 antibody can also comprise six CDR regions (VH CDR1, VH CDR2, VH CDR3, VL CDR1, VL CDR2 and VL CDR3) of STC626 as described herein. The humanized STC626 antibody can also comprise less than the six CDR regions of STC626. In some embodiments, the humanized STC626 antibody can also comprise one, two, three, four, or five CDR regions (VH CDR1, VH CDR2, VH CDR3, VL CDR1, VL CDR2 and VL CDR3) of STC626.

In some embodiments, the antibody provided herein is the mouse monoclonal antibody designated as STC635, or a humanized antibody version thereof. A humanized STC635 antibody can comprise the VH region, the VL region, or both the VH and VL region of STC635 as described herein. A humanized STC635 antibody can also comprise six CDR regions (VH CDR1, VH CDR2, VH CDR3, VL CDR1, VL CDR2 and VL CDR3) of STC635 as described herein. The humanized STC635 antibody can also comprise less than the six CDR regions of STC635. In some embodiments, the humanized STC635 antibody can also comprise one, two, three, four, or five CDR regions (VH CDR1, VH CDR2, VH CDR3, VL CDR1, VL CDR2 and VL CDR3) of STC635.

In some embodiments, the anti-BTLA antibodies provided herein are IgG, IgM, IgA, IgD, or IgE. In some embodiments, the anti-BTLA antibodies provided herein are IgG1, IgG2A, IgG2B, IgG3 or IgGM.

Standard techniques known to those of skill in the art can be used to introduce mutations in the nucleotide sequence encoding an antigen binding fragment, or an antibody, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In some embodiments, the anti-BTLA antibodies provided herein specifically bind to BTLA and can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the murine monoclonal antibodies STC613, STC626, or STC635, or an antigen-binding fragment thereof, such as a VH domain or VL domain. In some embodiments, the anti-BTLA antibodies provided herein can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS: 2, 4, 30, 32, 58, or 60. In some embodiments, the anti-BTLA antibodies provided herein can have a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence and/or a VL CDR amino acid sequence depicted in Table 3, 5, or 7 above.

In some embodiments, the anti-BTLA antibodies provided herein can have an amino acid sequence of a VH domain and/or an amino acid sequence a VL domain encoded by a nucleotide sequence that hybridizes to the complement of a nucleotide sequence encoding any one of the VH and/or VL domains depicted in Table 2, 4, or 6 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

In some embodiments, the anti-BTLA antibodies provided herein can have an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Table 2, 4, or 6 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

In some embodiments, provided herein are also isolated nucleic acid that encode an amino acid sequence of a VH CDR or an amino acid sequence of a VL CDR depicted in Table 2, 4, or 6, or that hybridizes to the complement of a nucleic acid sequence encoding any one of the VH CDRs and/or VL CDRs depicted in Table 2, 4, or 6 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, provided herein are also isolated nucleic acid that encode an amino acid sequence of a VH domain and/or an amino acid sequence a VL domain depicted in Table 2, 4, or 6, or that hybridizes to the complement of a nucleotide sequence encoding any one of the VH and/or VL domains depicted in Table 2, 4, or 6 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 3, 31, or 59 or that hybridizes to the complement of a nucleotide sequence of SEQ ID NO: 3, 31, or 59 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 5, 33, or 61 or that hybridizes to the complement of a nucleotide sequence of SEQ ID NO: 5, 33, or 61 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the anti-glycosylated BTLA antibodies provided herein can be chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody can contain one or more non-classical amino acids.

The anti-glycosylated BTLA antibodies provided herein can have a framework region known to those of skill in the art (e.g., a human or non-human fragment). The framework region can, for example, be naturally occurring or consensus framework regions. In specific embodiments, the framework region of an antibody provided herein is human (see, e.g., Chothia et al., 1998, *J Mol. Biol.* 278:457-479 for a listing of human framework regions, which is incorporated by reference herein in its entirety). See also Kabat et al. (1991) Sequences of Proteins of Immunological Interest (U.S. Department of Health and Human Services, Washington, D.C.) 5th ed.

The BTLA epitopes of STC613 were mapped by cross-link analysis. See Example 7. Table 8 summarizes the cross-linked peptides of BTLA and STC613, which represent BTLA epitopes of STC613 (SEQ ID NOS: 161, 162, 163, 164, 165, 166). FIG. 7 shows a synthesized epitope of BTLA antigen (SEQ ID NO: 86) for STC613: IKRQSEHSILA (SEQ ID NO: 167)—VKLEDRQTSWK (SEQ ID NO: 168)-NGSYRCSANFQ (SEQ ID NO: 169)

IKRQSEHSILA (SEQ ID NO: 167)

VKLEDRQTSWK (SEQ ID NO: 168)

NGSYRCSANFQ (SEQ ID NO: 169)

TABLE 8

Cross-linked peptides of BTLA (SEQ ID NO: 86) with STC613 analyzed by nLC-orbitrap MS/MS.

| Sequence | Protein 1 | Protein 2 | Sequence protein 1 | Sequence protein 2 |
|---|---|---|---|---|
| Chymotrypsin Proteolysis | | | | |
| SCAASGFTF (SEQ ID NO: 156)-YIKRQSEHSIL (SEQ ID NO: 161)-a8-b8 | STC613_HC | BTLA | 21-29 | 9-19 |
| SVTIGQPASISCKSSLSL (SEQ ID NO: 157)-EDRQTSW (SEQ ID NO: 162)-a13-b5 | STC613_LC | BTLA | 12-29 | 53-59 |
| SVTIGQPASISCKSSLSL (SEQ ID NO: 157)-RCSANFQSNL-a13 (SEQ ID NO: 163)-b3 | STC613_LC | BTLA | 12-29 | 84-93 |
| TLKISRVEAEDVGVYY (SEQ ID NO: 158)-NGTTCVKL (SEQ ID NO: 164)-a15-b7 | STC613_LC | BTLA | 77-92 | 45-52 |
| KISRVEAEDVGVYY (SEQ ID NO: 159)-EPVLPNDNGSY (SEQ ID NO: 165)-a13-b10 | STC613_LC | BTLA | 79-92 | 73-83 |
| Thermolysin Proteolysis | | | | |
| ISCKSSLSL (SEQ ID NO: 160)-LYIKRQSEHSI (SEQ ID NO: 166)-a5-b5 | STC613_LC | BTLA | 103-108 | 8-18 |

* Peptide sequence positions are indicated relative to the STC613 amino acid sequences of SEQ ID NOS: 2 and 4 (Protein 1), and the BTLA amino acid sequence of SEQ ID NO: 86 (Protein 2).

Accordingly, provided herein are also anti-glycosylated BTLA antibodies that competitively block (e.g., in a dose-dependent manner) a BTLA epitope described herein. In some embodiments, provided herein are anti-glycosylated BTLA antibodies that competitively block (e.g., in a dose-dependent manner) a BTLA epitope of STC613 as described herein. In some embodiments, the anti-glycosylated BTLA antibodies provided herein specifically bind to an epitope of BTLA as described herein. In some embodiments, the anti-glycosylated BTLA antibodies provided herein specifically bind to a BTLA epitope of STC613.

In some embodiments, the anti-glycosylated BTLA antibodies provided herein competitively block (e.g., in a dose-dependent manner) a BTLA epitope, wherein the BTLA epitope has at least five consecutive amino acids of an amino acid sequence of SEQ ID NOS: 161, 162, 163, 164, 165, 166, 167, 168, or 169. The epitope of BTLA can have at least six, at least seven, at least eight, at least nine, at least ten, at least eleven, at least twelve, at least thirteen, at least fourteen, or at least fifteen, consecutive amino acids of an amino acid sequence of SEQ ID NOS: 161, 162, 163, 164, 165, 166, 167, 168, or 169. The epitope of BTLA can have at least six consecutive amino acids of an amino acid sequence of SEQ ID NOS: 161, 162, 163, 164, 165, 166, 167, 168, or 169. The epitope of BTLA can have at least seven consecutive amino acids of an amino acid sequence of SEQ ID NOS: 161, 162, 163, 164, 165, 166, 167, 168, or 169. The epitope of BTLA can have at least eight consecutive amino acids of an amino acid sequence of SEQ ID NOS: 161, 162, 163, 164, 165, 166, 167, 168, or 169. The epitope of BTLA can have at least nine consecutive amino acids of an amino acid sequence of SEQ ID NOS: 161, 162, 163, 164, 165, 166, 167, 168, or 169. The epitope of BTLA can have at least ten consecutive amino acids of an amino acid sequence of SEQ ID NOS: 161, 162, 163, 164, 165, 166, 167, 168, or 169. The epitope of BTLA can have at least eleven consecutive amino acids of an amino acid sequence of SEQ ID NOS: 161, 162, 163, 164, 165, 166, 167, 168, or 169. The epitope of BTLA can have at least twelve consecutive amino acids of an amino acid sequence of SEQ ID NOS: 161, 162, 163, 164, 165, 166, 167, 168, or 169. The epitope of BTLA can have at least thirteen consecutive amino acids of an amino acid sequence of SEQ ID NOS: 161, 162, 163, 164, 165, 166, 167, 168, or 169. The epitope of BTLA can have at least fourteen consecutive amino acids of an amino acid sequence of SEQ ID NOS: 161, 162, 163, 164, 165, 166, 167, 168, or 169. The epitope of BTLA can have at least fifteen consecutive amino acids of an amino acid sequence of SEQ ID NOS:

161, 162, 163, 164, 165, 166, 167, 168, or 169. The anti-glycosylated BTLA antibodies can be humanized antibodies.

In some embodiments, the anti-glycosylated BTLA antibodies competitively block (e.g., in a dose-dependent manner) a BTLA epitope, wherein the BTLA epitope has an amino acid sequence of SEQ ID NOS: 161, 162, 163, 164, 165, 166, 167, 168, or 169. In some embodiments, the anti-BTLA antibodies provided herein have an antigen binding fragment that specifically binds to an epitope of BTLA, wherein the BTLA epitope has an amino acid sequence of SEQ ID NOS: 161, 162, 163, 164, 165, 166, 167, 168, or 169. The epitope of BTLA can have an amino acid sequence of SEQ ID NO: 161. The epitope of BTLA can have an amino acid sequence of SEQ ID NO: 162. The epitope of BTLA can have an amino acid sequence of SEQ ID NO: 163. The epitope of BTLA can have an amino acid sequence of SEQ ID NO: 164. The epitope of BTLA can have an amino acid sequence of SEQ ID NO: 165. The epitope of BTLA can have an amino acid sequence of SEQ ID NO: 166. The epitope of BTLA can have an amino acid sequence of SEQ ID NO: 167. The epitope of BTLA can have an amino acid sequence of SEQ ID NO: 168. The epitope of BTLA can have an amino acid sequence of SEQ ID NO: 169.

In some embodiments, the anti-glycosylated BTLA antibodies provided herein competitively block (e.g., in a dose-dependent manner) a BTLA epitope, wherein the BTLA epitope has at one or more amino acids of R12, H16, K51, T57, S82, or S86 of BTLA (SEQ ID NO: 86). The epitope of BTLA can have one, two, three, four, or five amino acids of R12, H16, K51, T57, S82, or S86 of BTLA (SEQ ID NO: 86). The epitope of BTLA can have one amino acid of R12, H16, K51, T57, S82, or S86 of BTLA (SEQ ID NO: 86). The epitope of BTLA can have two amino acids of R12, H16, K51, T57, S82, or S86 of BTLA (SEQ ID NO: 86). The epitope of BTLA can have three amino acids of R12, H16, K51, T57, S82, or S86 of BTLA (SEQ ID NO: 86). The epitope of BTLA can have four amino acids of R12, H16, K51, T57, S82, or S86 of BTLA (SEQ ID NO: 86). The epitope of BTLA can have five amino acid of R12, H16, K51, T57, S82, or S86 of BTLA (SEQ ID NO: 86). The anti-glycosylated BTLA antibodies can be humanized antibodies.

In some embodiments, the anti-glycosylated BTLA antibodies provided herein competitively block (e.g., in a dose-dependent manner) a BTLA epitope, wherein the BTLA epitope has at one or more amino acids of R12, H16, K51, T57, S82, or S86 of BTLA (SEQ ID NO: 86). The epitope of BTLA can have R12 of BTLA (SEQ ID NO: 86). The epitope of BTLA can have H16 of BTLA (SEQ ID NO: 86). The epitope of BTLA can have K51 of BTLA (SEQ ID NO: 86). The epitope of BTLA can have T57 of BTLA (SEQ ID NO: 86). The epitope of BTLA can have S82 of BTLA (SEQ ID NO: 86). The epitope of BTLA can have S86 of BTLA (SEQ ID NO: 86). The anti-glycosylated BTLA antibodies can be humanized antibodies.

In some embodiments, the anti-glycosylated BTLA antibodies provided herein have a high affinity for glycosylated BTLA or a polypeptide, or polypeptide fragment or epitope thereof. In one embodiment, the molecules provided herein can be anti-BTLA antibodies that have a higher affinity for BTLA than known antibodies (e.g., commercially available monoclonal antibodies discussed elsewhere herein). In some embodiments, the anti-BTLA antibodies provided herein can have a 2- to 10-fold (or more) higher affinity for a BTLA antigen than a known anti-BTLA antibody as assessed by techniques described herein or known to one of skill in the art (e.g., a BIAcore assay). In accordance with these embodiments, the affinity of the antibodies are, in one embodiment, assessed by a BIAcore assay.

In some embodiments, the anti-glycosylated BTLA antibodies provided herein can bind specifically to glycosylated BTLA or a glycosylated polypeptide fragment or epitope thereof with a dissociation constant ($K_D$) of no more than 1 µM, no more than 100 nM, no more than 10 nM, no more than 1 nM, or no more than 0.1 nM. In some embodiments, the anti-glycosylated BTLA antibodies provided herein have a $K_D$ of no more than 500 nM. In some embodiments, the anti-glycosylated BTLA antibodies provided herein have a $K_D$ of no more than 200 nM. In some embodiments, the anti-glycosylated BTLA antibodies provided herein have a $K_D$ of no more than 100 nM. In some embodiments, the anti-glycosylated BTLA antibodies provided herein have a $K_D$ of no more than 50 nM. In some embodiments, the anti-glycosylated BTLA antibodies provided herein have a $K_D$ of no more than 20 nM. In some embodiments, the anti-glycosylated BTLA antibodies provided herein have a $K_D$ of no more than 10 nM. In some embodiments, the anti-glycosylated BTLA antibodies provided herein have a $K_D$ of no more than 5 nM. In some embodiments, the anti-glycosylated BTLA antibodies provided herein have a $K_D$ of no more than 2 nM. In some embodiments, the anti-glycosylated BTLA provided herein have a $K_D$ of no more than 1 nM. In some embodiments, the anti-glycosylated BTLA provided herein have a $K_D$ of no more than 0.5 nM. In some embodiments, the anti-glycosylated BTLA antibodies provided herein have a $K_D$ of no more than 0.1 nM.

In some embodiments, the anti-glycosylated BTLA antibodies provided herein can block or neutralize the activities of BTLA. The anti-glycosylated BTLA antibodies can be neutralizing antibodies. The neutralizing antibodies can block the binding of BTLA with a natural ligand, such as HVEM, and inhibit the signaling pathways mediated by BTLA and/or its other physiological activities. The IC50 of neutralizing antibodies can range between 0.01-10 µg/ml in a neutralization assay (e.g., an ELISA). The IC50 of a neutralizing antibodies can be no more than 10 µg/ml. The IC50 of a neutralizing antibodies can be no more than 8 µg/ml. The IC50 of a neutralizing antibodies can be no more than 6 µg/ml. The IC50 of a neutralizing antibody can be no more than 4 µg/ml. The IC50 of a neutralizing antibody can be no more than 2 µg/ml. The IC50 of a neutralizing antibody can be no more than 1 µg/ml. The IC50 of a neutralizing antibody can be no more than 0.8 µg/ml. The IC50 of a neutralizing antibody can be no more than 0.6 µg/ml. The IC50 of a neutralizing antibody can be no more than 0.4 µg/ml. The IC50 of a neutralizing antibody can be no more than 0.2 µg/ml. The IC50 of a neutralizing antibody can be no more than 0.1 µg/ml. The IC50 of a neutralizing antibody can be no more than 0.08 µg/ml. The IC50 of a neutralizing antibody can be no more than 0.06 µg/ml. The IC50 of a neutralizing antibody can be no more than 0.04 µg/ml. The IC50 of a neutralizing antibody can be no more than 0.02 µg/ml. The IC50 of a neutralizing antibody can be no more than 0.01 µg/ml.

In some embodiments, the anti-glycosylated BTLA antibodies provided herein bind specifically to glycosylated BTLA. In some embodiments, the anti-glycosylated BTLA antibodies specifically bind to BTLA glycosylated at positions N75, N94, N110 or any combination thereof. In some embodiments, the anti-glycosylated BTLA antibodies specifically bind to BTLA glycosylated at position N75. In some embodiments, the anti-glycosylated BTLA antibodies specifically bind to BTLA glycosylated at position N94. In some embodiments, the anti-glycosylated BTLA antibodies specifically bind to BTLA glycosylated at position N110. In some embodiments, the anti-glycosylated BTLA antibodies specifically bind to BTLA glycosylated at positions N75 and N94. In some embodiments, the anti-glycosylated BTLA antibodies specifically bind to BTLA glycosylated at positions N75 and N110. In some embodiments, the anti-glycosylated BTLA antibodies specifically bind to BTLA glycosylated at positions N94 and N110. In some embodiments, the anti-glycosylated BTLA antibodies specifically bind to BTLA glycosylated at positions N75, N94 and N110.

The anti-glycosylated BTLA antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody.

In particular, anti-glycosylated BTLA antibodies provided herein include immunoglobulin molecules and immunologically active portions of immunoglobulin molecules, e.g., molecules that contain an antigen binding fragment that specifically bind to BTLA or glycosylated BTLA. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

The anti-glycosylated BTLA antibodies provided herein can be monospecific, bispecific, trispecific antibodies or antibodies of greater multispecificity. Multispecific antibodies may be specific for different epitopes of a BTLA as described here, or can be specific for both a BTLA polypeptide as well as for a heterologous epitope, such as a heterologous polypeptide or solid support material. In specific embodiments, the antibodies provided herein are monospecific for a given epitope of a BTLA polypeptide and do not bind to other epitopes.

By known means and as described herein, polyclonal or monoclonal antibodies, antigen binding fragments, and binding domains and CDRs (including engineered forms of any of the foregoing) can be created that are specific to glycosylated BTLA, one or more of its respective epitopes, or conjugates of any of the foregoing, whether such antigens or epitopes are isolated from natural sources or are synthetic derivatives or variants of the natural compounds.

Antibodies can be produced from any animal source, including birds and mammals. In some embodiments, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is hereby incorporated by reference in its entirety. These techniques are further described in Marks et al., *Bio/Technol.*, 10:779-783(1992); Stemmer, *Nature*, 370:389-391(1994); Gram et al., *Proc. Natl. Acad. Sci. USA*, 89:3576-3580 (1992); Barbas et al., *Proc. Natl. Acad. Sci. USA*, 91:3809-3813(1994); and Schier et al., *Gene*, 169(2): 147-155(1996); which are hereby incorporated by reference in their entireties.

Methods for producing polyclonal antibodies in various animal species, as well as for producing monoclonal antibodies of various types, including humanized, chimeric, and fully human, are well known in the art. For example, the following U.S. patents provide enabling descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098, which are hereby incorporated by reference in their entireties.

In some embodiments, the anti-glycosylated BTLA antibodies can be monoclonal antibodies. In some embodiments, the anti-glycosylated BTLA can be polyclonal antibodies. Animals can be inoculated with an antigen, such as a glycosylated BTLA polypeptide in order to produce antibodies specific for a glycosylated BTLA polypeptide. Frequently an antigen is bound or conjugated to another molecule to enhance the immune response. A conjugate can be any peptide, polypeptide, protein, or non-proteinaceous substance bound to an antigen that is used to elicit an immune response in an animal. Antibodies produced in an animal in response to antigen inoculation have a variety of non-identical molecules (polyclonal antibodies) made from a variety of individual antibody producing B lymphocytes. Given the correct conditions for polyclonal antibody production in an animal, most of the antibodies in the animal's serum recognize the collective epitopes on the antigenic compound to which the animal has been immunized.

This specificity can be further enhanced by affinity purification to select only those antibodies that recognize the antigen or epitope of interest. The methods for generating monoclonal antibodies (MAbs) can begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and can provide certain advantages. Mice (e.g., BALB/c mice) are routinely used and generally give a high percentage of stable fusions.

Hybridoma technology involves the fusion of a single B lymphocyte from a mouse previously immunized with a glycosylated BTLA polypeptide with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) can be produced.

The anti-glycosylated BTLA antibodies can be produced by any method known in the art useful for the production of polypeptides, e.g., in vitro synthesis, recombinant DNA production, and the like. The humanized antibodies can be produced by recombinant DNA technology. The antibodies described herein can also be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; which are hereby incorporated by reference in their entireties. Techniques for the recombinant expression of immunoglobulins, including humanized immunoglobulins, can also be found, in Goeddel et al., *Gene Expression Technology Methods in Enzymology* Vol. 185 Academic Press (1991), and Borreback, *Antibody Engineering*, W. H. Freeman (1992); which are hereby incorporated by reference in their entireties. Additional information concerning the generation, design and expression of recombinant antibodies can be found in Mayforth, *Designing Antibodies*, Academic Press, San Diego (1993).

Methods have been developed to replace light and heavy chain constant domains of the monoclonal antibody with analogous domains of human origin, leaving the variable regions of the foreign antibody intact. Alternatively, fully human monoclonal antibodies are produced in mice or rats transgenic for human immunoglobulin genes. Methods have also been developed to convert variable domains of monoclonal antibodies to more human form by recombinantly constructing antibody variable domains having both rodent and human amino acid sequences. In humanized monoclonal antibodies, only the hypervariable CDR is derived from non-human (e.g., mouse, rat, chicken, llama) monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody can also be subject to genetic mutation or other changes, which may or may not alter the binding specificity of antibodies produced by the hybridoma.

Engineered antibodies can be created, by using monoclonal and other antibodies and recombinant DNA technology to produce other antibodies or chimeric molecules that retain the antigen or epitope specificity of the original antibody, i.e., the molecule has binding domain. Such techniques can involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513 and 6,881,557, which are incorporated herein by reference.

In certain embodiments, the anti-glycosylated BTLA antibody is a human antibody. Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a glycosylated BTLA polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, therapeutically useful IgG, IgA, IgM and IgE antibodies can be produced. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening of a human phage library, etc.). In one embodiment, a chimeric antibody provided herein has murine V regions and human C regions. In one embodiment, the murine light chain V region is fused to a human kappa light chain. In one embodiment, the murine heavy chain V region is fused to a human IgG1 C region.

Methods for producing chimeric antibodies are known in the art. See e.g., Morrison, *Science* 229:1202 (1985); Oi et al., *BioTechniques* 4:214 (1986); Gillies et al., *J. Immunol. Methods* 125:191-202(1989); and U.S. Pat. Nos. 6,311,415, 5,807,715, 4,816,567, and 4,816,397; all of which are hereby incorporated by references in their entireties. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, *Molecular Immunology* 28(4/5):489-498 (1991); Studnicka et al., *Protein Engineering* 7:805 (1994); and Roguska et al., *Proc. Natl. Acad. Sci. USA* 91:969 (1994)), and chain shuffling (U.S. Pat. No. 5,565,332); all of which are hereby incorporated by references in their entireties.

An exemplary process for the production of the recombinant chimeric anti-glycosylated BTLA antibodies can include the following: a) constructing, by conventional molecular biology methods, an expression vector that encodes and expresses an antibody heavy chain in which the CDRs and variable region of the murine anti-glycosylated BTLA monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-glycosylated BTLA monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized anti-glycosylated BTLA antibodies can include the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-glycosylated BTLA monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-glycosylated BTLA monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains can comprise cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands). Furthermore, codon usage can by optimized when host cell is selected to account for species specific codon usage bias and enhance protein expression. For example, for CHO cell expression the DNA encoding the antibodies can incorporate codons used preferentially by *Cricetulus griseus* (from where Chinese Hamster ovaries cells are derived. Methods of codon optimization may be employed to facilitate improved expression by a desired host cell (see e.g., Wohlgemuth et al., *Philos. Trans. R. Soc. Lond. B Biol. Sci.* 366(1580): 2979-2986 (2011); Jestin et al., *J. Mol. Evol.* 69(5):452-457 (2009); Bollenbach et al., *Genome Res.* 17(4):401-404 (2007); Kurland et al., *Prog. Nucleic Acid Res. Mol. Biol.* 31:191-219 (1984); Grosjean et al., *Gene* 18(3): 199-209 (1982)).

In one embodiment, the antibody is an immunoglobulin single variable domain derived from a camelid antibody, preferably from a heavy chain camelid antibody, devoid of light chains, which are known as $V_HH$ domain sequences or Nanobodies™. A Nanobody™ (Nb) is the smallest functional fragment or single variable domain ($V_HH$) of a naturally occurring single-chain antibody and is known to the person skilled in the art. They are derived from heavy chain only antibodies seen in camelids (Hamers-Casterman et al., *Nature* 363: 446-448 (1993); Desmyter et al., *Nat. Struct. Biol.*, 803-811 (1996)). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a $V_HH$ antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanzied. Nbs are stable, survive the gastro-intestinal system and can easily be manufactured.

Unifying two antigen binding sites of different specificity into a single construct, bispecific antibodies have the ability to bring together two discreet antigens with exquisite specificity and therefore have great potential as therapeutic agents. Bispecific antibodies can be originally made by fusing two hybridomas, each capable of producing a different immunoglobulin. Bispecific antibodies can also be produced by joining two scFv antibody fragments while omitting the Fc portion present in full immunoglobulins. Each scFv unit in such constructs can be made up of one variable domain from each of the heavy (VH) and light (VL) antibody chains, joined with one another via a synthetic polypeptide linker, the latter often being genetically engineered so as to be minimally immunogenic while remaining maximally resistant to proteolysis. Respective scFv units can be joined by a number of techniques including incorporation of a short (usually less than 10 amino acids) polypeptide spacer bridging the two scFv units, thereby creating a bispecific single chain antibody. The resulting bispecific single chain antibody is therefore a species containing two VH/VL pairs of different specificity on a single polypeptide chain, wherein the VH and VL domains in a respective scFv unit are separated by a polypeptide linker long enough to allow intramolecular association between these two domains, and wherein the thusly formed scFv units are contiguously tethered to one another through a polypeptide spacer kept short enough to prevent unwanted association between, for example, the VH domain of one scFv unit and the VL of the other scFv unit.

Examples of antigen binding fragments include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (U.S. Pat. No. 5,091,513); and (ix) diabodies, multivalent, or multispecific fragments constructed by gene fusion (U.S. Patent Appln. Publn. No. 20050214860). Fv, scFv, or diabody molecules may be stabilized by the incorporation of disulfide bridges linking the VH and VL domains. Minibodies having a scFv joined to a CH3 domain can also be made (Hu et al., *Cancer Res.*, 56:3055-3061 (1996)).

Antibody-like binding peptidomimetics are also contemplated in embodiments. Liu et al., *Cell Mol. Biol.*, 49:209-216(2003) describe "antibody like binding peptidomimetics" (ABiPs), which are peptides that act as pared-down antibodies and have certain advantages of longer serum half-life as well as less cumbersome synthesis methods.

7.2.2. Glycosylated BTLA Polypeptides

In yet a further embodiment, a composition is provided comprising a polypeptide comprising a fragment of at least 7 (e.g., at least 8, 9, 10, 11, 12, 13, 14, 15, 16, 17, 18, 19, 20 or more) contiguous amino acids of human BTLA comprising at least one amino acid corresponding to position N75, N94, or N110 of human BTLA, wherein at least one of said amino acids corresponding to position N75, N94, or N110 of human BTLA is glycosylated, wherein the polypeptide is formulated in a pharmaceutically acceptable carrier.

In some embodiments, provided herein are also polypeptides of at least 7 contiguous amino acids of human BTLA having at least one amino acid corresponding to position N75, N94, or N110 of human BTLA, wherein at least one of said amino acids corresponding to position N75, N94, or N110 of human BTLA is glycosylated. In some embodiments, the polypeptide has at least 7 contiguous amino acids of human BTLA having an amino acid corresponding to position N75 which is glycosylated. In some embodiments, the polypeptide has at least 7 contiguous amino acids of human BTLA having an amino acid corresponding to position N94 which is glycosylated. In some embodiments, the polypeptide has at least 7 contiguous amino acids of human BTLA having an amino acid corresponding to position N110 which is glycosylated.

For example, the polypeptide can be a fragment of amino acids 70-76 of human BTLA, wherein N75 is glycosylated. For another example, the polypeptide can be a fragment of amino acids 90-100 of human BTLA, wherein N94 is glycosylated. For yet another example, the polypeptide can be a fragment of amino acid 90-115 of human BTLA, wherein N94 and N110 are glycosylated. A person of ordinary skill in the art would understand polypeptides as contemplated here include any and all polypeptide that have at least 7 contiguous amino acids of human BTLA including at least one amino acid corresponding to position N75, N94, or N110 of human BTLA, wherein at least one of said amino acids corresponding to position N75, N94, or N110 of human BTLA is glycosylated.

In some embodiments, the polypeptide has at least 8, 9, 10, 11, 12, 13, 14, 15, 16, 17, 18, 19 or 20 contiguous amino acids of human BTLA. In some embodiments, the polypeptide has at least 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, or 270, 280 contiguous amino acids of human BTLA. In some embodiments, provided herein is a composition having at least two polypeptides provided herein. The at least two polypeptides can be separate molecule or linked as one molecule. In some embodiments, the composition has at least three polypeptides, at least four polypeptides, or at least five polypeptides. In some embodiments, the composition has two polypeptides, three polypeptides, four polypeptides, or five polypeptides.

In some embodiments, the polypeptides provided herein include unnatural amino acids. In some embodiments, the unnatural amino acids are methylated at the α-amino-group to produce peptides with methylated backbones. In some embodiments, the unnatural amino acids are R-amino acids. In some embodiments, the unnatural amino acid can include a dye (e.g., a fluorescent dye) or an affinity tag. In some embodiments, the polypeptides provided herein includes chemical modification. Chemical modifications include, for example, chemical modifications with biotin, fluorescent dyes. A skilled artisan will recognize that methods for introducing unnatural amino acids into a polypeptide and for chemically modifying a polypeptide are well known in the art.

In some embodiments, a polypeptide of the embodiments is fused or conjugated to an immunogenic polypeptide (e.g., keyhole limpet hemocyanin, KLH). In certain aspects, the polypeptide further comprises a Cys residue at the C- or N-terminus. For example, in some aspects, the polypeptide is conjugated to an immunogenic polypeptide by a disulfide linkage at the Cys residue.

In yet a further embodiment, an immunogenic composition is provided herein having a polypeptide comprising a fragment of at least 7 contiguous amino acids of human BTLA comprising at least one amino acid corresponding to position N75, N94, or N110 of human BTLA, wherein at least one of said amino acids corresponding to position N75, N94, or N110 of human BTLA is glycosylated, wherein the polypeptide is formulated in a pharmaceutically acceptable carrier. In some embodiments, the In some aspects, the immunogenic composition further comprises an adjuvant, such as alum or Freund's adjuvant.

In some embodiments, a method of making an antibody is provided, which includes administering a polypeptide to an animal and isolating the antibody from the animal, wherein the polypeptide has a fragment of at least 7 contiguous amino acids of human BTLA having at least one amino acid corresponding to position N75, N94, or N110 of human BTLA, and wherein at least one of said amino acids corresponding to position N75, N94, or N110 of human BTLA is glycosylated. The animal can be a mouse, rat, rabbit or human. In certain aspects a method further includes identifying the CDRs of the antibody and humanizing the sequences surrounding the CDRs to produce a humanized antibody. In still further aspects, the method comprises recombinantly expressing the humanized antibody. Thus, in a further embodiment, there is provided an isolated antibody produced by the foregoing method. Thus, in some embodiments, provided herein is an isolated antibody that selectively binds to a polypeptide of the embodiments (e.g., a polypeptide comprising a fragment of at least 7 contiguous amino acids of human BTLA comprising at least one amino acid corresponding to position N75, N94, or N110 of human BTLA, wherein at least one of said amino acids corresponding to position N75, N94, or N110 of human BTLA is glycosylated) relative to unglycosylated BTLA.

The polypeptides provided herein can be prepared by any methods known in the art. For example, the polypeptides can be prepared by chemical synthesis or recombinant production. Exemplary methods for expressing and purifying a recombinant polypeptide can be found, for example, in Scopes R. K., *Protein Purification—Principles and Practice, Springer Advanced Texts in Chemistry*, 3$^{rd}$ Edition (1994); Simpson R. J. et al., *Basic Methods in Protein Purification and Analysis: A Laboratory Manual*, Cold Spring Harbor Laboratory Press, 1$^{st}$ Edition (2008); Green M. R. and Sambrook *J., Molecular Cloning: A Laboratory Manual*, Cold Spring Harbor Laboratory Press, 4$^4$ Edition (2012); Jensen K. J. et al., Peptide Synthesis and Applications (Methods in Molecular Biology), Humana Press, 2$^{nd}$ Edition (2013). Chemically synthesis of a polypeptide can be accomplished by using methodologies well known in the art (see Kelley and Winkler, 1990, In: *Genetic Engineering Principles and Methods*, Setlow J. K, ed., Plenum Press, N.Y., Vol. 12, pp 1-19; Stewart et al., 1984, J. M. Young, J. D., *Solid Phase Peptide Synthesis*, Pierce Chemical Co., Rockford, Ill.; Marglin and Merrifield, *Ann. Rev. Biochem,* 39:841-866, at 862 (1970). Merrifield, R. B., 1963, *J. Am. Chern. Soc.* 85:2149-2154; *Chemical Approaches to the Synthesis of Peptides and Proteins*, Williams et al., Eds., 1997, CRC Press, Boca Raton Fla.; *Solid Phase Peptide Synthesis: A Practical Approach*, Atherton & Sheppard, Eds., 1989, IRL Press, Oxford, England; see also U.S. Pat. Nos. 4,105,603; 3,972,859; 3,842,067; and 3,862,925).

7.2.3. Modifications and Derivatives

Antibodies to glycosylated BTLA can have the ability to neutralize or counteract the effects of glycosylated BTLA regardless of the animal species, monoclonal cell line or other source of the antibody. Certain animal species may be less preferable for generating therapeutic antibodies because they may be more likely to cause allergic response due to activation of the complement system through the Fc portion of the antibody. However, whole antibodies can be enzymatically digested into Fc (complement binding) fragment, and into antibody fragments having the binding domain or CDR. Removal of the Fc portion reduces the likelihood that the antibody fragment will elicit an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

The binding properties of anti-glycosylated BTLA antibodies can be further improved by screening for variants that exhibit desired properties. For example, such improvement can be done using various phage display methods known in the art. In phage display methods, functional antibody domains are displayed on the surface of phage particles which carry the polynucleotide sequences encoding them. In a particular embodiment, such phage can be utilized to display antigen binding fragments, such as Fab and Fv or disulfide-bond stabilized Fv, expressed from a repertoire or combinatorial antibody library (e.g., human or murine). Phage expressing an antigen binding fragment that binds the antigen of interest can be selected or identified with antigen, e.g., using labeled antigen or antigen bound or captured to a solid surface or bead. Phage used in these methods are typically filamentous phage, including fd and M13. The antigen binding fragments are expressed as a recombinantly fused protein to either the phage gene III or gene VIII protein. Examples of phage display methods that can be used to make the antibodies or polypeptides as described herein include those disclosed in Brinkman et al., *J Immunol Methods,* 182:41-50 (1995); Ames et al., *J. Immunol. Methods,* 184:177-186 (1995); Kettleborough et al., *Eur. J Immunol.,* 24:952-958(1994); Persic et al., *Gene,* 187:9-18 (1997); Burton et al., *Adv. Immunol.* 57:191-280 (1994); PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; all of which are hereby incorporated by references in their entireties.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT Publication WO 92/22324; Mullinax, R. L. et al., *BioTechniques,* 12(6):864-869 (1992); and Sawai et al., *Am. J. Reprod. Immunol.* 34:26-34 (1995); and Better, M. et al. *Science* 240:1041-1043(1988); all of which are hereby incorporated by references in their entireties. Examples of techniques which can be used to produce single-chain Fvs and antibodies include those described in U.S. Pat. Nos. 4,946,778 and 5,258,498; Huston, J. S. et al., *Methods in Enzymology* 203:46-88(1991); Shu, L. et al., *Proc. Natl. Acad. Sci*. (USA) 90:7995-7999; and Skerra. A. et al., *Science* 240:1038-1040 (1988); all of which are hereby incorporated by references in their entireties.

Phage display technology can be used to increase the affinity of anti-glycosylated BTLA antibodies as described herein. This technique can be used in obtaining high affinity antibodies that could be used in the combinatorial methods described herein. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al., *J. Immunol.* 149:3903-3913(1992)). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al., *Proc. Natl. Acad. Sci.* (USA) 95(11):6037-6042 (1998); Yelton, D. E. et al., *J. Immunol.* 155:1994-2004 (1995). CDR walking which randomizes the light chain can also be used. (see Schier et al., *J. Mol. Biol.* 263:551-567 (1996)).

Random mutagenesis can be used in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al., *J. Immunol.* 149:3903-3913(1992)).

Methods for accomplishing such affinity maturation are described for example in: Krause, J. C. et al., *MBio.* 2(1) pii: e00345-10. doi: 10.1128/mBio.00345-10(2011); Kuan, C. T. et al., *Int. J. Cancer* 10.1002/ijc.25645; Hackel, B. J. et al., *J. Mol. Biol.* 401(1):84-96(2010); Montgomery, D. L. et al., *MAbs* 1(5):462-474(2009); Gustchina, E. et al., *Virology* 393(1):112-119 (2009); Finlay, W. J. et al., *J. Mol. Biol.* 388(3):541-558 (2009); Bostrom, J. et al., *Methods Mol. Biol.* 525:353-376 (2009); Steidl, S. et al., *Mol. Immunol.* 46(1):135-144 (2008); and Barderas, R. et al., *Proc. Natl. Acad. Sci.* (USA) 105(26):9029-9034 (2008); all of which are hereby incorporated by references in their entireties.

Provided herein are also derivatives of anti-glycosylated BTLA antibodies glycosylated BTLA polypeptides that have one, two, three, four, five or more amino acid substitutions, additions, deletions or modifications relative to a "parental" (or wild-type) molecule. Such amino acid substitutions or additions can introduce naturally occurring (i.e., DNA-encoded) or non-naturally occurring amino acid residues. Such amino acids can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In some embodiments, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al., *J. Biol. Chem.* 277(30): 26733-26740 (2002); Davies J. et al. *Biotechnology & Bioengineering* 74(4): 288-294(2001); all of which are hereby incorporated by references in their entireties). Methods of altering carbohydrate contents are known to those skilled in the art, see, e.g., Wallick, S. C. et al., *J. Exp. Med.* 168(3): 1099-1109(1988); Tao, M. H. et al., *J. Immunol.* 143(8): 2595-2601 (1989); Routledge, E. G. et al., *Transplantation* 60(8):847-53 (1995); Elliott, S. et al., *Nature Biotechnol.* 21:414-21(2003); Shields, R. L. et al., *J. Biol. Chem.* 277(30): 26733-26740 (2002); all of which are hereby incorporated by references in their entireties.

Substitutional variants can contain the exchange of one amino acid for another at one or more sites within the antibodies or polypeptides as provided herein, and can be designed to modulate one or more properties of the antibodies or polypeptide, with or without the loss of other functions or properties. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions can be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some embodiments, a humanized antibody is a derivative antibody. Such a humanized antibody includes amino acid residue substitutions, deletions or additions in one or more non-human CDRs. The humanized antibody derivative can have substantially the same binding, better binding, or worse binding when compared to a non-derivative humanized antibody. In some embodiments, one, two, three, four, or five amino acid residues of the CDR have been mutated, such as substituted, deleted or added.

In some embodiments, a polypeptide is a derivative polypeptide. Such a polypeptide includes amino acid residue substitutions, deletions or additions compared to wildtype human BTLA. The derivative polypeptide can have substantially the same binding, better binding, or worse binding with an anti-glycosylated BTLA antibody as compared with a non-derivative polypeptide. In some embodiments, one, two, three, four, or five amino acid residues of human BTLA have been mutated, such as substituted, deleted or added.

The antibodies or polypeptides as described herein can be modified by chemical modifications using techniques known to those of skill in the art, including, but not limited to, specific chemical cleavage, acetylation, formulation, metabolic synthesis of tunicamycin, etc. In one embodiment, a derivative polypeptide or a derivative antibody possesses a similar or identical function as the parental polypeptide or antibody. In another embodiment, a derivative polypeptide or a derivative antibody exhibits an altered activity relative to the parent polypeptide or parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821; all of which are hereby incorporated by references in their entireties. In some embodiments, the antibodies or other molecules can have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In some embodiments, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivative antibodies or polypeptides can also have altered half-lives (e.g., serum half-lives) of parental molecules or antibodies in a mammal, preferably a human. In some embodiments, such alteration results in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of humanized antibodies or polypeptides in a mammal, preferably a human, results in a higher serum titer of said antibodies or polypeptides in the mammal, and thus, reduces the frequency of the administration of said a antibodies or polypeptides and/or reduces the concentration of said antibodies or polypeptides to be administered. Antibodies or polypeptides having increased in vivo half-lives can be generated by techniques known to those of skill in the art. For example, antibodies or polypeptides with increased in vivo half-lives can be generated by modifying (e.g., substituting, deleting or adding) amino acid residues identified as involved in the interaction between the Fc domain and the FcRn receptor. The humanized antibodies as described herein can be engineered to increase biological half-lives (see, e.g. U.S. Pat. No. 6,277,375). For example, humanized antibodies as described herein can be engineered in the Fc-hinge domain to have increased in vivo or serum half-lives.

Antibodies or polypeptides as described herein with increased in vivo half-lives can be generated by attaching to said antibodies or polypeptides polymer molecules such as high molecular weight polyethyleneglycol (PEG). PEG can be attached to the antibodies or polypeptides with or without a multifunctional linker either through site-specific conjugation of the PEG to the N- or C-terminus of said molecules or antibodies or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies or polypeptides as described herein can also be modified by the methods and coupling agents described by Davis et al. (See U.S. Pat. No. 4,179,337) in order to provide compositions that can be injected into the mammalian circulatory system with substantially no immunogenic response. Removal of the Fc portion can reduce the likelihood that the antibody fragment elicits an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

7.2.4. Fusions and Conjugates

The anti-glycosylated BTLA antibodies or glycosylated BTLA polypeptides provided herein can also be expressed as fusion proteins with other proteins or chemically conjugated to another moiety.

In some embodiments, provided herein are antibodies or polypeptides that have an Fc portion, wherein the Fc portion can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al., *Mol. Immun.* 34(6): 441-452 (1997), Swann, P. G., *Curr. Opin. Immun.* 20:493-499 (2008), and Presta, L. G., *Curr. Opin. Immun.* 20:460-470 (2008). In some embodiments the Fc region is the native IgG1, IgG2, or IgG4 Fc region. In some embodiments the Fc region is a hybrid, for example a chimeric having of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

Another embodiment includes IgG2-4 hybrids and IgG4 mutants that have reduce binding to FcR which increase their half-life. Representative IG2-4 hybrids and IgG4 mutants are described in Angal et al., *Molec. Immunol.* 30(1):105-108 (1993); Mueller et al., *Mol. Immun.* 34(6): 441-452 (1997); and U.S. Pat. No. 6,982,323; all of which are hereby incorporated by references in their entireties. In some embodiments the IgG1 and/or IgG2 domain is deleted for example, Angal et al. describe IgG1 and IgG2 having serine 241 replaced with a proline.

In some embodiments, provided herein are fusion proteins or polypeptides having at least 10, at least 20, at least 30, at least 40, at least 50, at least 60, at least 70, at least 80, at least 90 or at least 100 amino acids.

In some embodiments, provided herein are anti-glycosylated BTLA antibodies or glycosylated BTLA polypeptides that link to or covalently bind or form into a complex with at least one moiety. Such a moiety can be, but is not limited to, one that increases the efficacy of molecules as diagnostic or therapeutic agents. In some embodiments, the moiety can be image agents, toxins, therapeutic enzymes, antibiotics, radio-labeled nucleotides and the like.

Molecules provided herein can include a therapeutic moiety (or one or more therapeutic moieties). Molecules provided herein can be an antibody conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458, 935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, molecules provided herein be antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7, 10-tetraazacyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50, each incorporated by reference in their entireties.

The therapeutic moiety or drug conjugated or recombinantly fused to an antibody provided herein that immunospecifically binds to BTN1A1 should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

In some embodiments, the moiety can be enzymes, hormones, cell surface receptors, toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-PA biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CAN- CER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., *Nat. Biotechnol.* 21(7):778-784(2003); Ducry et al., *Bioconjug Chem.* 21(1):5-13(2010); Senter, *Curr. Opin. Chem. Biol.* 13(3):235-244 (2009); and Teicher, *Curr Cancer Drug Targets.* 9(8):982-1004 (2009).

In some embodiments, antibodies and polypeptides as described herein can be conjugated to a marker, such as a peptide, to facilitate purification. In some embodiments, the marker is a hexa-histidine peptide, the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some embodiments, the moiety can be an image agent that can be detected in an assay. Such image agent can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, colored particles or ligands, such as biotin.

In some embodiments, the enzymes include, but not limited to, horseradish peroxidase, alkaline phosphatase, beta-galactosidase, or acetylcholinesterase; the prosthetic group complexes include, but not limited to, streptavidin/biotin and avidin/biotin; the fluorescent materials include, but not limited to, umbelliferone, fluorescein, fluorescein isothiocyanate, rhodamine, dichlorotriazinylamine fluorescein, dansyl chloride or phycoerythrin; the luminescent material such as, but not limited to, luminol; the bioluminescent materials include, but not limited to, luciferase, luciferin, and aequorin; the radioactive material include, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{10}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{85}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The image agent can be conjugated to the antibodies or polypeptides as described herein either directly, or indirectly through an intermediate (such as, for example, a linker known in the art) using techniques known in the art. See, for example, U.S. Pat. No. 4,741,900 for metal ions which can be conjugated to antibodies and other molecules as described herein for use as diagnostics. Some conjugation methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

In some embodiments, the antibodies or polypeptides as described herein can be conjugated to a second antibody to form an antibody heteroconjugate as described by Segal in U.S. Pat. No. 4,676,980. Such heteroconjugate antibodies can additionally bind to haptens (e.g., fluorescein), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

In some embodiments, the anti-glycosylated BTLA antibodies or glycosylated BTLA polypeptides described herein can also be attached to solid supports, which can be useful for immunoassays or purification of the target antigen or of other molecules that are capable of binding to target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

7.2.5. Protein Purification

Protein purification techniques are well known to those of skill in the art. These techniques involve, at one level, the homogenization and crude fractionation of the cells, tissue, or organ into polypeptide and non-polypeptide fractions. The protein or polypeptide of interest can be further purified using chromatographic and electrophoretic techniques to achieve partial or complete purification (or purification to homogeneity) unless otherwise specified. Analytical methods particularly suited to the preparation of a pure peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, it is believed that the order of conducting the various purification steps can be changed, or that certain steps may be omitted, and still result in a suitable method for the preparation of a substantially purified polypeptide.

A purified polypeptide is intended to refer to a composition, isolatable from other components, wherein the polypeptide is purified to any degree relative to its naturally-obtainable state. An isolated or purified polypeptide, therefore, also refers to a polypeptide free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a composition in which the polypeptide forms the major component of the composition, such as constituting about 50%, about 60%, about 70%, about 80%, about 90%, about 95%, or more of the proteins in the composition.

Various methods for quantifying the degree of purification of the polypeptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed polypeptide exhibits a detectable activity.

There is no general requirement that the polypeptide will always be provided in its most purified state. Indeed, it is contemplated that less substantially purified products can have utility in certain embodiments. Partial purification can be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

Provided herein also is a method for assessing BTLA glycosylation, N-linked glycosylation or N-glycosylation comprising contacting the BTLA-containing sample with an antibody of the embodiments (e.g., an antibody selectively binds to glycosylated BTLA relative to unglycosylated BTLA). In some aspects, the method is an in vitro method. In certain aspects, the sample is cell sample.

7.2.6. Nucleic Acids.

The present disclosure also contemplates nucleic acid molecules (DNA or RNA) that encode any anti-glycosylated BTLA antibodies or glycosylated BTLA polypeptides as described herein. Provided herein are also vector molecules (such as plasmids) that are capable of transmitting or of replication such nucleic acid molecules. The nucleic acids can be single-stranded, double-stranded, and can contain both single-stranded and double-stranded portions.

7.3. Pharmaceutical Preparations

Where clinical application of a pharmaceutical composition containing an antibody is undertaken, it will generally be beneficial to prepare a pharmaceutical or therapeutic composition appropriate for the intended application. Generally, pharmaceutical compositions can have an effective amount of anti-glycosylated BTLA antibodies or glycosylated BTLA polypeptides as described herein, or with additional agents dissolved or dispersed in a pharmaceutically acceptable carrier.

Provided herein are also compositions having anti-glycosylated BTLA antibodies or glycosylated BTLA polypeptides as described herein. In some embodiments, the composition can have at least 0.1% by weight the antibodies or polypeptides. In some embodiments, the composition can have at least 0.5%, 1%, 2%, 3%, 4%, 5%, 6%, 7% 8%, 9%, 10%, 15%, 20%, 25%, 30%, 35%, 40%, 45%, 50%, 55%, 60%, 65%, 70%, 75%, 80%, 85%, 90%, or more by weight of anti-glycosylated BTLA antibodies or glycosylated BTLA polypeptides. In other embodiments, for example, anti-glycosylated BTLA or glycosylated BTLA polypeptides can constitute between about 2% to about 75% of the weight of the composition, between about 25% to about 60%, between about 30% to about 50%, or any range therein. The amount of active compound(s) in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In some embodiments, the pharmaceutical compositions can have an anti-glycosylated BTLA antibody that comprises the VH or VL domain of the murine monoclonal antibody STC613, as depicted in Table 2. In some embodiments, the pharmaceutical compositions can have an anti-glycosylated BTLA antibody that comprises the VH or VL domain of the murine monoclonal antibody STC626, as depicted in Table 4. In some embodiments, the pharmaceutical compositions can have an anti-glycosylated BTLA antibody that comprises the VH or VL domain of the murine monoclonal antibody STC635, as depicted in Table 6.

In some embodiments, the pharmaceutical compositions can have an anti-glycosylated BTLA antibody that comprises both the VH and VL domain of the murine monoclonal antibody STC613, as depicted in Table 2. In some embodiments, the pharmaceutical compositions can have an anti-glycosylated BTLA antibody that comprises both the VH and VL domain of the murine monoclonal antibody STC626, as depicted in Tables 4. In some embodiments, the pharmaceutical compositions can have an anti-glycosylated BTLA antibody that comprises both the VH and VL domain of the murine monoclonal antibody STC635, as depicted in Table 6.

In some embodiments, the pharmaceutical compositions can have an anti-glycosylated BTLA antibody that comprises one or more VH CDRs having the amino acid sequence of any one of the VH CDRs of the murine monoclonal antibody STC613, as depicted in Table 3. In some embodiments, the pharmaceutical compositions can have an anti-glycosylated BTLA antibody that comprises one or more VH CDRs having the amino acid sequence of any one of the VH CDRs of the murine monoclonal antibody STC626, as depicted in Table 5. In some embodiments, the pharmaceutical compositions can have an anti-glycosylated BTLA antibody that comprises one or more VH CDRs having the amino acid sequence of any one of the VH CDRs of the murine monoclonal antibody STC635, as depicted in Table 7.

In some embodiments, the pharmaceutical compositions can have an anti-glycosylated BTLA antibody that comprises one or more VL CDRs having the amino acid sequence of any one of the VL CDRs of the murine monoclonal antibody STC613, as depicted in Table 3. In some embodiments, the pharmaceutical compositions can have an anti-glycosylated BTLA antibody that comprises one or more VL CDRs having the amino acid sequence of any one of the VL CDRs of the murine monoclonal antibody STC626, as depicted in Table 5. In some embodiments, the pharmaceutical compositions can have an anti-glycosylated BTLA antibody that comprises one or more VL CDRs having the amino acid sequence of any one of the VL CDRs of the murine monoclonal antibody STC635, as depicted in Table 7.

In some embodiments, the pharmaceutical compositions can have an anti-glycosylated BTLA antibody that comprises at least one VH CDR and at least one VL CDR of the murine monoclonal antibody STC613, as depicted in Table 3. In some embodiments, the pharmaceutical compositions can have an anti-glycosylated BTLA antibody that comprises at least one VH CDR and at least one VL CDR of the murine monoclonal antibody STC626, as depicted in Table 5. In some embodiments, the pharmaceutical compositions can have an anti-glycosylated BTLA antibody that comprises at least one VH CDR and at least one VL CDR of the murine monoclonal antibody STC635, as depicted in Table 7.

In some embodiments, the pharmaceutical compositions can have an anti-glycosylated BTLA antibody that competitively blocks (e.g., in a dose-dependent manner) a BTLA epitope described herein. The BTLA epitope can be an epitope of STC613 as described herein. In some embodiments, the pharmaceutical compositions can have an anti-glycosylated BTLA antibody that specifically binds to an epitope of BTLA as described herein. The BTLA epitope can be an epitope of STC613 as described herein. In some embodiments, the BTLA epitope has at least five consecutive amino acids of an amino acid sequence of SEQ ID NOS: 161, 162, 163, 164, 165, 166, 167, 168, or 169.

The composition can be a pharmaceutical composition having anti-glycosylated BTLA antibodies or glycosylated BTLA polypeptides as the active ingredient as well as a pharmaceutically acceptable carrier. The pharmaceutical composition can further include one or more additional active ingredient. A pharmaceutically acceptable carrier can be a carrier approved by a regulatory agency of the Federal or a state government, or listed in the U.S. Pharmacopeia, European Pharmacopeia or other generally recognized Pharmacopeia for use in animals, and more particularly in humans.

As used herein, and unless otherwise specified, the term "carrier" refers to a diluent, adjuvant (e.g., Freund's adjuvant (complete or incomplete)), excipient, stabilizers or vehicle with which a therapeutic agent is administered. A "pharmaceutically acceptable carrier" is a carrier that is nontoxic to the cell or mammal being exposed thereto at the dosages and concentrations employed, which can be sterile liquids, such as water and oils, including those of petroleum, animal, vegetable or synthetic origin, such as peanut oil, soybean oil, mineral oil, sesame oil and the like. Pharmaceutically acceptable molecular entities or compositions do not produce an adverse, allergic, or other untoward reaction when administered to an animal, such as a human, as appropriate. The preparation of a pharmaceutical composition having an antibody or additional active ingredient is known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by FDA Office of Biological Standards.

It is contemplated that the compositions include about 0.001 mg and about 10 mg of total antibodies or polypeptides per ml. Thus, the concentration of antibodies or polypeptides in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% can be an anti-glycosylated BTLA antibody or a glycosylated BTLA polypeptide.

The preparation of a pharmaceutical composition having the antibodies or other polypeptides as described herein as active ingredient are known to those of skill in the art in light of the present disclosure, as exemplified by Remington's Pharmaceutical Sciences, 18th Ed., 1990, incorporated herein by reference. Moreover, for animal (including human) administration, it is understood that preparations should meet sterility, pyrogenicity, general safety, and purity standards as required by FDA Office of Biological Standards.

The pharmaceutically acceptable carriers include liquid, semi-solid, i.e., pastes, or solid carriers. Examples of carriers or diluents include fats, oils, water, saline solutions, lipids, liposomes, resins, binders, fillers, and the like, or combinations thereof. The pharmaceutically acceptable carrier can include aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, anti-oxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present disclosure, the composition can be combined with the carrier in any convenient and practical manner, i.e., by solution, suspension, emulsification, admixture, encapsulation, absorption, grinding, and the like. Such procedures are routine for those skilled in the art.

In some embodiments, a pharmaceutically acceptable carrier can be an aqueous pH buffered solution. Examples include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In some embodiments, pharmaceutically acceptable carriers can be sterile liquids, such as water and oils, including those of petroleum, animal, vegetable or synthetic origin, such as peanut oil, soybean oil, mineral oil, sesame oil and the like. Water can be a carrier, particularly when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition can also contain minor amounts of wetting or emulsifying agents, or pH buffering agents. These compositions can take the form of solutions, suspensions, emulsion, tablets, pills, capsules, powders, sustained-release formulations and the like.

Certain embodiments of the present disclosure can have different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The anti-glycosylated BTLA antibodies or glycosylated BTLA polypeptides can be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, 2-ethylamino ethanol, histidine, or procaine.

In further embodiments, provided herein are pharmaceutical compositions having a lipid. A lipid can broadly include a class of substances that are characteristically insoluble in water and extractable with an organic solvent. Examples include compounds that contain long-chain aliphatic hydrocarbons and their derivatives. A lipid can be naturally occurring or synthetic (i.e., designed or produced by man). A lipid can be a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Compounds other than those specifically described herein that are understood by one of skill in the art as lipids can also be used.

One of ordinary skill in the art would be familiar with the range of techniques that can be employed for dispersing a composition in a lipid vehicle. For example, antibodies or polypeptides can be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of active ingredient in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, can be contemplated by one skilled in the art of preparing such pharmaceutical formulations, and as such, a variety of dosages and treatment regimens may be desirable.

A unit dose or dosage refers to physically discrete units suitable for use in a subject, each unit containing a predetermined quantity of the pharmaceutical composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose can have from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

As a person of ordinary skill in the art would understand, the compositions described herein are not limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual subjects. The actual dosage amount of a composition administered to an animal patient, including a human patient, can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

7.4. Treatment of Diseases

As used herein, and unless otherwise specified, the term "subject" refers to an animal that is the object of treatment, observation and/or experiment. "Animal" includes vertebrates and invertebrates, such as fish, shellfish, reptiles, birds, and, in particular, mammals. "Mammal" includes, but not limited to, mice, rats, rabbits, guinea pigs, dogs, cats, sheep, goats, cows, horses, primates, such as monkeys, chimpanzees, apes, and humans. In some embodiments, the subject is a human.

As used herein, and unless otherwise specified, the term "cancer" or "cancerous" refers to the physiological condition in mammals that is typically characterized by unregulated cell growth. Examples of cancer include, but are not limited to, hematological cancers and solid tumors.

As used herein, and unless otherwise specified, the term "treat," "treating," or "treatment" refer to administration or application of a therapeutic agent to a subject or performance of a procedure or modality on a subject for the purpose of obtaining a therapeutic benefit of a disease or health-related condition. For example, a treatment can include administration of a therapeutically effective amount of an anti-glycosylated BTLA antibody to a subject. When used in reference to a cancer patient, the term "treat," "treating," or "treatment" refers to an action that potentially reduces the severity of the cancer, or retards or slows the progression of the cancer, including (a) inhibiting the cancer growth, reducing cancer growth rate, arresting development, reducing cancer invasiveness or preventing metastasis of the cancer, and (b) causing regression of the cancer, delaying or minimizing one or more symptoms associated with the presence of the cancer, or prolonging the survival of a cancer patient.

As used herein, and unless otherwise specified, the term "therapeutically effective amount" refers to the amount of an agent (e.g., an antibody or a polypeptide described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A therapeutically effective amount of a substance/molecule/agent of the present disclosure (e.g., an anti-glycosylated BTLA antibody) can vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects.

As used herein, and unless otherwise specified, the term "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

Provided herein are also therapeutic uses of the anti-glycosylated BTLA antibodies (e.g., STC613, STC626, or STC635) and glycosylated BTLA polypeptides. These antibodies or polypeptides can be used to modulate the activity of BTLA signaling. These antibodies or polypeptides can also be used treat a disease by inhibiting the suppressive activity of BTLA in T cell activation or proliferation. Accordingly, provided herein are uses of such antibodies or polypeptides in up-modulating the immune system of a subject by inhibiting or blocking the BTLA signaling.

In some embodiments, provided herein are also therapeutic uses of the anti-glycosylated BTLA antibodies (e.g., STC613, STC626, or STC635) and glycosylated BTLA polypeptides in treating cancer. Up-modulation of the immune system is particularly desirable in the treatment of cancers, and thus provided herein are also methods of cancer treatment. A cancer refers to a neoplasm or tumor resulting from abnormal uncontrolled growth of cells. A cancer can be a primary cancer or a metastatic cancer.

In some embodiments, the anti-glycosylated BTLA antibodies provided herein (e.g. STC613, STC626, or STC635 or humanized variants thereof) can modulate an immune response in a subject. In some embodiments, the anti-glycosylated BTLA antibodies provided herein can promote T cell activation. In some embodiments, the anti-glycosylated BTLA antibodies provided herein can promote T cell proliferation. In some embodiments, the anti-glycosylated BTLA antibodies provided herein can increase cytokine production. In some embodiments, the anti-glycosylated BTLA antibodies provided herein can also enhance T-cell dependent apoptosis of a cell expressing BTLA or inhibit the proliferation of cells expressing BTLA.

Accordingly, provided herein are methods of modulating an immune response in a subject by administering an effective amount of an anti-glycosylated BTLA antibody provided herein (e.g., STC613, STC626, or STC635 or humanized variants thereof). Modulating an immune response can include (a) increasing T cell activation; (b) increasing T cell proliferation; and/or (c) increasing cytokine production.

In some embodiments, provided herein are therapeutic uses of anti-glycosylated BTLA antibodies having antigen binding fragment that comprises the VH or VL domain of the murine monoclonal antibody STC613, as depicted in Table 2, the murine monoclonal antibody STC626, as depicted in Table 4, or the murine monoclonal antibody STC635, as depicted in Table 6. In some embodiments, the anti-glycosylated BTLA antibodies can have an antigen binding fragment that comprises both the VH and VL domain of the murine monoclonal antibody STC613, as depicted in Table 2, the murine monoclonal antibody STC626, as depicted in Table 4, or the murine monoclonal antibody STC635, as depicted in Table 6. In some embodiments, provided herein are therapeutic uses of anti-glycosylated BTLA antibodies comprising one or more VH CDRs having the amino acid sequence of any one of the VH CDRs of the murine monoclonal antibody STC613, as depicted in Table 2, the murine monoclonal antibody STC626, as depicted in Table 4, or the murine monoclonal antibody STC635, as depicted in Table 6. In some embodiments, the anti-glycosylated BTLA antibodies comprise one or more VL CDRs having the amino acid sequence of any one of the VL CDRs of the murine monoclonal antibody STC613, as depicted in Table 2, the murine monoclonal antibody STC626, as depicted in Table 4, or the murine monoclonal antibody STC635, as depicted in Table 6. In some embodiments, the anti-glycosylated BTLA antibodies comprise at least one VH CDR and at least one VL CDR of the murine monoclonal antibody STC613, as depicted in Table 2, the murine monoclonal antibody STC626, as depicted in Table 4, or the murine monoclonal antibody STC635, as depicted in Table 6.

In some embodiments, provided herein are therapeutic uses of anti-glycosylated BTLA antibodies that competitively block (e.g., in a dose-dependent manner) a BTLA epitope described herein. The BTLA epitope can be an epitope of STC613 as described herein. In some embodiments, provided herein are therapeutic uses of anti-glycosylated BTLA antibodies that specifically bind to an epitope of BTLA as described herein. The BTLA epitope can be an epitope of STC613 as described herein. In some embodiments, the BTLA epitope has at least five consecutive amino acids of an amino acid sequence of SEQ ID NOS: 161, 162, 163, 164, 165, 166, 167, 168, or 169.

Provided herein are also therapeutic uses of anti-glycosylated BTLA antibodies provided herein. In some embodiments, the anti-glycosylated BTLA antibodies provided herein bind specifically to glycosylated BTLA. In some embodiments, the anti-glycosylated BTLA antibodies specifically bind to BTLA glycosylated at positions N75, N94, N110 or any combination thereof. In some embodiments, the anti-glycosylated BTLA antibodies specifically bind to BTLA glycosylated at position N75. In some embodiments, the anti-glycosylated BTLA antibodies specifically bind to BTLA glycosylated at position N94. In some embodiments, the anti-glycosylated BTLA antibodies specifically bind to BTLA glycosylated at position N110. In some embodiments, the anti-glycosylated BTLA antibodies specifically bind to BTLA glycosylated at positions N75 and N94. In some embodiments, the anti-glycosylated BTLA antibodies specifically bind to BTLA glycosylated at positions N75 and N110. In some embodiments, the anti-glycosylated BTLA antibodies specifically bind to BTLA glycosylated at positions N94 and N110. In some embodiments, the anti-glycosylated BTLA antibodies specifically bind to BTLA glycosylated at positions N75, N94 and N110.

In certain aspects, a polypeptide or antibody of the embodiments (e.g., a glycosylated BTLA polypeptide or an antibody that binds to glycosylated BTLA, such as STC613, STC626, or STC635) can be administered to treat a cancer. Cancers for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer can specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the antibodies or polypeptides provided herein can be used to treat a cancer that is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

The polypeptide or antibody can be used herein as an antitumor agent in a variety of modalities. In a particular embodiment, provided herein are methods of using a polypeptide or antibody as an antitumor agent, and therefore comprises contacting a population of tumor cells with a therapeutically effective amount of a polypeptide or antibody for a time period sufficient to inhibit tumor cell growth.

Various delivery systems are also known and can be used to administer the anti-glycosylated BTLA antibodies or related molecules, or related pharmaceutical compositions, such as encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262:4429-4432), construction of a nucleic acid as part of a retroviral or other vector, etc.

The methods of administration as provided herein include, but are not limited to, injection, as by parenteral administration (e.g., intradermal, intramuscular, intraperitoneal, intravenous and subcutaneous), epidural, and mucosal (e.g., intranasal and oral routes). In some embodiments, the antibodies, other molecules, or pharmaceutical compositions provided herein are administered intramuscularly, intravenously, subcutaneously, intravenously, intraperitoneally, orally, intramuscularly, subcutaneously, intracavity, transdermally, or dermally. The compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903; all of which are hereby incorporated by reference in their entireties. In some embodiments, the antibodies, other molecules, or pharmaceutical compositions provided herein are administered locally to the area in need of treatment, which can be achieved by, for example, local infusion, by injection, or by means of an implant, said implant being of a porous, non-porous, or gelatinous material, including membranes, such as sialastic membranes, or fibers. In some embodiments, when administering antibodies or other molecules as described herein, care is taken to use materials to which the antibodies or other molecules do not absorb.

In some embodiments, the antibodies or polypeptides provided herein are formulated in liposomes for targeted delivery. Liposomes are vesicles comprised of concentrically ordered phopsholipid bilayers which encapsulate an aqueous phase. Liposomes typically have various types of lipids, phospholipids, and/or surfactants. The components of liposomes are arranged in a bilayer configuration, similar to the lipid arrangement of biological membranes. Liposomes can be useful delivery vehicles due, in part, to their biocompatibility, low immunogenicity, and low toxicity. Methods for preparation of liposomes are known in the art and are provided herein, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545; all of which are hereby incorporated by reference in their entireties.

Provided herein are also methods of preparing liposomes with a prolonged serum half-life, i.e., enhanced circulation time, such as those disclosed in U.S. Pat. No. 5,013,556. In some embodiments, liposomes used in the methods provided herein are not rapidly cleared from circulation, i.e., are not taken up into the mononuclear phagocyte system (MPS). Provided herein are also sterically stabilized liposomes which are prepared using common methods known to one skilled in the art. Sterically stabilized liposomes can contain lipid components with bulky and highly flexible hydrophilic moieties, which reduces the unwanted reaction of liposomes with serum proteins, reduces oposonization with serum components and reduces recognition by MPS. Sterically stabilized liposomes can be prepared using polyethylene glycol. For preparation of liposomes and sterically stabilized liposome, see, e.g., Bendas et al., 2001 BioDrugs, 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *J. Chem. Pharm. Bull.,* 39: 1620-2; Klibanov et al., 1991, *J., Biochim Biophys Acta,* 1062; 142-8; Allen et al., 1994, *Adv. Drug Deliv. Rev,* 13: 285-309, which are hereby incorporated by reference in their entireties.

Provided herein are also liposomes that are adapted for specific organ targeting, see, e.g., U.S. Pat. No. 4,544,545, or specific cell targeting, see, e.g., U.S. Patent Application Publication No. 2005/0074403, which are hereby incorporated by reference in their entireties. Particularly useful liposomes for use in the compositions and methods provided herein can be generated by reverse phase evaporation method with a lipid composition comprising phosphatidylcholine, cholesterol, and PEG derivatized phosphatidylethanolamine (PEG-PE). Liposomes can be extruded through filters of defined pore size to yield liposomes with the desired diameter. In some embodiments, a molecule having an antigen binding fragment, e.g., F(ab'), can be conjugated to the liposomes using previously described methods, see, e.g., Martin et al., 1982, *J. Biol. Chem.* 257: 286-288, which is hereby incorporated by reference in its entirety.

The humanized or chimeric antibodies as described herein can also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, *Stealth Liposomes,* Boca Rotan: CRC Press, 233-44; Hansen et al., 1995, *Biochim. Biophys. Acta,* 1239: 133-144, which are hereby incorporated by reference in their entireties. In some embodiments, immunoliposomes for use in the methods and compositions provided herein are further sterically stabilized. In some embodiments, the humanized antibodies as described herein are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art can be used, see, e.g., J. Thomas August ed., 1997, *Gene Therapy: Advances in Pharmacology,* Volume 40, Academic Press, San Diego, Calif., p. 399-435, which are hereby incorporated by reference in their entireties. For example, a functional group on an antibody molecule can react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry,* 35: 1100-1105; Loughrey et al., 1987, *Biochim. Biophys. Acta,* 901: 157-160; Martin et al., 1982, 1 *Biol. Chem.* 257: 286-288; Martin et al., 1981, *J., Biochemistry,* 20: 4429-38, which are hereby incorporated by reference in their entireties. The immunoliposomal formulations having the anti-glycosylated BTLA antibodies can be particularly effective as therapeutic agents, since they deliver the active ingredient to the cytoplasm of the target cell, i.e., the cell comprising the receptor to which the antibody binds. In some embodiments, the immunoliposomes can have an increased half-life in blood, specifically target cells, and can be internalized into the cytoplasm of the target cells thereby avoiding loss of the therapeutic agent or degradation by the endolysosomal pathway.

The immunoliposomal compositions provided herein can have one or more vesicle forming lipids, an antibody or other molecule of the invention or a fragment or derivative thereof, and, optionally, a hydrophilic polymer. A vesicle forming lipid can be a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations provided herein are known to one skilled in the art and encompassed within the description. In some embodiments, the immunoliposomal compositions further include a hydrophilic polymer, e.g., polyethylene glycol, and ganglioside GM1, which increases the serum half-life of the liposome. Methods of conjugating hydrophilic polymers to liposomes are well known in the art and encompassed within the description. Additional exemplary immunoliposomes and methods of preparing them can be find in, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August ed., 1997, *Gene Therapy: Advances in Pharmacology*, Volume 40, Academic Press, San Diego, Calif., p. 399-435; all of which are hereby incorporated by reference in their entireties.

Provided herein are also methods of treating a cancer patient by administering a unit dose to the patient the anti-glycosylated BTLA antibodies. Provided herein are also methods of treating a cancer patient by administering a unit dose to the patient glycosylated BTLA polypeptides. A unit dose refers to physically discrete units suitable as unitary dosage for the subject, each unit containing a predetermined quantity of active material calculated to produce the desired therapeutic effect in association with the required diluent, i.e., carrier, or vehicle.

The antibodies, polypeptides, or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual subject. However, suitable dosage ranges for systemic application are disclosed herein and depend on the route of administration. Suitable regimes for initial and booster administration are also contemplated and typically include by an initial administration followed by repeated doses at one or more hour intervals by a subsequent injection or other administration. Exemplary multiple administrations are described herein and are useful to maintain continuously high serum and tissue levels of polypeptide or antibody. Alternatively, continuous intravenous infusion sufficient to maintain concentrations in the blood in the ranges specified for in vivo therapies are contemplated.

A therapeutically effective amount is a predetermined amount calculated to achieve the desired effect. Generally, the dosage will vary with age of, condition of, sex of, and extent of the disease in the patient and can be determined by one of skill in the art. The dosage can be adjusted by the individual physician in the event of any complication.

In some embodiments, the antibodies, polypeptides, or pharmaceutical compositions provided herein are packaged in a hermetically sealed container, such as an ampoule or sachette. In one embodiment, the antibodies, polypeptides, or pharmaceutical compositions provided herein are supplied as a dry sterilized lyophilized powder or water free concentrate in a hermetically sealed container and can be reconstituted, e.g., with water or saline to the appropriate concentration for administration to a subject. In some embodiments, the antibodies, polypeptides, or pharmaceutical compositions provided herein are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies, polypeptides, or pharmaceutical compositions provided herein should be stored at between 2 and 8° C. in their original container and should be administered within 12 hours, preferably within 6 hours, within 5 hours, within 3 hours, or within 1 hour after being reconstituted. In an alternative embodiment, the antibodies, polypeptides, or pharmaceutical compositions provided herein are supplied in liquid form in a hermetically sealed container indicating the quantity and concentration of the antibodies, polypeptides, or pharmaceutical compositions. In some embodiments, the liquid form of the antibodies, polypeptides, or pharmaceutical compositions provided herein are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For the anti-glycosylated BTLA antibodies or glycosylated BTLA polypeptides, the dosage administered to a patient is typically 0.01 mg/kg to 100 mg/kg of the patient's body weight. In some embodiments, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the dosage administered to a patient can be 0.2 mg/kg, 0.3 mg/kg, 1 mg/kg, 3 mg/kg, 6 mg/kg or 10 mg/kg. A dose as low as 0.01 mg/kg is predicted to show appreciable pharmacodynamic effects. Dose levels of 0.10-1 mg/kg are predicted to be most appropriate. Higher doses (e.g., 1-30 mg/kg) can also be expected to be active. Generally, human antibodies have a longer half-life within the human body than antibodies from other species due to the immune response to the foreign polypeptides. Thus, lower dosages of human antibodies and less frequent administration can be practiced. Further, the dosage and frequency of administration of antibodies or polypeptides provided herein can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations having one or more antibodies, molecules, or pharmaceutical compositions provided herein. See, e.g., U.S. Pat. No. 4,526,938; PCT publication WO 91/05548; PCT publication WO 96/20698; Ning et al., *Radiotherapy & Oncology* 39:179-189 (1996), Song et al., *PDA Journal of Pharmaceutical Science & Technology* 50:372-397 (1995); Cleek et al., *Pro. Int'l. Symp. Control. Rel. Bioact. Mater.* 24:853-854 (1997); and Lam et al., Proc. *In'l. Symp. Control Rel. Bioact. Mater.* 24:759-760(1997); all of which are hereby incorporated by reference in their entireties. In one embodiment, a pump can be used in a controlled release system (See Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of antibodies or polypeptides (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253); all of which are hereby incorporated by references in their entireties.

Examples of polymers that can be used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (see U.S. Pat. No. 5,945,155), which is hereby incorporated by references in its entirety. Based upon the therapeutic effect of the in situ controlled release of the bioactive material from the polymer system, the implantation can generally occur anywhere within the body of the patient in need of therapeutic treatment.

In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533). Controlled release systems are also discussed in the review by Langer (1990, *Science* 249:1527-1533). Any technique known to one of skill in the art can be used to produce sustained release formulations comprising one or more therapeutic agents provided herein. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760; all of which are hereby incorporated by references in their entireties.

Provided herein are also embodiment wherein the composition has nucleic acids encoding antibodies or polypeptides as provided herein, wherein the nucleic acid can be administered in vivo to promote expression of its encoded antibody or polypeptide, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

Treatment of a subject with a therapeutically effective amount of antibodies, polypeptides or pharmaceutical composition provided herein can include a single treatment or a series of treatments. It is contemplated that the antibodies, polypeptides, or pharmaceutical compositions provided herein can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive. In some embodiments, they can be administered after the regression of primary cancer to prevent metastasis.

7.5. Combination Treatments

In certain embodiments, the compositions and methods of the embodiments involve administration of glycosylated BTLA polypeptide or an antibody that selectively binds to glycosylated BTLA, in combination with a second or additional therapy. Such therapy can be applied in the treatment of any disease that is associated with BTLA or glycosylated BTLA. For example, the disease can be a cancer, and the second therapy is an anticancer or anti-hyperproliferative therapy.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process can involve administering a polypeptide or antibody and a second therapy. The second therapy may or may not have a direct cytotoxic effect. For example, the second therapy can be an agent that upregulates the immune system without having a direct cytotoxic effect. A tissue, tumor, or cell can be exposed to one or more compositions or pharmacological formulation(s) comprising one or more of the agents (e.g., an antibody or an anti-cancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The anti-glycosylated BTLA antibodies or glycosylated BTLA polypeptides can be administered before, during, after, or in various combinations relative to a second or an additional anti-cancer treatment. The administrations can be in intervals ranging from concurrently to minutes to days to weeks. In embodiments where the antibodies or polypeptides are provided to a patient separately from an anti-cancer agent, one would generally ensure that a significant period of time do not expire between the time of each delivery, such that the two compounds would still be able to exert an advantageously combined effect on the patient. In such instances, it is contemplated that one can provide a patient with the anti-glycosylated BTLA antibodies or glycosylated BTLA polypeptides and the second therapy within about 12 to 24 or 72 h of each other and, more particularly, within about 6-12 h of each other. In some situations the time period for treatment can be extended significantly where several days (2, 3, 4, 5, 6, or 7) to several weeks (1, 2, 3, 4, 5, 6, 7, or 8) lapse between respective administrations.

In certain embodiments, a course of treatment can last 1-90 days or more (this such range includes intervening days). It is contemplated that one agent can be given on any day of day 1 to day 90 (this such range includes intervening days) or any combination thereof, and another agent is given on any day of day 1 to day 90 (this such range includes intervening days) or any combination thereof. Within a single day (24-hour period), the patient can be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. The treatment cycles can be repeated as necessary.

Various combinations can be employed. Listed below are some examples with the treatment with the anti-glycosylated BTLA antibody or glycosylated BTLA polypeptide as "A" and a second anti-cancer therapy as "B":

A/B/A B/A/B B/B/A A/A/B A/B/B B/A/A A/BBB B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any antibodies, polypeptides, or pharmaceutical compositions provided herein, in combination of a second therapy to a patient will follow general protocols for the administration of such second therapy, taking into account the toxicity, if any, of the second therapy. Therefore, in some embodiments there is a step of monitoring toxicity that is attributable to combination therapy.

Chemotherapy

A wide variety of chemotherapeutic agents can be used in accordance with the present embodiments as the second therapy. A chemotherapeutic can be a compound or composition that is administered in the treatment of cancer. These agents or drugs can be categorized by their mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammal1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

Radiotherapy

Another conventional anticancer therapy that can be used in combination with the methods and compositions described herein is radiotherapy, or radiation therapy. Radiotherapy include using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

Tumor microenvironment is intrinsically inhibitory due to the presence of myeloid-derived suppressor cells and regulatory T cells that infiltrate the tumor and function to suppress immune responses. In addition, the expression of certain inhibitory molecules on T cells and antigen presenting cells (APCs) can limit effective immune responses. Radiation mediates anti-tumor effects through the induction of tumor cell apoptosis, senescence, autophagy, and in some situations, can stimulate more effective immune responses.

The abscopal effect is a physiological process whereby targeted radiation of a primary tumor induces an anti-tumor response at a distant site that is not in the field of radiation. The mechanisms responsible for the abscopal effect are thought to be immune mediated and involve enhanced presentation of tumor antigens to T cells as well as the release of cytokines and other pro-inflammatory factors that stimulate local and systemic immune responses. As the abscopal effect affects tumors distally located from the primary tumor that receives radiation treatment, an agent that can trigger the abscopal effect would be particularly advantageous in treating metastatic tumors, which are often more difficult to treat once they have spread to secondary sites within the body.

The anti-glycosylated BTLA antibodies or glycosylated BTLA polypeptides described herein can stimulate local and systemic immune response. In some embodiments, a therapeutically effective amount of the antibodies, polypeptides or pharmaceutical compositions as described herein are administered before, at the same time with, or after a radiotherapy to achieve a synergistic abscopal effect.

In some embodiments, a therapeutically effective amount of the antibodies, polypeptides or pharmaceutical compositions described herein are administered that effectively sensitizes a tumor in a host to irradiation. Irradiation can be ionizing radiation and in particular gamma radiation. In some embodiments, the gamma radiation is emitted by linear accelerators or by radionuclides. The irradiation of the tumor by radionuclides can be external or internal.

In some embodiments, the administration of the antibodies, polypeptides or pharmaceutical compositions described herein commences up to one month, in particular up to 10 days or a week, before the irradiation of the tumor. Additionally, irradiation of the tumor is fractionated the administration of the antibodies, polypeptides or pharmaceutical compositions described herein is maintained in the interval between the first and the last irradiation session.

Irradiation can be also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapy

The skilled artisan will understand that immunotherapies can be used in combination or in conjunction with methods of the embodiments. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, are another such example. The immune effector can be, for example, an antibody specific for some marker on the surface of a tumor cell. The antibody alone can serve as an effector of therapy or it can recruit other cells to actually affect cell killing. The antibody also can be conjugated to a drug or toxin (e.g., chemotherapeutic, radionuclide, ricin A chain, cholera toxin, pertussis toxin) and serve merely as a targeting agent. Alternatively, the effector can be a lymphocyte carrying a surface molecule that interacts, either directly or indirectly, with a tumor cell target. Various effector cells include cytotoxic T cells and NK cells.

In one aspect of immunotherapy, the tumor cell bear some marker that is amenable to targeting, i.e., is not present on the majority of other cells. Many tumor markers exist and any of these can be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, *Infect Immun.*, 66(11):5329-36 (1998); Christodoulides et al., *Microbiology*, 66(11):5329-36(1998)); cytokine therapy, e.g., interferons α, β, and γ, IL-1, GM-CSF, and TNF (Bukowski et al., *Clin Cancer Res.*, 4(10):2337-47 (1998); Davidson et al., *J Immunother.*, 21(5):389-98(1998); Hellstrand et al., *Acta Oncol.* 37(4): 347-53(1998)); gene therapy, e.g., TNF, IL-1, IL-2, and p53 (Qin et al., *Proc Natl Acad Sci USA*, 95(24):14411-6(1998); Austin-Ward and Villaseca, *Rev Med Chil*, 126(7):838-45 (1998); U.S. Pat. Nos. 5,830,880 and 5,846,945); and monoclonal antibodies, e.g., anti-PD1, anti-PDL1, anti-CD20, anti-ganglioside GM2, and anti-p185 (Topalian et al., *The New England journal of medicine*, 366:2443-2454 (2012); Brahmer et al., *The New England journal of medicine* 366:2455-2465 (2012); Hollander, *Front Immunol* (2012): 3:3. doi: 10.3389/fimmu.2012.00003; Hanibuchi et al., *Int J Cancer*, 78(4):480-5(1998); U.S. Pat. No. 5,824,311); all of which are hereby incorporated by reference in their entireties. It is contemplated that one or more anti-cancer therapies can be employed with the therapies described herein that involve the use anti-glycosylated BTLA antibodies or glycosylated BTLA polypeptides.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment can be accomplished by perfusion, direct injection, or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments can be of varying dosages as well.

Other Agents

It is contemplated that other agents can be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions can increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, can be used in combination with certain aspects of the present embodiments to improve the treatment efficacy.

7.6. Kits and Diagnostics

In various aspects, provided herein is a kit containing therapeutic agents and/or other therapeutic and delivery agents. In some embodiments, a kit is contemplated for preparing and/or administering a therapy provided herein. The kit can comprise one or more sealed vials containing any of the pharmaceutical compositions provided herein. The kit can include, for example, at least an anti-glycosylated BTLA antibody, or a glycosylated BTLA polypeptide, as well as reagents to prepare, formulate, and/or administer the components provided herein or perform one or more steps of the methods provided herein.

In some embodiments, the kit can include an anti-glycosylated BTLA antibody and at least one ancillary reagent. In some embodiments, the kit can include a glycosylated BTLA polypeptide and at least one ancillary reagent.

In some embodiments, the kit further includes a second anticancer agent. The second anticancer agent can be a chemotherapeutic agent, a immunotherapeutic agent, a hormonal therapeutic agent, or a cytokine.

In some embodiments, the kit can also include a suitable container means, which is a container that does not react with components of the kit, such as an eppendorf tube, an assay plate, a syringe, a bottle, or a tube. The container can be made from sterilizable materials, such as plastic or glass.

The kit can further include an instruction sheet that outlines the procedural steps of the methods set forth herein, and will follow substantially the same procedures as described herein or are known to those of ordinary skill. The instruction information can be in a computer readable media containing machine-readable instructions that, when executed using a computer, cause the display of a real or virtual procedure of delivering a pharmaceutically effective amount of the antibodies or polypeptides provided herein. The kit can also include a notice in the form prescribed by a governmental agency regulating the manufacture, use or sale of pharmaceuticals or biological products, which notice reflects approval by the agency of manufacture, use or sale for human administration.

8. EXAMPLES

It is understood that modifications which do not substantially change the nature and spirit of the various embodiments described herein are also contemplated. Accordingly, the following example is intended to illustrate but not in any way limiting.

Example 1—Production of Glycosylated BTLA-Binding Antibodies

A panel of monoclonal antibodies are produced against a recombinant glycosylated BTLA polypeptide using standard techniques (e.g., by injecting polypeptide comprising glycosylated epitopes as immunogens in rats (Aurrand-Lions et al., *Immunity*, 5, 391-405(1996))). Briefly, human glycosylated BTLA polypeptides coupled to 100 μg KLH carrier protein (keyhole limpet hemocyanin, Pierce) and mixed with adjuvant 56322 (Sigma), can be used to immunize female Wister rats. In total, three injections will be performed every 9 days. Two days after a final s.c. injection of human glycosylated BTLA polypeptides, blasts from draining lymph nodes are fused to Sp2/0 cells, and hybridomas will be selected. Growing clones are screened by ELISA for the production of monoclonal antibodies specifically recognizing human glycosylated BTLA. Positive clones will be subcloned, rescreened, and further tested. Antibodies are purified on protein G-Sepharose columns (GE HealthCare) according to the manufacturer instructions. The monoclonal antibodies are used to study in vivo tumor graft models. The VH and VL chains of the antibodies are sequenced and the complementarity determining regions (CDRs) determined by the IMGT numbering system (Lefranc et al., *Nuc. Acids Res.*, 27:209-212(1999)).

As indicated above, for certain purposes, including for example, use in the in vivo treatment of human disease, it is preferred to employ a humanized derivative of the mouse monoclonal antibody. To form such humanized antibodies, the framework sequences of the mouse monoclonal antibodies (the "Parental" sequences) are first aligned with framework sequences of a set of "Acceptor" human antibodies in order to identify differences in the framework sequences. Humanization are accomplished by substituting non-matching framework residues between the Parental and the Acceptor. Substitutions at potentially important positions such as those in the Vernier zone, the VH/VL inter-chain interface or CDR canonical class determining positions were analyzed for prospective back mutations (see, Foote, J. et al., *J. Molec. Biol.* 224:487-499 (1992)).

The Conserved Domain Database (COD) (Marchler-Bauer, et al. (2011) *Nucleic Acids Res.* 39:D225-D229) can be used to determine the domain content of each amino-acid chain and the approximate boundaries of each domain. Variable domain boundaries can be exactly determined along with the boundaries of the CDRs according to several commonly used definitions (Kabat, E. A. et al. (1991) "*Sequences of Proteins of Immunological Interest*," Fifth Edition. NIH Publication No. 91-3242; Chothia, C. et al., *J. Mol. Biol.* 196:901-917 (1987); Honegger, A. et al., *J. Molec. Biol.* 309(3):657-670 (2001))

Multiple alignments of the Parental sequence to the mouse and human germline sequences are generated using MAFFT (Katoh, K. et al., *Nucleic Acids Res.* 30: 3059-3066 (2002)) and entries in each alignment are ordered according to the sequence identity to the Parental sequence. Reference sets are reduced to a unique set of sequences by clustering at 100% sequence identity and excluding redundant entries.

The optimal Acceptor framework selection is based on the overall Parental antibodies sequence identity to the Acceptor across the framework of both chains; however the positions that compose the VH/VL inter-chain interface are of particular interest. Additionally, the CDR-loops lengths and CDR positions responsible for the discrete set of canonical structures that has been defined for 5 of the CDRs (Chothia, C. et al., *J. Mol. Biol.* 196:901-917 (1987); Martin, A. C. et al., *J. Molec. Biol* 263:800-815 (1996); Al-Laziniki, B. et al., *J. Molec. Biol.* 273:927-948(1997)) are compared to the germlines, in order to determine which germline frameworks have both the same interface residues and are known to support similar CDR-loop conformations.

Based on the parent antibody's sequence alignment to the human germlines the closest matching entries are identified. The choice of the preferred human germline is based on the ordered criteria: (1) Sequence identity across the framework; (2) Identical or compatible inter-chain interface residues; (3) Support loops with the Parental CDRs canonical conformations; (4) The combination of heavy and light germlines are found in expressed antibodies; and (5) Presence of N-glycosylation sites that have to be removed.

A structural model of Fv-region of the humanized antibody is generated. Candidate structural template fragments for the FR and CDRs as well as the full Fv are scored, ranked and selected from an antibody database based on their sequence identity to the target, as well as qualitative crystallographic measures of the template structure such as the resolution, in Angstroms (Å).

In order to structurally align the CDRs to the FR templates, 5 residues on either side of the CDR are included in the CDR template. An alignment of the fragments is generated based on overlapping segments and a structural sequence alignment generated. The template fragments along with the alignment were processed by MODELLER (SalI, A. et al.; *J. Molec. Biol.* 234:779-815(1993)). This protocol creates conformational restraints derived from the set of aligned structural templates. An ensemble of structures which satisfied the constraints are created by conjugate gradient and simulated annealing optimization procedures. Model structures are selected from this ensemble on the basis of an energy score, derived from the score of the proteins structure and the satisfaction of the conformational constraints. The models are inspected and the side chains of the positions which differed between the target and template are optimized using a side chain optimization algorithm and energy minimized. A suite of visualization and computational tools are used to assess the CDRs conformational variability, local packing and surface analysis to select one or more preferred models.

A structural model of the Parental antibody is constructed and inspected for imperfections such as poor atomic packing, strain in bond lengths, bond angles or dihedral angles. These imperfections may indicate potential issues with the structural stability of the antibody. The modeling protocol seeks to minimize such imperfections. The initial structural model of the Humanized Fv contains all safe substitutions (i.e., substitutions that should not affect binding affinity or stability) and cautious substitutions (i.e., the position substitution is made but the position may be important for binding affinity). Substitutions at positions that are considered to be associated with a risk a decreased binding affinity or reduced stability are not altered. The template search and selection is performed separately to the Parental template search in order to create a good stand-alone model rather than a closely matching variant model of the Parental. As the assessment of potential substitutions is performed the model is updated to reflect the preferred substitutions and the effect of back mutations.

Mouse monoclonal antibodies (mAbs) were raised against human glycosylated BTLA polypeptides essentially as described above. In brief, antibody-producing hybridomas against BTLA were obtained by the fusion of SP2/0 murine myeloma cells with spleen cells isolated from BALB/c mice that were immunized with human glycosylated BTLA polypeptides coupled to 100 μg KLH carrier protein according to standardized protocol. Before fusion, sera from immunized mice were validated for binding to immunogen using FACS. T293 cells overexpressing BTLA WT (fully glycosylated) were tagged with biotin and then mixed T293 cells overexpressing fully unglycosylated BTLA. Mixed cells were incubated with primary antibodies against BTLA and were further washed with secondary antibodies conjugated with FITC. After washing, fluorescence intensity (MFI) was measured to assess relative binding of antibodies to membrane bound glycosylated or unglycosylated BTLA. Antibodies that exhibited significantly higher MFI on glycosylated BTLA over unglycosylated BTLA were identified as "glyco-specific" antibodies. Several monoclonal antibody-producing hybridomas were produced, including 36 hybridomas producing mouse mAbs designated as STC601 to STC636.

Example 2—Isotyping of Glycosylated BTLA-Binding Antibodies

The isotypes of STC601 to STC636 mAbs were determined by ELISA testing of hybridoma supernatants, using Sigma-Aldrich ISO2 SIGMA Mouse Monoclonal Antibody Isotyping Reagents.

In short, 100 μL hybridoma supernatant (1:20) or purified antibody (1 μg/mL) was adsorbed for 1 h at 37° C. in a white Nunc Maxisorp 96 well plate followed by washing and blocking with 1% BSA in PBS for 30' at 21° C., washing, and addition of 100 μl of isotyping solution diluted 1:1000 in PBS (Sigma Aldrich, St. Louis, Mo., US) for 30' at 21° C., 1:5000 Anti-goat IgG-HRP 15' at 21° C., development with BioRad Clarity Western ECL substrate (BioRad, Hercules, Calif., US) and Victor X3 (PerkinElmer, Hopkinton, Mass., US).

Table 9 shows the results of the isotype determination. STC601-STC636 mAbs were found to include IgG1, IgG2A, IgG2B, and IgG3/M isotypes.

TABLE 9

Isotypes of anti-BTLA mAbs STC601-STC636

| Anti-BTLA mAb | Isotype |
| --- | --- |
| STC601 | G2a |
| STC602 | G1/2a |
| STC603 | G2a |
| STC604 | G1 |
| STC605 | G1 |
| STC606 | G1 |
| STC607 | G2a |
| STC608 | G1 |

TABLE 9-continued

Isotypes of anti-BTLA mAbs STC601-STC636

| Anti-BTLA mAb | Isotype |
|---|---|
| STC609 | G2a |
| STC610 | G1 |
| STC611 | G1 |
| STC612 | G3/M |
| STC613 | G1 |
| STC614 | G1 |
| STC615 | G1 |
| STC616 | G2b |
| STC617 | G1 |
| STC618 | G1 |
| STC619 | G2b |
| STC620 | G1 |
| STC621 | G1 |
| STC622 | G1 |
| STC623 | G1 |
| STC624 | G1 |
| STC625 | G1 |
| STC626 | G2B |
| STC627 | G1 |
| STC628 | G1 |
| STC629 | G1 |
| STC630 | G1 |
| STC631 | G1 |
| STC632 | G1 |
| STC633 | G1 |
| STC634 | M |
| STC635 | G1 |
| STC636 | G1 |

Example 3—FACS Analysis of Glycosylated BTLA-Binding Antibodies

The ability of anti-BTLA mAbs STC601-STC636 to bind cell-surface expressed BTLA was analyzed by fluorescence activated cell sorting (FACS).

Briefly, BTLA was recombinantly overexpressed in 293T cells and binding of STC601-STC636 to BTLA-293T cells and to 293T vector controls, was analyzed by FACS.

Cell Culture, Stable Transfectants, and Transfection.

All cells were obtained from American Type Culture Collection (ATCC, Manassas, Va., US). These cells were grown in in DMEM/F12 or RPMI 1640 medium supplemented with 10% fetal bovine serum (FBS). BTLA-stable transfectants 293T cells were selected using 10 µg/mL puromycin (InvivoGen, San Diego, Calif., US). For transient transfection, cells were transfected with plasmid DNA encoding BTLA, using SN liposomes (Hu, M. C. et al., 2004, *Cell*, 117:225-237), Lipofectamine 2000, Lipofectamine LTX (Life Technologies, Carlsbad, Calif., US), or PEI.

Flow Cytometry. Cells overexpressing BTLA or empty vector were isolated by trypsinization and collected in Cell Staining Buffer (CSB) (BioLegend, San Diego, Calif., US) at 2×10^6 cells/mL. 50 µL of cells were aliquoted to a 96 well round-bottom plate, to which 50 µL of 20 µg/mL primary antibody was added, followed by gentle mixing and 1 h incubation at 4° C. in the dark. Cells were washed with CSB, incubated with anti-mouse IgG-PE conjugate (10 µg/mL) with DAPI (1:100) 30' 21° C. in the dark. Cells were washed and data acquired using Guava EasyCyte HT (Millipore Darmstadt, DE) or FACS Celesta (Becton Dickinson, Franklin Lakes, N.J., US) flow cytometer.

Table 10 shows exemplary FACS analysis results illustrating anti-BTLA mAb binding to cell-surface expressed BTLA. STC601-STC636 anti-BTLA mAbs were all found to bind cell-surface expressed BTLA, as indicated by stronger binding FACS signals (increased % Gate, increased MR) observed with BTLA expressing 293T cells relative to 293T *empty* vector controls.

TABLE 10

FACS Analysis of anti-BTLA mAbs STC601-STC636

| STC | 293T-BTLA | | 293T | |
|---|---|---|---|---|
| | % Gate | MR | % Gate | MR |
| STC601 | 80.8 | 729 | 8.36 | 12.9 |
| STC602 | 73.5 | 564 | 4.11 | 12.2 |
| STC603 | 78.6 | 928 | 6.45 | 12.6 |
| STC604 | 78.9 | 960 | 5.39 | 12 |
| STC605 | 82.1 | 1195 | 3.68 | 10.9 |
| STC606 | 81.6 | 1123 | 4.02 | 11.5 |
| STC607 | 77.9 | 607 | 5.64 | 12.8 |
| STC608 | 83.2 | 1471 | 3.91 | 11 |
| STC609 | 85.6 | 1240 | 6.07 | 12.1 |
| STC610 | 84.6 | 1368 | 4.5 | 11.2 |
| STC611 | 85.6 | 1243 | 5.62 | 12.2 |
| STC612 | 66.6 | 203 | 3.23 | 10.9 |
| STC613 | 82.4 | 1561 | 5.42 | 12.8 |
| STC614 | 80.8 | 1297 | 4.44 | 11.6 |
| STC615 | 71.3 | 320 | 5.47 | 11.5 |
| STC616 | 86 | 933 | 4.02 | 11.2 |
| STC617 | 83 | 1275 | 4.66 | 10.4 |
| STC618 | 82.9 | 1679 | 5.2 | 11.5 |
| STC619 | 76 | 530 | 5.36 | 11.7 |
| STC620 | 73.5 | 880 | 3.62 | 10.6 |
| STC621 | 78.2 | 1095 | 6.28 | 11.9 |
| STC622 | 80.9 | 1300 | 6.91 | 12.5 |
| STC623 | 82.9 | 1162 | 6.39 | 12.3 |
| STC624 | 82.4 | 1195 | 4.06 | 10.4 |
| STC625 | 72.2 | 336 | 4.94 | 11.4 |
| STC626 | 86.2 | 3448 | 5.73 | 12 |
| STC627 | 83 | 1722 | 6.78 | 11.3 |
| STC628 | 82.1 | 1610 | 9.24 | 12.4 |
| STC629 | 79 | 1098 | 7.88 | 12.1 |
| STC630 | 82.5 | 1496 | 6.12 | 11.5 |
| STC631 | 82.4 | 1522 | 5.7 | 11.7 |
| STC632 | 77.7 | 936 | 5.08 | 11 |
| STC633 | 81.9 | 1623 | 7.26 | 12 |
| STC634 | 74.6 | 360 | 7.77 | 11.3 |
| STC635 | 82.4 | 1470 | 5.75 | 11.2 |
| STC636 | 81 | 1439 | 7.67 | 12.4 |
| BTLA (MIH26) | 91.3 | 2848 | 16.6 | 17.6 |
| Unstain | 2.06 | 8.33 | 3.09 | 7.21 |
| Isotype | 5.08 | 11.7 | 11.6 | 15.9 |
| 2'Ab only | 10.1 | 16.6 | 15.3 | 18.1 |

Example 4—Glyco-Specificity of Glycosylated BTLA-Binding Antibodies

The glyco-specificity of anti-BTLA mAbs was analyzed by dot-blot and western blot analyses.

Dot Blot

Glyco-specific binding of STC601-STC636 anti-BTLA mAbs to glycosylated BTLA and deglycosylated (N-glycosidase F (PGNaseF) treated) BTLA was tested in a dot blot assay.

In short, 0.5 µg/well (5 µg/ml; 100 µl per well) of glycosylated BTLA or deglycosylated BTLA were immobilized on a nitrocellulose membrane in a 96-well dot blot apparatus (Bio-Dot BioRad, Hercules, Calif., US). The membrane was blocked and then incubated with hybridoma supernatant (5 µg/mL; 100 µl per well) or purified mouse monoclonal antibodies (1 µg/mL; 100 µl per well) for 12 h at 4° C. Antibody-binding to immobilized BTLA on the nitrocellulose membrane was detected via secondary antibodies (e.g., 1:5,000—1:20,000 anti-mouse-HRP secondary; Jackson Labs, Bar Harbor, Me., US) and imaging (e.g., SuperSignal West Femto, ThermoFisher Waltham, Mass., US or Chemdoc imager, BioRad, Hercules, Calif., US).

FIGS. 1A and 1B show results of an exemplary dot blot assay of anti-BTLA mAbs STC601-STC636. Each anti-BTLA mAb (0.5 µg/well loaded) was tested for binding to glycosylated BTLA (PNGaseF "−") or deglycosylated BTLA (PNGaseF "+"). Non-specific antibody controls ("IgG," 0.25 µg/well loaded) and a commercially available BTLA reference antibody (BioLegend, San Diego, Calif., US, "BioLegend," 5 µg/well loaded) were also included in the assay. FIG. 1A shows the experimental layout of test antibodies and controls. FIG. 1B depicts the result of an experimental dot blot assay obtained with STC601-STC636 mAbs and controls. Several monoclonal antibodies, including STC602, STC604, STC605, STC606, STC607, STC608, STC609, STC610, STC611, STC612, STC613, STC614, STC616, STC617, STC618, STC619, STC620, STC621, STC622, STC623, STC624, STC626, STC627, STC628, STC629, STC630, STC631, STC632, STC634, STC635 and STC636, showed glycol-specific binding to glycosylated BTLA.

Western Blot

The glycol-specificity of anti-BTLA mAbs was further analyzed by immunoprecipitation/Western blot analysis.

Immunoblot Analysis.

Immunoblot analysis was performed as described previously (Lim et al., 2008, Gastroenterology, 135:21 28-40; and Lee et al., 2007, *Cell*, 130:440-455). Image acquisition and quantitation of band intensity were performed using a Chemdoc Imager (BioRad, Hercules, Calif., US). The secondary antibodies were anti-mouse or-rabbit Alexa Fluor 488 or 594, and nuclei were stained with 4',6-diamidino-2-phenylindole (DAPI) (Life Technologies, Carlsbad, Calif., US).

FIG. 2 shows exemplary Western blot analysis results for anti-BTLA mAbs STC604, STC605, STC606, STC608, STC610, STC613, STC618, STC622, STC626, STC627, STC628, STC630, STC635, and STC636. In the Western blot assays, anti-BTLA mAbs were tested for their ability to recognize fully glycosylated wild-type BTLA and to recognize certain BTLA mutants lacking two (N75/2NQ, N94/2NQ, N110/2NQ) or all three (3NQ) of BTLA's N-glycosylation sites. All tested antibodies were found to recognize glycosylated wild-type BTLA (WT). In addition, all tested anti-BTLA mAbs were found to recognize one or more BTLA double mutants that retained only a single glycosylation site at BLTA N75, N94, or N110. Generally, the band intensities shown in the Western blots of FIG. 2 indicate the specific glycosylation motif recognized by each of the tested antibodies and the binding strength of the tested antibodies to the recognized glycosylation motifs. By contrast, all tested anti-BTLA mAbs were found to show only background binding, if any, to a BTLA triple mutant, that retained none of BTLA's N75, N94, or N110 glycosylation sites.

Example 5—Binding Affinities and Binning of Glycosylated BTLA-Binding Antibodies Anti-BTLA mAbs, including STC601-STC636 were characterized with respect to their respective binding affinities for BTLA and further evaluated in competition binding assays and epitope binning experiments.

KD Determination and Binning.

Antibody/BTLA complex in 20 nM solution was loaded onto ForteBio's APC sensors and baseline was established in PBS with 1 mg/mL BSA (assay buffer). Association was performed by submersion of sensors in anti-BTLA antibodies in assay buffer. Dissociation was performed in fresh assay buffer. All experiments were performed with sensor shaking at 1,000 rpm. Data analysis software from ForteBio was used to fit the data to a 1:1 binding model to project association and dissociation rates. The kD was calculated using the ratio kd/ka. In a typical epitope binning assay, 10 nM BTLA-His was preincubated with αHis antibody (10 nM) for 1 h at 21° C. Control antibody (20 nM) was loaded onto AMC sensors (ForteBio, Menlo Park, Calif., US) and remaining Fc-binding sites on the sensor were blocked with whole mouse IgG antibody (Jackson, Bar Harbor, Me., US). The sensors were exposed to preincubated antigen/secondary antibody mixture. Raw data was processed using Data Analysis Software 7.0 (ForteBio, Menlo Park, Calif., US) and the antibody pairs were assessed for competitive binding. Additional binding by the second antibody indicates an unoccupied epitope (non-competitor), while no binding indicates epitope blocking (competitor). SPR Biacore X-100 was also used for kD determination. Protein A chip or mouse IgG capture antibody immobilized CM5 chip (BIAcore, ilina, SK) was coated with antibody with 600 response units (RU) and the BTLA ECD was injected in the microfluidic channel. The kD values were obtained using the fitting tool of the BIAevaluation software (BIAcore, ilina, SK).

Table 11 summarizes kinetic binding constants ($k_a$ and $k_d$ rates) and binding affinities ($K_D$ values) of anti-BTLA mAbs STC604, STC610, STC613, STC618, STC622, STC626, and STC635 for BTLA. FIGS. 3A-C illustrate the results of exemplary SPR (BIAcore™) experiments to determine the kinetic binding constants and binding affinities of anti-BTLA mAbs STC613, STC626, and STC635 for BTLA.

TABLE 11

Binding affinities of anti-BTLA mAbs for BTLA.

| Anti-BTLA mAb | BIAcore Kinetic Mode | | |
|---|---|---|---|
| | $k_a$ (1/Ms) | $k_d$ (1/s) | KD (M) |
| STC604 | 1.03E+06 | 9.60E−04 | 9.37E−10 |
| STC610 | 9.23E+05 | 4.95E−04 | 5.36E−10 |
| STC613 | 1.51E+06 | 3.85E−04 | 2.56E−10 |
| STC618 | 5.85E+05 | 5.01E−04 | 8.57E−10 |
| STC622 | 5.34E+05 | 3.72E−04 | 6.97E−10 |
| STC626 | 1.86E+05 | 4.12E−04 | 2.21E−09 |
| STC635 | 4.95E+05 | 2.78E−03 | 5.61E−09 |

FIG. 4A and Table 12 illustrate results of exemplary competition assays and binning experiments with STC613. FIG. 4B and Table 13 illustrate results of exemplary competition assays and binning experiments with STC636. Table 14 provides a summary of binning results. STC613 and STC636 were found not to compete with each other for BTLA binding. STC605, STC608, STC626, STC627, STC628, STC630, STC631, and STC636 were found to compete with STC636 for BTLA binding, but not with STC613. STC604, STC606, STC610, STC613, STC618, STC622, and STC635 were found to compete with STC613 for BTLA binding, but not with STC636.

TABLE 12

Binning of anti-BTLA mAbs with STM613

| Anti-BTLA mAb | Loading Sample ID | Response | Pair/Block |
|---|---|---|---|
| STC604 | STC613 | 0.0861 | Block |
| STC605 | STC613 | 0.2983 | Pair |
| STC606 | STC613 | 0.0771 | Block |

TABLE 12-continued

Binning of anti-BTLA mAbs with STM613

| Anti-BTLA mAb | Loading Sample ID | Response | Pair/Block |
|---|---|---|---|
| STC608 | STC613 | 0.342 | Pair |
| STC610 | STC613 | 0.0899 | Block |
| STC613 | STC613 | 0.079 | Block |
| STC618 | STC613 | 0.0593 | Block |
| STC622 | STC613 | 0.0598 | Block |
| STC626 | STC613 | 0.2681 | Pair |
| STC627 | STC613 | 0.4649 | Pair |
| STC628 | STC613 | 0.4684 | Pair |
| STC630 | STC613 | 0.4627 | Pair |
| STC631 | STC613 | 0.4701 | Pair |
| STC635 | STC613 | 0.0846 | Block |
| STC636 | STC613 | 0.4917 | Pair |

TABLE 13

Binning of anti-BTLA mAbs with STM636

| Anti-BTLA mAb | Loading Sample ID | Response | Pair/Block |
|---|---|---|---|
| STC605 | STC636 | 0.0033 | Block |
| STC608 | STC636 | 0.0129 | Block |
| STC613 | STC636 | 0.4355 | Pair |
| STC626 | STC636 | −0.02 | Block |
| STC627 | STC636 | 0.0305 | Block |
| STC628 | STC636 | 0.0347 | Block |
| STC630 | STC636 | 0.0346 | Block |
| STC631 | STC636 | 0.0216 | Block |

TABLE 14

Summary of Binning Results

| Group | STC613 | STC636 |
|---|---|---|
| Family | STC604 | STC605 |
|  | STC606 | STC608 |
|  | STC610 | STC626 |
|  | STC613 | STC627 |
|  | STC618 | STC628 |
|  | STC622 | STC630 |
|  | STC635 | STC631 |
|  |  | STC636 |

Example 6—Neutralizing Activity of Glycosylated BTLA-Binding Antibodies

Anti-BLTA mAbs were evaluated with respect to their ability to inhibit the BTLA-HVEM protein interaction using an ELISA assay.

Inhibition of BTLA and HMV interaction by ELISA.

Antibody neutralizing activity was assessed by BTLA:HVEM Inhibitor Screening Assay kit (Cat. #72008, BPS Bioscience, San Diego, Calif., US) was used according to the manufacturer's instructions. BTLA was coated onto a 96-well plate followed first with 0.5 or 5 µg/mL antibody, then biotinylated HVEM was added to the reaction, followed by streptavidin-HRP. Chemiluminescence was measured after addition of HRP substrate.

Table 15 provides exemplary ELISA results illustrating the ability of anti-BTLA mAbs to inhibit the BTLA-HVEM protein interaction, expressed as percent inhibition relative to a control reflecting the signal of an uninhibited BTLA-HVEM interaction. For example, at a concentration of 5 µg/ml, STC613 was found to inhibit 99.0% of the BTLA-HVEM interaction, STC626 was found to inhibit 96.8% of the BTLA-HVEM interaction, and STC635 was found to inhibit 97.3% of the BTLA-HVEM interaction. FIG. 5 and FIG. 6 illustrate exemplary results of an BTLA-HVEM competition ELISA. STC613 was found to inhibit the BTLA-HVEM interaction with an $IC_{50}$ of 1.088 µg/ml. STC 626 was found to inhibit the BTLA-HVEM interaction with an $IC_{50}$ of 0.416 µg/ml.

TABLE 15

Inhibition of BTLA:HVEM interaction by anti-BTLA mAbs

| | Inhibition of BTLA:HVEM (%) | |
|---|---|---|
| Anti-BTLA mAb | 5 µg/ml mAb | 0.5 µg/ml mAb |
| STC601 | 58.7 | 12.3 |
| STC602 | 70.8 | 9.3 |
| STC603 | 59.3 | 6.3 |
| STC604 | 98.9 | 16.3 |
| STC605 | 75.0 | 17.4 |
| STC606 | 98.6 | 14.2 |
| STC607 | 56.1 | 8.8 |
| STC608 | 62.4 | 8.0 |
| STC609 | 26.4 | 29.7 |
| STC610 | 96.7 | 24.3 |
| STC611 | 25.9 | 12.3 |
| STC612 | 15.8 | 9.2 |
| STC613 | 99.0 | 26.1 |
| STC614 | 97.8 | 21.5 |
| STC615 | 17.9 | 1.6 |
| STC616 | 18.6 | 1.8 |
| STC617 | 46.6 | 10.2 |
| STC618 | 99.0 | 30.7 |
| STC619 | 23.6 | 14.6 |
| STC620 | 32.8 | 6.7 |
| STC621 | 98.3 | 23.7 |
| STC622 | 98.3 | 22.1 |
| STC623 | 40.8 | 12.7 |
| STC624 | 97.7 | 18.1 |
| STC625 | 12.5 | 10.5 |
| STC626 | 96.8 | 45.6 |
| STC627 | 11.5 | −1.6 |
| STC628 | −1.0 | −2.2 |
| STC629 | 0.4 | −0.7 |
| STC630 | 1.3 | −4.0 |
| STC631 | −0.6 | −0.1 |
| STC632 | 87.5 | 21.7 |
| STC633 | 18.8 | 3.4 |
| STC634 | 16.9 | −1.0 |
| STC635 | 97.3 | 21.8 |
| STC636 | −0.1 | 4.8 |

Example 7—Epitope Mapping of STC613

Epitope mapping of the anti-BTLA mAb STC613 was performed using chemical cross-linking, High-Mass MALDI mass spectrometry and nLC-Orbitrap mass spectrometry (CovalX AG, Zurich, Switzerland).

The BTLA antigen used for STC613 epitope mapping had the following amino acid sequence:

```
                                              (SEQ ID NO: 86)
KESCDVQLYI KRQSEHSILA GDPFELECPV KYCANRPHVT

WCKLNGTTCV KLEDRQTSWK EEKNISFFIL HFEPVLPNDN

GSYRCSANFQ SNLIESHSTT LYVTGKQNEL SDTAGREINL

VDHHHHHH
```

Tables 16-20 provide the sequences of individual peptides identified following Asp-N, trypsin, chymotrypsin, elastase and thermolysin proteolysis. In combination the BTLA peptides identified in all five proteolysis samples cover 100% of the BTLA amino acid sequence SEQ ID NO: 86.

Table 16 provides 34 BTLA peptides that were identified following trypsin proteolysis, covering 84.3% of the BTLA amino acid sequence of SEQ ID NO: 86.

TABLE 16

BTLA peptides identified following trypsin proteolysis

| Sequence | Modifications | Position Peptide 1* | Position Peptide 2 |
|---|---|---|---|
| kESCDVQLYIK (SEQ ID NO: 87) | K1(GlyGly) | 1-11 | |
| KESCDVQLYIK-K11-156 (SEQ ID NO: 88) | monolink | 1-11 | |
| kESCDVQLYIKR (SEQ ID NO: 89) | K1(GlyGly) | 1-12 | |
| KESCDVQLYIKR-K11-156 (SEQ ID NO: 90) | monolink | 1-12 | |
| KESCDVQLYIKR-K1-53 (SEQ ID NO: 90) | intralink | 1-12 | |
| KESCDVQLYIKR-Y9-K11 (SEQ ID NO: 90) | intralink | 1-12 | |
| ESCDVQLYIKR-K10-155 (SEQ ID NO: 91) | monolink | 2-12 | |
| ESCDVQLYIKR-K10-156 (SEQ ID NO: 91) | monolink | 2-12 | |
| RQSEHSILAGDPFELECPVKYCANRPHVTWCK-H27-156 (SEQ ID NO: 92) | monolink | 11-43 | |
| RQSEHSILAGDPFELECPVKYCANRPHVTWCK-K20-155 (SEQ ID NO: 92) | monolink | 11-43 | |
| RQSEHSILAGDPFELECPVKYCANRPHVTWCK-K20-156 (SEQ ID NO: 92) | monolink | 11-43 | |
| RQSEHSILAGDPFELECPVk (SEQ ID NO: 93) | K20(GlyGly) | 12-31 | |
| RQSEHSILAGDPFELECPVK (SEQ ID NO: 94) | monolink | 12-31 | |
| RQSEHSILAGDPFELECPVK-R1-156 (SEQ ID NO: 94) | monolink | 12-31 | |
| QSEHSILAGDPFELECPVk (SEQ ID NO: 95) | K19(GlyGly) | 13-31 | |
| QSEHSILAGDPFELECPVK-H4-156 (SEQ ID NO: 96) | monolink | 13-31 | |
| QSEHSILAGDPFELECPVK-S2-155 (SEQ ID NO: 96) | monolink | 13-31 | |
| QSEHSILAGDPFELECPVK-S2-156 (SEQ ID NO: 96) | monolink | 13-31 | |
| QSEHSILAGDPFELECPVKYCANRPHVTWCK-K19-156 (SEQ ID NO: 97) | monolink | 13-43 | |
| QSEHSILAGDPFELECPVKYCANRPHVTWCK-K19-K31 (SEQ ID NO: 97) | intralink | 13-43 | |
| YCANRPHVTWCK-T9-155 (SEQ ID NO: 98) | monolink | 32-43 | |
| YCANRPHVTWCK-T9-156 (SEQ ID NO: 98) | monolink | 32-43 | |
| YCANRPHVTWCK-Y1-156 (SEQ ID NO: 98) | monolink | 32-43 | |
| NISFFILHFEPVLPNDNGSYR (SEQ ID NO: 99) | | 64-84 | |
| CSANFQSNLIESHSTTLYVTGK-S12-156 (SEQ ID NO: 100) | monolink | 85-106 | |
| CSANFQSNLIESHSTTLYVTGK-S14-156 (SEQ ID NO: 100) | monolink | 85-106 | |
| CSANFQSNLIESHSTTLYVTGK-S2-156 (SEQ ID NO: 100) | monolink | 85-106 | |
| CSANFQSNLIESHSTTLYVTGK-S7-156 (SEQ ID NO: 100) | monolink | 85-106 | |
| CSANFQSNLIESHSTTLYVTGK-S7-K22 (SEQ ID NO: 100) | intralink | 85-106 | |
| CSANFQSNLIESHSTTLYVTGK-S7-T16 (SEQ ID NO: 100) | intralink | 85-106 | |

TABLE 16-continued

BTLA peptides identified following trypsin proteolysis

| Sequence | Modifications | Position Peptide 1* | Position Peptide 2 |
|---|---|---|---|
| CSANFQSNLIESHSTTLYVTGK-S7-Y18 (SEQ ID NO: 100) | intralink | 85-106 | |
| CSANFQSNLIESHSTTLYVTGK-T15-156 (SEQ ID NO: 100) | monolink | 85-106 | |
| QNELSDTAGR (SEQ ID NO: 101) | | 107-116 | |
| EINLVDHHHHHH (SEQ ID NO: 102) | | 117-128 | |

*Peptide positions are indicated relative to the BTLA amino acid sequence of SEQ ID NO: 86.

Table 17 provides 75 BTLA peptides identified following chymotrypsin proteolysis, covering 96.88% of the BTLA amino acid sequence of SEQ ID NO: 86.

TABLE 17

BTLA peptides identified following chymotrypsin proteolysis

| Sequence | Modifications | Position Peptide 1* | Position Peptide 2 |
|---|---|---|---|
| KEScDVQL (SEQ ID NO: 103) | C4(Carbamidomethyl) | 1-8 | |
| KESCDVQL (SEQ ID NO: 104)-KESCDVQL (SEQ ID NO: 104)-a1-b1 | intra-protein xl | 1-8 | 1-9 |
| KEScDVQLY (SEQ ID NO: 105) | C4(Carbamidomethyl) | 1-9 | |
| IKRQSEHSIL-H7-155 (SEQ ID NO: 106) | monolink | 10-19 | |
| IKRQSEHSIL-K2-58 (SEQ ID NO: 105) | intralink | 10-19 | |
| IKRQSEHSILAGDPF (SEQ ID NO: 107) | | 10-24 | |
| IKRQSEHSILAGDPF (SEQ ID NO: 107)-ELECPVKY (SEQ ID NO: 108)-a8-b7 | intra-protein xl | 10-24 | 25-32 |
| IKRQSEHSILAGDPF-H7-156 (SEQ ID NO: 107) | monolink | 10-24 | |
| IKRQSEHSILAGDPF-K2-156 (SEQ ID NO: 107) | monolink | 10-24 | |
| IKRQSEHSILAGDPF-S5-155 (SEQ ID NO: 107) | monolink | 10-24 | |
| IKRQSEHSILAGDPFEL (SEQ ID NO: 109) | | 10-26 | |
| AGDPFELEcPVKY (SEQ ID NO: 110) | C9(Carbamidomethyl) | 20-32 | |
| CANRPHVTW (SEQ ID NO: 111)-ELECPVKY (SEQ ID NO: 108)-a4-b7 | intra-protein xl | 33-41 | 25-32 |
| CANRPHVTW (SEQ ID NO: 111)-KESCDVQLY (SEQ ID NO: 112)-a8-b1 | intra-protein xl | 33-41 | 1-9 |
| CANRPHVTW-R4-156 (SEQ ID NO: 111) | monolink | 33-41 | |
| CANRPHVTW-T8-155 (SEQ ID NO: 111) | monolink | 33-41 | |
| CANRPHVTW-T8-156 (SEQ ID NO: 111) | monolink | 33-41 | |
| cKLnGTTcVKLEDRQTSW (SEQ ID NO: 113) | C1(Carbamidomethyl); N4(Deamidated); C8(Carbamidomethyl) | 42-59 | |
| cKLNGTTcVKLEDRQTSW (SEQ ID NO: 114) | C1(Carbamidomethyl); C8(Carbamidomethyl) | 42-59 | |

TABLE 17-continued

BTLA peptides identified following chymotrypsin proteolysis

| Sequence | Modifications | Position Peptide 1* | Position Peptide 2 |
|---|---|---|---|
| NGTTCVKLEDRQTSW (SEQ ID NO: 115)-IESHSTTLY (SEQ ID NO: 116)-a13-b3 | intra-protein xl | 45-59 | 94-102 |
| KEEKNISFF (SEQ ID NO: 117)-KESCDVQLY (SEQ ID NO: 118)-a1-b1 | intra-protein xl | 60-68 | 1-9 |
| EPVLPNDNGSYRCSANF (SEQ ID NO: 119)-R12-155 | monolink | 73-89 | |
| EPVLPNDNGSYRCSANF (SEQ ID NO: 111)-VTGKQNEL (SEQ ID NO: 120)-a10-b4 | intra-protein xl | 73-89 | 103-110 |
| RCSANFQSNL (SEQ ID NO: 121)-NGTTCVKL (SEQ ID NO: 122)-a3-b7 | intra-protein xl | 84-93 | 45-52 |
| RCSANFQSNL (SEQ ID NO: 121)-NGTTCVKL (SEQ ID NO: 122)-a8-b7 | intra-protein xl | 84-93 | 45-52 |
| QSNLIESHSTTL (SEQ ID NO: 123) | | 90-101 | |
| QSNLIESHSTTL (SEQ ID NO: 123)-KEEKNISF (SEQ ID NO: 124)-a11-b4 | intra-protein xl | 90-101 | 60-67 |
| QSNLIESHSTTLY (SEQ ID NO: 125) | | 90-102 | |
| IESHSTTLY (SEQ ID NO: 126)-ELECPVKY (SEQ ID NO: 127)-a4-b7 | intra-protein xl | 94-102 | 25-32 |
| VTGKQNELSDTAGREINL (SEQ ID NO: 128) | | 103-120 | |
| VTGKQNELSDTAGREINL (SEQ ID NO: 128)-CANRPHVTW (SEQ ID NO: 129)-a11-b8 | intra-protein xl | 103-120 | 33-41 |
| VTGKQNELSDTAGREINL (SEQ ID NO: 128)-ECPVKY (SEQ ID NO: 130)-a9-b5 | intra-protein xl | 103-120 | 27-32 |
| VTGKQNELSDTAGREINL (SEQ ID NO: 128)-ELECPVKY (SEQ ID NO: 131)-a11-b7 | intra-protein xl | 103-120 | 25-32 |
| VTGKQNELSDTAGREINL (SEQ ID NO: 128)-VDHHHHHH (SEQ ID NO: 132)-a9-b3 | intra-protein xl | 103-120 | 121-128 |
| VTGKQNELSDTAGREINLVDHHHHHH (SEQ ID NO: 133) | | 103-128 | |
| VTGKQNELSDTAGREInLVDHHHHHH (SEQ ID NO: 133) | N17(Deamidated) | 103-128 | |
| SDTAGREINL (SEQ ID NO: 135)-ECPVKY (SEQ ID NO: 130)-a3-b5 | intra-protein xl | 111-119 | 27-32 |
| SDTAGREINL (SEQ ID NO: 135)-KESCDVQLY (SEQ ID NO: 136)-a3-b3 | intra-protein xl | 111-119 | 1-9 |
| SDTAGREINLVDHHHHHH (SEQ ID NO: 137) | | 111-128 | |
| SDTAGREINLVDHHHHHH (SEQ ID NO: 137)-EDRQTSW (SEQ ID NO: 138)-a17-b6 | intra-protein xl | 111-128 | 53-59 |
| SDTAGREINLVDHHHHHH-S1-155 (SEQ ID NO: 137) | monolink | 111-128 | |
| SDTAGREINLVDHHHHHH-S1-156 (SEQ ID NO: 137) | monolink | 111-128 | |

TABLE 17-continued

BTLA peptides identified following chymotrypsin proteolysis

| Sequence | Modifications | Position Peptide 1* | Position Peptide 2 |
|---|---|---|---|
| SDTAGREINLVDHHHHHH (SEQ ID NO: 137)-VTGKQNEL (SEQ ID NO: 139)-a1-b2 | intra-protein xl | 111-128 | 103-110 |
| SDTAGREINLVDHHHHHH (SEQ ID NO: 137)-VTGKQNEL-a1-b4 | intra-protein xl | 111-128 | 103-110 |
| SDTAGREINLVDHHHHHH (SEQ ID NO: 137)-VTGKQNEL (SEQ ID NO: 140)-a3-b4 | intra-protein xl | 111-128 | 103-110 |
| SDTAGREINLVDHHHHHH (SEQ ID NO: 137)-VTGKQNEL (SEQ ID NO: 140)-a6-b4 | intra-protein xl | 111-128 | 103-110 |
| SDTAGREINLVDHHHHHH (SEQ ID NO: 137)-YVTGKQNEL (SEQ ID NO: 140)-a17-b5 | intra-protein xl | 111-128 | 102-110 |
| SDTAGREINLVDHHHHHH (SEQ ID NO: 137)-YVTGKQNEL (SEQ ID NO: 140)-a1-b5 | intra-protein xl | 111-128 | 102-110 |
| SDTAGREINLVDHHHHHH (SEQ ID NO: 137)-YVTGKQNEL (SEQ ID NO: 140)-a3-b5 | intra-protein xl | 111-128 | 102-110 |

*Peptide positions are indicated relative to the BTLA amino acid sequence of SEQ ID NO: 86.

Table 18 provides 7 peptides that were identified following ASP-N proteolysis, covering 26.56% of the BTLA amino acid sequence of SEQ ID NO: 86.

TABLE 18

BTLA peptides identified following ASP-N proteolysis

| Sequence | Modifications | Position Peptide 1* | Position Peptide 2 |
|---|---|---|---|
| DVQLYIKRQSEHSILAG (SEQ ID NO: 141) | | 5-21 | |
| DVQLYIKRQSEHSILAG-monolink R8-156 (SEQ ID NO: 141) | | 5-21 | |
| DTAGREINLVDHHHHHH (SEQ ID NO: 142) | | 112-128 | |
| DTAGREINLVDHHHHHH-monolink R5-155 (SEQ ID NO: 142) | | 112-128 | |
| DTAGREINLVDHHHHHH-monolink R5-156 (SEQ ID NO: 142) | | 112-128 | |
| DTAGREINLVDHHHHHH-monolink T2-155 (SEQ ID NO: 142) | | 112-128 | |
| DTAGREINLVDHHHHHH-monolink T2-156 (SEQ ID NO: 142) | | 112-128 | |

*Peptide positions are indicated relative to the BTLA amino acid sequence of SEQ ID NO: 86.

Table 19 provides 4 BTLA peptides that were identified following elastase proteolysis, covering 21.09% of the BTLA amino acid sequence of SEQ ID NO: 86.

TABLE 19

BTLA peptides identified following elastase proteolysis

| Sequence | Modifications | Position Peptide1* | Position Peptide2 |
|---|---|---|---|
| KYCANRPHV (SEQ ID NO: 143)-VDHHHHHH (SEQ ID NO: 132)-a8-b6 | intra-protein xl | 31-39 | 121-128 |

TABLE 19-continued

BTLA peptides identified following elastase proteolysis

| Sequence | Modifications | Position Peptide1* | Position Peptide2 |
|---|---|---|---|
| NRPHVTWCKL (SEQ ID NO: 144)-KQNEL (SEQ ID NO: 145)-a6-b1 | intra-protein xl | 35-44 | 106-110 |

*Peptide positions are indicated relative to the BTLA amino acid sequence of SEQ ID NO: 86.

Table 20 provides 18 BTLA peptides that were identified following thermolysin proteolysis, covering 50.00% of the BTLA amino acid sequence of SEQ ID NO: 86.

TABLE 20

BTLA peptides identified following thermolysin proteolysis

| Sequence | Modifications | Position Peptide1 | Position Peptide2 |
|---|---|---|---|
| LYIKRQSEHS (SEQ ID NO: 146)-LIESHSTT (SEQ ID NO: 147)-a7-b5 | intra-protein xl | 8-17 | 93-100 |
| IKRQSEHS (SEQ ID NO: 148)-IKRQSEHS (SEQ ID NO: 148)-a3-b3 | intra-protein xl | 10-17 | 10-17 |
| IKRQSEHS (SEQ ID NO: 148)-IKRQSEHS (SEQ ID NO: 148)-a5-b5 | intra-protein xl | 10-17 | 10-17 |
| IKRQSEHS (SEQ ID NO: 148)-KESCDVQ (SEQ ID NO: 149)-a2-b1 | intra-protein xl | 10-17 | 1-7 |
| IKRQSEHS (SEQ ID NO: 148)-VTGKQNE (SEQ ID NO: 150)-a2-b4 | intra-protein xl | 10-17 | 103-109 |
| IKRQSEHSI (SEQ ID NO: 151)-K2-156 | monolink | 10-18 | |
| VKYCANRPH (SEQ ID NO: 152)-VDHHHHHH (SEQ ID NO: 132)-a7-b4 | intra-protein xl | 30-38 | 121-128 |
| ANRPHVTWCK-K10-156 (SEQ ID NO: 153) | monolink | 34-43 | |
| VKLEDRQTSWKEEKN-K2-155 (SEQ ID NO: 154) | monolink | 50-64 | |
| VKLEDRQTSWKEEKN-K2-156 (SEQ ID NO: 154) | monolink | 50-64 | |
| IESHSTTLY (SEQ ID NO: 155)-IESHSTTLY (SEQ ID NO: 155)-a7-b7 | intra-protein xl | 94-102 | 94-102 |

*Peptide positions are indicated relative to the BTLA amino acid sequence of SEQ ID NO: 86.

In order to determine the BTLA epitope of STC613 with high resolution, the BTLA/STC613 complex was incubated with deuterated cross-linkers and subjected to multienzymatic cleavage (Asp-N, trypsin, chymotrypsin, elastase, thermolysin) and the samples were analyzed using nLC-Orbitrap mass spectrometry. Trypsin, ASP-N, and elastase digests did not result in the detection of cross-linked BTLA and STC613 peptides. Table 21 provides five cross-linked STC613 and BTLA peptides that were identified following chymotrypsin proteolysis. Table 22 provides one cross linked STC613-BTLA peptide that was identified following thermolysin proteolysis.

TABLE 21

BTLA peptides identified with deuterated cross-linker following chymotrypsin proteolysis

| Sequence | Protein 1 | Protein 2 | Sequence protein 1* | Sequence protein 2* |
|---|---|---|---|---|
| SCAASGFTF (SEQ ID NO: 156)-YIKRQSEHSIL (SEQ ID NO: 161)-a8-b8 | STC613_HC | BTLA | 21-29 | 9-19 |

TABLE 21-continued

BTLA peptides identified with deuterated cross-linker following chymotrypsin proteolysis

| Sequence | Protein 1 | Protein 2 | Sequence protein 1* | Sequence protein 2* |
|---|---|---|---|---|
| SVTIGQPASISCKSSLSL (SEQ ID NO: 157)- EDRQTSW (SEQ ID NO: 162)-a13-b5 | STC613_LC | BTLA | 12-29 | 53-59 |
| SVTIGQPASISCKSSLSL (SEQ ID NO: 157)- RCSANFQSNL-a13 (SEQ ID NO: 163)-b3 | STC613_LC | BTLA | 12-29 | 84-93 |
| TLKISRVEAEDVGVYY (SEQ ID NO: 158)- NGTTCVKL (SEQ ID NO: 164)-a15-b7 | STC613_LC | BTLA | 77-92 | 45-52 |
| KISRVEAEDVGVYY (SEQ ID NO: 159)- EPVLPNDNGSY (SEQ ID NO: 165)-a13-b10 | STC613_LC | BTLA | 79-92 | 73-83 |

*Peptide positions are indicated relative to the BTLA amino acid sequence of SEQ ID NOS: 2 and 4 (Protein 1), and SEQ ID NO: 86 (Protein 2).

TABLE 22

BTLA peptides identified with deuterated cross-linker following thermolysin proteolysis

| Sequence | Protein 1 | Protein 2 | Sequence protein 1* | Sequence protein 2* |
|---|---|---|---|---|
| ISCKSSLSL (SEQ ID NO: 160)- LYIKRQSEHSI (SEQ ID NO: 166)-a5-b5 | STM613_LC | BTLA | 103-108 | 8-18 |

*Peptide positions are indicated relative to the BTLA amino acid sequence of SEQ ID NOS: 2 and 4 (Protein 1), and SEQ ID NO: 86 (Protein 2).

FIG. 7 shows a graph illustrating the results of the higher resolution analysis of the BTLA/STC613 molecular interface. The analysis showed that the BTLA epitope of STC613 includes three regions of BTLA including the amino acid sequences

IKRQSEHSILA, (SEQ ID NO: 167)

VKLEDRQTSWK, (SEQ ID NO: 168)
and

NGSYRCSANFQ. (SEQ ID NO: 169)

The BTLA epitope of STC613 was found to include amino acids R12, H16, K51, T57, S82, and S86 of BTLA (SEQ ID NO: 86).

Throughout this application various publications have been referenced. The disclosures of these publications in their entireties are hereby incorporated by reference in this application in order to more fully describe the state of the art to which this disclosure pertains. While examples of certain particular embodiments are provided herein, it will be apparent to those skilled in the art that various changes and modifications may be made. Such modifications are also intended to fall within the scope of the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,870,287
U.S. Pat. No. 4,816,567
U.S. Pat. No. 4,867,973
U.S. Pat. No. 4,870,287
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052

U.S. Pat. No. 5,656,434
U.S. Pat. No. 5,739,169
U.S. Pat. No. 5,760,395
U.S. Pat. No. 5,770,376
U.S. Pat. No. 5,789,208
U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546
U.S. Pat. No. 7,407,659
U.S. Pat. No. 8,178,098
U.S. Patent Appln. Publn. No. 20050214860
Aurrand-Lions et al., *Immunity*, 5, 391-405(1996)
Austin-Ward and Villaseca, *Revista Medial de Chile*, 126(7):838-845(1998)
Barbas et al., *Proc. Natl. Acad. Sci. USA*, 91:3809-3813 (1994)
Barretina et al. *Nature* 483: 603-607 (2012)
Brahmer et al., *The New England journal of medicine* 366:2455-2465 (2012)
Bukowski et al., *Clinical Cancer Res.*, 4(10):2337-2347 (1998)
Chang et al., *Nature cell biology* 13: 317-323 (2011)
Chang et al., *Cancer cell* 19, 86-100.
Cheng et al., *The Journal of biological chemistry* 288: 11771-11785 (2013)
Christodoulides et al., *Microbiology*, 144(Pt 11):3027-3037 (1998)
Davidson et al., *J. Immunother* 21(5):389-398(1998)
Desmyter et al., *Nat. Struct. Biol.*, 803-811 (1996)
Dunn et al., *Nature immunology* 3: 991-998 (2002)
Francisco et al., *Immunological reviews* 236, 219-242 (2010)
Gram et al., *Proc. Natl. Acad. Sci. USA*, 89:3576-3580 (1992)
Hamers-Casterman et al., *Nature* 363: 446-448 (1993)
Hamid et al., *The New England journal of medicine* 369: 134-144 (2013)
Hanibuchi et al., *Int. J. Cancer*, 78(4):480-485 (1998)
Heifetz et al., *Biochemistry* 18: 2186-2192 (1979)
Hellstrand et al., *Acta Oncologica*, 37(4):347-353 (1998)
Hodi et al., *The New England journal of medicine* 363, 711-723 (2010).
Hollander, *Front. Immun.*, 3:3 (2012)
Hu et al., *Cancer Res.*, 56:3055-3061 (1996)
Hu et al., *Cell* 117: 225-237 (2004)
Hui and Hashimoto, *Infection Immun.*, 66(11):5329-5336 (1998)
Leach et al., *Science* 271: 1734-1736 (1996)
Lefranc et al., *Nuc. Acids Res.*, 27:209-212(1999)
Lee et al., *Cell* 130, 440-455 (2007)
Lim et al., *Gastroenterology* 135, 2128-2140 (2008)
Lin et al. *Proceedings of the National Academy of Sciences of the United States of America* 105: 3011-3016 (2008)
Liu et al., *Cell Mol. Biol.*, 49:209-216(2003)
Lo et al., *Cancer research* 67, 9066-9076 (2007)
Marks et al., *Bio/Technol.*, 10:779-783(1992)
Okazaki et al., *Nature immunology* 14: 1212-1218 (2013)
Page et al., *Annual review of medicine* 65:185-202 (2014)
Pettersen et al., *J Comput Chem* 25: 1605-1612 (2004)
Qin et al., *Proc. Natl. Acad. Sci. USA*, 95(24):14411-14416 (1998)
Robert et al., *Clinical cancer research: an official journal of the American Association for Cancer Research* 19, 2232-2239 (2013)
Robert et al., *The New England journal of medicine* 364: 2517-2526 (2011)
Schier et al., *Gene*, 169(2):147-155(1996)
Schwarz & Aebi, *Current opinion in structural biology* 21:576-582 (2011)
Shen et al., *Nature* 497: 383-387 (2013)
Sheppard et al., *FEBS letters* 574, 37-41 (2004)
Stanley, *Cold Spring Harbor perspectives in biology* 3 (2011)
Stemmer, *Nature*, 370:389-391(1994)
Topalian et al., *The New England journal of medicine* 366, 2443-2454 (2012)
Vigdorovich et al., *Structure* 21:707-717 (2013)
Winn et al., *Acta crystallographica. Section D, Biological crystallography* 67: 235-242 (2011)
Yang et al., *Investigative ophthalmology & visual science* 49: 2518-2525 (2008)

What is claimed is:

1. An antibody or antigen-binding fragment thereof that binds to BTLA, wherein the antibody or antigen-binding fragment comprises:
   a heavy chain variable region (VH) comprising:
      (1) a VH complementarity determining region (CDR) 1 having the amino acid sequence of SEQ ID NO: 12;
      (2) a VH CDR2 having the amino acid sequence of SEQ ID NO: 13; and
      (3) a VH CDR3 having the amino acid sequence of SEQ ID NO: 14; and
   a light chain variable region (VL) comprising:
      (1) a VL CDR1 having the amino acid sequence of SEQ ID NO: 24;
      (2) a VL CDR2 having the amino acid sequence of SEQ ID NO: 25, and
      (3) a VL CDR3 having the amino acid sequence of SEQ ID NO: 26.

2. The antibody or antigen-binding fragment of claim 1, wherein the antibody or antigen-binding fragment comprises a VH comprising the amino acid sequence of SEQ ID NO:2.

3. The antibody or antigen-binding fragment of claim 1, wherein the antibody or antigen-binding fragment comprises a VL comprising the amino acid sequence of SEQ ID NO:4.

4. The antibody or antigen-binding fragment of claim 1, wherein the antibody or antigen-binding fragment comprises
   a VH comprising the amino acid sequence of SEQ ID NO:2; and
   a VL comprising the amino acid sequence of SEQ ID NO:4.

5. The antibody or antigen-binding fragment of claim 1, wherein the antibody or antigen-binding fragment is recombinant.

6. The antibody or antigen-binding fragment of claim 1, wherein the antibody or antigen-binding fragment is an IgG, IgM, IgA or an antigen-binding fragment thereof.

7. The antibody or antigen-binding fragment of claim 1, wherein the antibody or antigen-binding fragment is a Fab', a F(ab')2, a F(ab')3, a monovalent scFv, a bivalent scFv, or a single domain antibody.

8. The antibody or antigen-binding fragment of claim 1, wherein the antibody or antigen-binding fragment is a human or humanized antibody.

9. The antibody or antigen-binding fragment of claim 1, wherein the antibody or antigen-binding fragment is conjugated to an imaging agent, a chemotherapeutic agent, a toxin or a radionuclide.

10. A composition comprising the antibody or antigen-binding fragment of claim 1 and a pharmaceutically acceptable carrier.

11. An antibody or antigen-binding fragment thereof that binds to BTLA, wherein the antibody or antigen-binding fragment comprises:
   a heavy chain variable region (VH) comprising:
      (1) a VH complementarity determining region (CDR) 1 having the amino acid sequence of SEQ ID NO: 40;
      (2) a VH CDR2 having the amino acid sequence of SEQ ID NO: 41; and
      (3) a VH CDR:3 having the amino acid sequence of SEQ ID NO: 42; and
   a light chain variable region (VL) comprising:
      (1) a VL CDR1 having the amino acid sequence of SEQ ID NO:52;
      (2) a VL CDR2 having the amino acid sequence of SEQ ID NO:53, and
      (3) a VL CDR3 having the amino acid sequence of SEQ ID NO:54.

12. The antibody or antigen-binding fragment of claim 1, wherein the antibody or antigen-binding fragment comprises a VH comprising the amino acid sequence of SEQ ID NO:30.

13. The antibody or antigen-binding fragment of claim 1, wherein the antibody or antigen-binding fragment comprises a VL comprising the amino acid sequence of SEQ ID NO:32.

14. The antibody or antigen-binding fragment of claim 1, wherein the antibody or antigen-binding fragment comprises:
   (a) a VH comprising the amino acid sequence of SEQ ID NO: 30; and
   (b) a VL comprising the amino acid sequence of SEQ ID NO: 32.

15. The antibody or antigen-binding fragment of claim 1, wherein the antibody or antigen-binding fragment is recombinant.

16. The antibody or antigen-binding fragment of claim 1, wherein the antibody or antigen-binding fragment is an IgG, IgM, IgA or an antigen binding fragment thereof.

17. The antibody or antigen-binding fragment of claim 1, wherein the antibody or antigen-binding fragment is a Fab', a F(ab')2, a F(ab')3, a monovalent scFv, a bivalent scFv, or a single domain antibody.

18. The antibody or antigen-binding fragment of claim 1, wherein the antibody or antigen-binding fragment is a human or humanized antibody.

19. The antibody or antigen-binding fragment of claim 1, wherein the antibody or antigen-binding fragment is conjugated to an imaging agent, a chemotherapeutic agent, a toxin or a radionuclide.

20. A composition comprising the antibody or antigen-binding fragment of claim 11 and a pharmaceutically acceptable carrier.

21. An antibody or antigen-binding fragment thereof that binds to BTLA, wherein the antibody or antigen-binding fragment comprises:
   a heavy chain variable region (VH) comprising:
      (1) a VH complementarity determining region (CDR) 1 having the amino acid sequence of SEQ ID NO:68:
      (2) a VH CDR2 having the amino acid sequence of SEQ ID NO:69; and
      (3) a VH CDR3 having the amino acid sequence of SEQ ID NO:70; and
   a light chain variable region (VL) comprising:
      (1) a VL CDR1 having the amino acid sequence of SEQ ID NO: 80,
      (2) a VL CDR2 having the amino acid sequence of SEQ ID NO:81; and
      (3) a VL CDR3 having the amino acid sequence of SEQ ID NO:82.

22. The antibody or antigen-binding fragment of claim 21, wherein the antibody or antigen-binding fragment comprises a VH comprising the amino acid sequence of SEQ ID NO:58.

23. The antibody or antigen-binding fragment of claim 21, wherein the antibody or antigen-binding fragment comprises a VL comprising the amino acid sequence of SEQ ID NO:60.

24. The antibody or antigen-binding fragment of claim 21, wherein the antibody or antigen-binding fragment comprises:
   (a) a VH comprising the amino acid sequence of SEQ ID NO: 58; and
   (b) a VL comprising the amino acid sequence of SEQ ID NO: 60.

25. The antibody or antigen-binding fragment of claim 21, wherein the antibody or antigen-binding fragment is recombinant.

26. The antibody or antigen-binding fragment of claim 21, wherein the antibody or antigen-binding fragment is an IgG, IgM, IgA or an antigen binding fragment thereof.

27. The antibody or antigen-binding fragment of claim 21, wherein the antibody or antigen-binding fragment is a Fab', a F(ab')2, a F(ab')3, a monovalent scFv, a bivalent scFv, or a single domain antibody.

28. The antibody or antigen-binding fragment of claim 21, wherein the antibody or antigen-binding fragment is a human or humanized antibody.

29. The antibody or antigen-binding fragment of claim 21, wherein the antibody or antigen-binding fragment is conjugated to an imaging agent, a chemotherapeutic agent, a toxin or a radionuclide.

30. A composition comprising the antibody or antigen-binding fragment of claim 21 and a pharmaceutically acceptable carrier.

\* \* \* \* \*